(12) United States Patent
Dunne

(10) Patent No.: US 12,109,197 B2
(45) Date of Patent: *Oct. 8, 2024

(54) COMBINATIONS OF β-LACTAM COMPOUNDS AND PROBENECID AND USES THEREOF

(71) Applicant: Iterum Therapeutics International Limited, Dublin (IE)

(72) Inventor: Michael Dunne, Old Saybrook, CT (US)

(73) Assignee: Iterum Therapeutics International Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/065,400

(22) Filed: Dec. 13, 2022

(65) Prior Publication Data

US 2023/0218588 A1 Jul. 13, 2023

Related U.S. Application Data

(63) Continuation of application No. 16/372,075, filed on Apr. 1, 2019, now Pat. No. 11,554,112.

(60) Provisional application No. 62/804,970, filed on Feb. 13, 2019, provisional application No. 62/682,116, filed on Jun. 7, 2018.

(51) Int. Cl.
| | | |
|---|---|---|
| *A61K 31/431* | (2006.01) | |
| *A61K 9/00* | (2006.01) | |
| *A61K 31/145* | (2006.01) | |
| *A61P 31/00* | (2006.01) | |

(52) U.S. Cl.
CPC .......... *A61K 31/431* (2013.01); *A61K 9/0019* (2013.01); *A61K 9/0053* (2013.01); *A61K 31/145* (2013.01); *A61P 31/00* (2018.01)

(58) Field of Classification Search
CPC .............. A61K 2300/00; A61K 31/195; A61K 31/407; A61K 31/424; A61K 31/43; A61K 31/4353; A61K 31/5365; A61K 31/545; A61K 31/145; A61K 31/431; A61K 9/0019; A61K 9/0053; A61K 47/02; A61K 47/10; A61K 47/12; A61K 47/26; A61K 47/42; A61K 9/0095; A61K 9/08; A61K 9/10; A61K 9/19; A61K 9/2004
See application file for complete search history.

(56) References Cited

U.S. PATENT DOCUMENTS

| | | | |
|---|---|---|---|
| 4,522,811 A | 6/1985 | Eppstein et al. | |
| 11,478,428 B2 | 10/2022 | Dunne et al. | |
| 11,554,112 B2 | 1/2023 | Dunne | |
| 2002/0119195 A1 | 8/2002 | Sen et al. | |
| 2005/0031685 A1 | 2/2005 | Sen et al. | |
| 2008/0009474 A1 | 1/2008 | Brighty et al. | |
| 2008/0125408 A1* | 5/2008 | Brighty .................. A61P 31/04 514/195 |
| 2012/0282336 A1 | 11/2012 | Abebe et al. | |
| 2016/0022632 A1 | 1/2016 | Rothenberg et al. | |
| 2019/0374516 A1 | 12/2019 | Dunne | |
| 2020/0253878 A1 | 8/2020 | Dunne et al. | |
| 2021/0154176 A1 | 5/2021 | Dunne et al. | |
| 2021/0283112 A1 | 9/2021 | Dunne | |
| 2023/0138191 A1 | 5/2023 | Dunne et al. | |

FOREIGN PATENT DOCUMENTS

| | | | |
|---|---|---|---|
| CN | 1813700 A | 8/2006 | |
| CN | 1853724 A | 11/2006 | |
| CN | 101479279 A | 7/2009 | |
| EP | 3238713 A1 | 11/2017 | |
| JP | S58128387 A | 7/1983 | |
| JP | 2009542616 A | 12/2009 | |
| TW | 200816999 A | 4/2008 | |
| WO | WO-9949875 A1 | 10/1999 | |
| WO | WO-0236126 A1 | 5/2002 | |
| WO | WO-0241876 A1 | 5/2002 | |
| WO | WO-03043607 A1 | 5/2003 | |
| WO | WO-2008001212 A2 * | 1/2008 | ......... C07D 499/887 |

OTHER PUBLICATIONS

William et al, (Clinical Nutrition, vol. 77, No. 4, Jul. 1993). (Year: 1993).*
Ambrose, P. G. et al., "Pharmacokinetics-Pharmacodynamics of Antimicrobial Therapy: It's Not Just for Mice Anymore," Clinical Infectious Diseases, 44:79-86 (2007).
Chandra, R. et al., "Pharmacokinetics (PK), Safety and Tolerability of Single Oral Doses of PF-03709270, with and without Co-Administration of Probenecid," Jan. 1, 2008, Abstract, Interscience Conference on Antimicrobial Agents & Chemotherapy (ICAAC), vol. 48, 1 page.
Chandra, R. et al., "Pharmacokinetics (PK), Safety and Tolerability of Single Oral Doses of PF-03709270, with and without Co-Administration of Probenecid—Introduction," Oct. 25, 2008, retrieved from the Internet: https://dli03yog0oux5.cloudfront.net/bb13d2baffc18226d0c894be0676522b/iterumtx/db/395/2620/pdf, 1 page.
Cox, V. C. & Zed, P. J., "Once-Daily Cefazolin and Probenecid for Skin and Soft Tissue Infections," Ann Pharmacother, 38:450-463 (2004).
Cunningham, R. F. et al., "Clinical Pharmacokinetics of Probenecid," Clinical Pharmacokinetics, 6:135-151 (1981).

(Continued)

*Primary Examiner* — Jean P Cornet
(74) *Attorney, Agent, or Firm* — COOLEY LLP

(57) ABSTRACT

The present disclosure relates to combinations of a β-lactam compound or a pharmaceutically acceptable salt thereof and probenecid or a pharmaceutically acceptable salt thereof. The present disclosure also relates to methods of treating or preventing a disease via administering to subjects in need thereof a β-lactam compound or a pharmaceutically acceptable salt thereof and probenecid or a pharmaceutically acceptable salt thereof.

10 Claims, 5 Drawing Sheets

(56) References Cited

OTHER PUBLICATIONS

Dacey, R. G. & Sande, M. A., "Effect of Probenecid on Cerebrospinal Fluid Concentrations of Penicillin and Cephalosporin Derivatives," Antimicrobial Agents and Chemotherapy, 6(4):437-441 (1974).
Dalen, D. et al., "Intravenous cefazolin plus oral probenecid versus oral cephalexin for the treatment of skin and soft tissue infections: a double-blind, non-inferiority, randomised controlled trial," Emergency Medicine Journal, 35(8):492-498 (2018).
Dominy, S.S. et al. (2019). "Porphyromonas gingiva/is in Alzheimer's disease brains: Evidence for disease causation and treatment with small-molecule inhibitors," Sci Adv. 5:eaau333, 21 total pages.
Dorwald, F.Z., "Side Reactions in Organic Synthesis: A Guide to Successful Synthesis Design," Weinheim: Wiley-VCH Verlag Gmbh & Co. KGaA, Preface (2005), 4 pages.
Dunne, M. et al., "A Phase 1, Randomized, Open-Label, Crossover Study in Healthy Subjects Under Fasting Conditions of Orally Administered Sulopenem Etzadroxil Alone or with Probenecid to Determine the Pharmacokinetics of Sulopenem," Poster Abstracts, OFID 2018:5 (Suppl 1):S428-S429, 2 pages.
Dunne, M. et al., "A Phase 1 Study to Assess the Pharmacokinetics of Sulopenem Etzadroxil (PF-03709270)," Poster Abstracts, OFID 2017:4 (Suppl 1):S525-S526, 2 pages.
Ednie, L. M. & Applebaum, P. C., "Antianaerobic Activity of Sulopenem Compared to Six Other Agents," Antimicrobial Agents and Chemotherapy, 53(5):2163-2170 (2009).
Forrest, A. et al., "PK/PD Analysis to Select PF-03709270 (PF) Doses, With & Without Probenecid (P), for Phase 2b Trials," Abstract, Interscience Conference on Antimicrobial Agents & Chemotherapy (ICAAC), vol. 48, Oct. 25, 2008, 1 page.
Gootz, T. et al., "Pharmacokinetic studies in animals of a new parenteral penem CP-65,207 and its oral prodrug ester," The Journal of Antibiotics, 43(4):422-432 (1990).
"Iterum Initiates SURE 2 and SURE 3 Phase 3 Clinical Trials of IV and Oral Sulopenem in Complicated Urinary Tract and Complicated Intra-abdominal Infections," [Online], Sep. 18, 2018, [Retrieved on Jan. 5, 2023], URL: https://www.iterumtx.com/news/press-releases/detail/12/iterum-initiates-sure-2-and-sure-3-phase-3-clinical-trials, 3 pages.
Karlowsky, J. A. et al., "In Vitro Activity of Sulopenem, an Oral Penem, against Urinary Isolates of *Escherichia coli*," Antimicrob Agents Chemother 63(1):e01832-18 (2019), 7 pages; https://doi.org/10.1128/AAC.01832-18.
Le, J. et al., "Drug Bioavailability," Oct. 2020, 2 pages; https://www.merckmanuals.com/professional/clinical-pharmacology/pharmacokinetics/drug-bioavalability#.
Probenicid, Tulane University, Medical Pharmacology, 2016; http://tmedweb.tulane.edu/pharmawiki/doku.php/probenecid , 3 pages.
Problems with Urination, Military Obstetrics & Gynecology, 2009, 2014, 8 pages.
Soma, K. et al., "Pharmacokinetics (PK), Safety and Tolerability of Multiple Doses (MD) of Intravenous (IV) and Oral (PO) Sulopenem (S) and Sulopenem Etzadroxil (SE)," 2009, Abstract, Interscience Conference on Antimicrobial Agents & Chemotherapy (ICAAC), vol. 49, 2 pages.
Stamm, W. E., "An Epidemic of Urinary Tract Infections?" Editorials—N Engl J Med, 345(14):1055-1057 (2001).
Stocker, S. L. et al., Pharmacokinetic and Pharmacodynamic Interaction Between Allopurinol and Probenecid in Patients with Gout, J. Rheumatol, 38:904-910 (2011).
Van Der Merwe, J. et al., "The Role of Functional Excipients in Solid Oral Dosage Forms to Overcome Poor Drug Dissolution and Bioavailability," Pharmaceutics, 12:393 (2020), 17 pages.

\* cited by examiner

COMBINATIONS OF β-LACTAM COMPOUNDS AND PROBENECID AND USES THEREOF

RELATED APPLICATIONS

This application is a continuation of U.S. patent application Ser. No. 16/372,075, filed on Apr. 1, 2019, now U.S. Pat. No. 11,554,112, which claims priority to, and the benefit of, U.S. Provisional Application Nos. 62/804,970, filed Feb. 13, 2019, and 62/682,116, filed Jun. 7, 2018, the entire contents of each of which are incorporated herein by reference.

BACKGROUND

β-lactam compounds are a class of antibiotics having a beta-lactam ring in their molecular structures. β-lactam compounds have been used in the treatment of diseases associated with Gram-positive and Gram-negative bacteria. The mechanism of action of these β-lactam compounds requires, optimally, that concentrations of the antibiotic remain at or above a certain inhibitory threshold, known as the 'mean inhibitory concentration (MIC)' in order to be effective. Keeping these antibiotic concentrations elevated also helps avoid the potential for antibacterial resistance due to the selection of bacteria with higher MIC's. There is, therefore, a need for compositions and methods related to β-lactam antibiotics that optimize their tissue concentrations in order to improve their ability to control an infection as well as alleviate or eliminate the potential for antibiotic resistance.

SUMMARY

The present disclosure provides, inter alia, a method of treating or preventing a disease, comprising administering to a subject in need thereof a pharmaceutically effective amount of a β-lactam compound or a pharmaceutically acceptable salt thereof and probenecid or a pharmaceutically acceptable salt thereof, wherein the β-lactam compound or the pharmaceutically acceptable salt thereof and probenecid or the pharmaceutically acceptable salt thereof are administered by the same administration route.

In some embodiments, the β-lactam compound or the pharmaceutically acceptable salt thereof and probenecid or the pharmaceutically acceptable salt thereof are administered simultaneously.

In some embodiments, the β-lactam compound or the pharmaceutically acceptable salt thereof and probenecid or the pharmaceutically acceptable salt thereof are both administered by enteral administration.

In some embodiments, the enteral administration is oral administration.

In some embodiments, an oral co-formulation comprising the β-lactam compound or the pharmaceutically acceptable salt thereof and probenecid or the pharmaceutically acceptable salt thereof is administered.

In some embodiments, the β-lactam compound or the pharmaceutically acceptable salt thereof and probenecid or the pharmaceutically acceptable salt thereof are both administered in separate oral formulations.

In some embodiments, the administration results in a plasma concentration for the β-lactam compound having an area under the curve (AUC) that is higher in the subject in need thereof as compared to a comparable subject being administered with the β-lactam compound and probenecid by different administration routes.

In some embodiments, the administration results in a plasma concentration for the β-lactam compound having a maximum plasma concentration ($C_{max}$) in the subject in need thereof that is substantially the same as compared to a comparable subject being administered with the β-lactam compound and probenecid by different administration routes.

In some embodiments, the administration results in a plasma concentration for the β-lactam compound having:
  an area under the curve (AUC) that is higher in the subject in need thereof as compared to a comparable subject being administered with the β-lactam compound and probenecid by different administration routes; and
  a plasma concentration for the β-lactam compound having a maximum plasma concentration ($C_{max}$) in the subject in need thereof that is substantially the same as compared to a comparable subject being administered with the β-lactam compound and probenecid by different administration routes.

In some aspects, the present disclosure provides, a method of treating or preventing a disease, comprising administering to a subject in need thereof a pharmaceutically effective amount of a β-lactam compound or a pharmaceutically acceptable salt thereof and probenecid or a pharmaceutically acceptable salt thereof over a period of time, wherein the administration results in a plasma concentration for the β-lactam compound having:
  an area under the curve (AUC) that is higher in the subject in need thereof as compared to a comparable subject being administered to the pharmaceutically effective amount of the β-lactam compound without probenecid over the period of time,
  a maximum plasma concentration ($C_{max}$) that is higher in the subject in need thereof as compared to the comparable subject being administered to the pharmaceutically effective amount of the β-lactam compound without probenecid over the period of time, or
  a combination thereof.

In some aspects, the present disclosure provides a β-lactam compound or a pharmaceutically acceptable salt thereof for use in combination with probenecid or a pharmaceutically acceptable salt thereof in treating or preventing a disease in a subject in need thereof, wherein the β-lactam compound or the pharmaceutically acceptable salt thereof and probenecid or the pharmaceutically acceptable salt thereof are administered to the subject by the same administration route.

In some aspects, the present disclosure provides probenecid or a pharmaceutically acceptable salt thereof for use in combination with a β-lactam compound or a pharmaceutically acceptable salt thereof in treating or preventing a disease in a subject in need thereof, wherein the β-lactam compound or the pharmaceutically acceptable salt thereof and probenecid or the pharmaceutically acceptable salt thereof are administered to the subject by the same administration route.

In some aspects, the present disclosure provides a combination of a β-lactam compound or a pharmaceutically acceptable salt thereof and probenecid or a pharmaceutically acceptable salt thereof for use in treating or preventing a disease in a subject in need thereof, wherein the β-lactam compound or the pharmaceutically acceptable salt thereof and probenecid or the pharmaceutically acceptable salt thereof are administered to the subject by the same administration route.

In some aspects, the present disclosure provides use of a β-lactam compound in combination with probenecid or a pharmaceutically acceptable salt thereof in the manufacture of a medicament for treating or preventing a disease in a subject in need thereof, wherein the β-lactam compound or the pharmaceutically acceptable salt thereof and probenecid or the pharmaceutically acceptable salt thereof are administered to the subject by the same administration route.

In some aspects, the present disclosure provides use of probenecid in combination with a β-lactam compound or a pharmaceutically acceptable salt thereof in the manufacture of a medicament for treating or preventing a disease in a subject in need thereof, wherein the β-lactam compound or the pharmaceutically acceptable salt thereof and probenecid or the pharmaceutically acceptable salt thereof are administered to the subject by the same administration route.

In some aspects, the present disclosure provides use of a combination of a β-lactam compound or a pharmaceutically acceptable salt thereof and probenecid or a pharmaceutically acceptable salt thereof in the manufacture of a medicament for treating or preventing a disease in a subject in need thereof, wherein the β-lactam compound or the pharmaceutically acceptable salt thereof and probenecid or the pharmaceutically acceptable salt thereof are administered to the subject by the same administration route.

In some aspects, the present disclosure provides a β-lactam compound or a pharmaceutically acceptable salt thereof for use in combination with probenecid or a pharmaceutically acceptable salt thereof in treating or preventing a disease, wherein:
  the β-lactam compound or the pharmaceutically acceptable salt thereof and the probenecid or a pharmaceutically acceptable salt thereof are administered to a subject in need over a period of time, wherein the administration results in a plasma concentration for the β-lactam compound having:
  an area under the curve (AUC) that is higher in the subject in need thereof as compared to a comparable subject being administered to the pharmaceutically effective amount of the β-lactam compound without probenecid over the period of time,
  a maximum plasma concentration ($C_{max}$) that is higher in the subject in need thereof as compared to the comparable subject being administered to the pharmaceutically effective amount of the β-lactam compound without probenecid over the period of time, or
  a combination thereof.

In some aspects, the present disclosure provides probenecid or a pharmaceutically acceptable salt thereof for use in combination with a β-lactam compound or a pharmaceutically acceptable salt thereof in treating or preventing a disease, wherein:
  the β-lactam compound or the pharmaceutically acceptable salt thereof and the probenecid or a pharmaceutically acceptable salt thereof are administered to a subject in need over a period of time, wherein the administration results in a plasma concentration for the β-lactam compound having:
  an area under the curve (AUC) that is higher in the subject in need thereof as compared to a comparable subject being administered to the pharmaceutically effective amount of the β-lactam compound without probenecid over the period of time,
  a maximum plasma concentration ($C_{max}$) that is higher in the subject in need thereof as compared to the comparable subject being administered to the pharmaceutically effective amount of the β-lactam compound without probenecid over the period of time, or
  a combination thereof.

In some aspects, the present disclosure provides a combination of a β-lactam compound or a pharmaceutically acceptable salt thereof and probenecid or a pharmaceutically acceptable salt thereof for use in treating or preventing a disease, wherein:
  the β-lactam compound or the pharmaceutically acceptable salt thereof and the probenecid or a pharmaceutically acceptable salt thereof are administered to a subject in need over a period of time, wherein the administration results in a plasma concentration for the β-lactam compound having:
  an area under the curve (AUC) that is higher in the subject in need thereof as compared to a comparable subject being administered to the pharmaceutically effective amount of the β-lactam compound without probenecid over the period of time,
  a maximum plasma concentration ($C_{max}$) that is higher in the subject in need thereof as compared to the comparable subject being administered to the pharmaceutically effective amount of the β-lactam compound without probenecid over the period of time, or
  a combination thereof.

In some aspects, the present disclosure provides use of a β-lactam compound or a pharmaceutically acceptable salt thereof in combination with probenecid or a pharmaceutically acceptable salt thereof in the manufacture of a medicament for treating or preventing a disease, wherein administration of the medicament to a subject in need over a period of time results in a plasma concentration for the β-lactam compound having:
  an area under the curve (AUC) that is higher in the subject in need thereof as compared to a comparable subject being administered to the pharmaceutically effective amount of the β-lactam compound without probenecid over the period of time,
  a maximum plasma concentration ($C_{max}$) that is higher in the subject in need thereof as compared to the comparable subject being administered to the pharmaceutically effective amount of the β-lactam compound without probenecid over the period of time, or
  a combination thereof.

In some aspects, the present disclosure provides use of probenecid or a pharmaceutically acceptable salt thereof in combination with a β-lactam compound or a pharmaceutically acceptable salt thereof in the manufacture of a medicament for treating or preventing a disease, wherein administration of the medicament to a subject in need over a period of time results in a plasma concentration for the β-lactam compound having:
  an area under the curve (AUC) that is higher in the subject in need thereof as compared to a comparable subject being administered to the pharmaceutically effective amount of the β-lactam compound without probenecid over the period of time,
  a maximum plasma concentration ($C_{max}$) that is higher in the subject in need thereof as compared to the comparable subject being administered to the pharmaceutically effective amount of the β-lactam compound without probenecid over the period of time, or
  a combination thereof.

In some aspects, the present disclosure provides use of a combination of a β-lactam compound or a pharmaceutically acceptable salt thereof and probenecid or a pharmaceutically acceptable salt thereof in the manufacture of a medicament for treating or preventing a disease, wherein administration of the medicament to a subject in need over a period of time results in a plasma concentration for the β-lactam compound having:

the β-lactam compound or the pharmaceutically acceptable salt thereof and the probenecid or a pharmaceutically acceptable salt thereof are administered to a subject in need over a period of time, wherein the administration results in a plasma concentration for the β-lactam compound having:

an area under the curve (AUC) that is higher in the subject in need thereof as compared to a comparable subject being administered to the pharmaceutically effective amount of the β-lactam compound without probenecid over the period of time, a maximum plasma concentration ($C_{max}$) for the β-lactam compound that is higher in the subject in need thereof as compared to the comparable subject being administered to the pharmaceutically effective amount of the β-lactam compound without probenecid over the period of time, or a combination thereof.

In some aspects, the present disclosure provides a pharmaceutical composition comprising a β-lactam compound or a pharmaceutically acceptable salt thereof and probenecid or a pharmaceutically acceptable salt thereof.

In some aspects, the present disclosure provides a pharmaceutical kit comprising a β-lactam compound or a pharmaceutically acceptable salt thereof in a first package and probenecid or a pharmaceutically acceptable salt thereof in a second package.

In some aspects, the present disclosure provides a compound or a pharmaceutical salt thereof, wherein administration of the compound or the pharmaceutical salt thereof in combination with probenecid or a pharmaceutically acceptable salt thereof into a subject in need thereof over a period of time results in a plasma concentration versus time curve for the compound having:

an area under the curve (AUC) that is higher in the subject in need thereof as compared to a comparable subject being administered to the pharmaceutically effective amount of the compound without probenecid over the period of time, a maximum plasma concentration ($C_{max}$) for the compound that is higher in the subject in need thereof as compared to the comparable subject being administered to the pharmaceutically effective amount of the compound without probenecid over the period of time, or a combination thereof.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following detailed description and claims.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
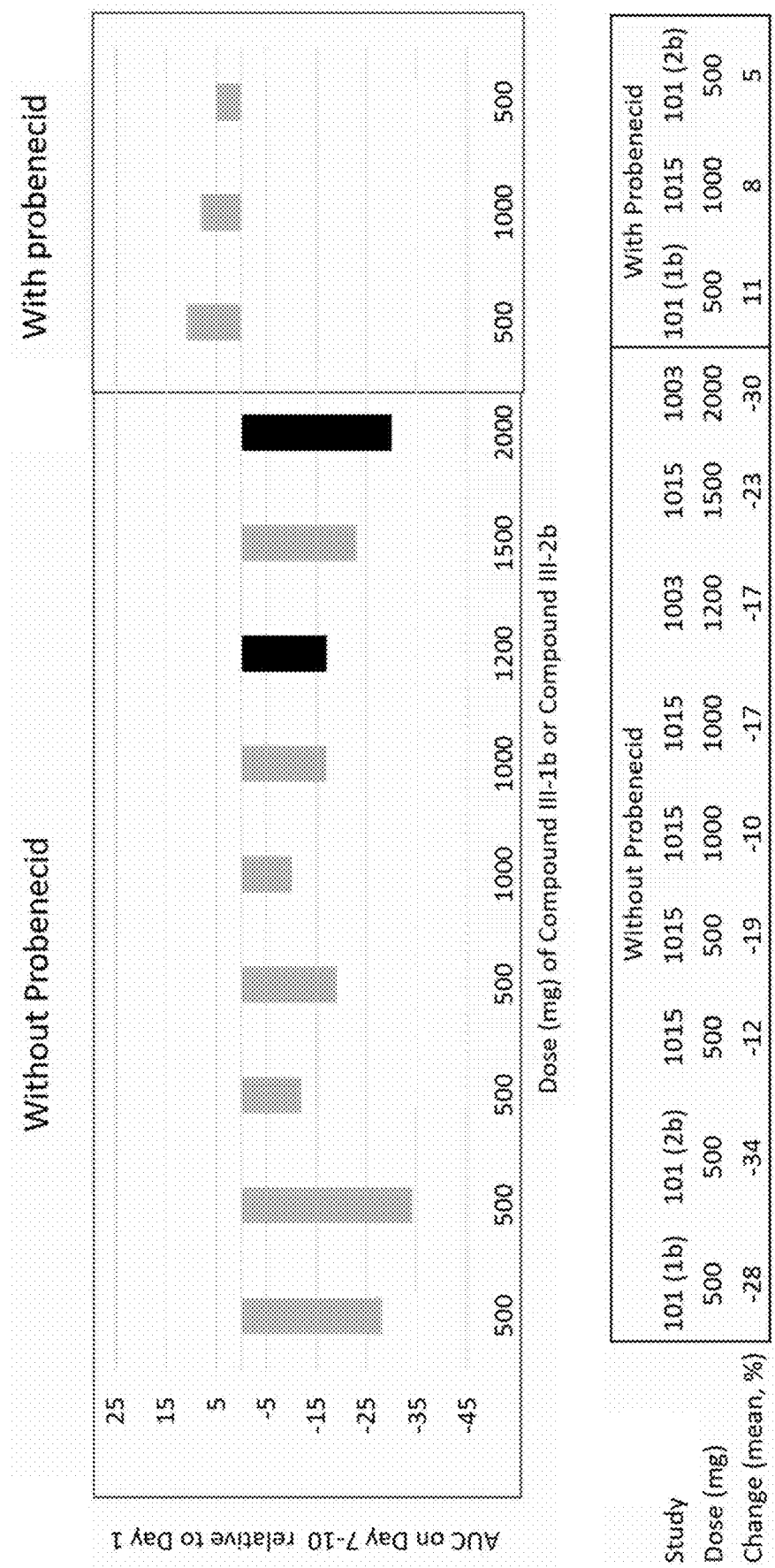
FIG. 1 is a graph showing the effect of probenecid on the area under the curve (AUC) of sulopenem in the plasma when delivered through the oral route with an oral sulopenem prodrug.
Figure 2:
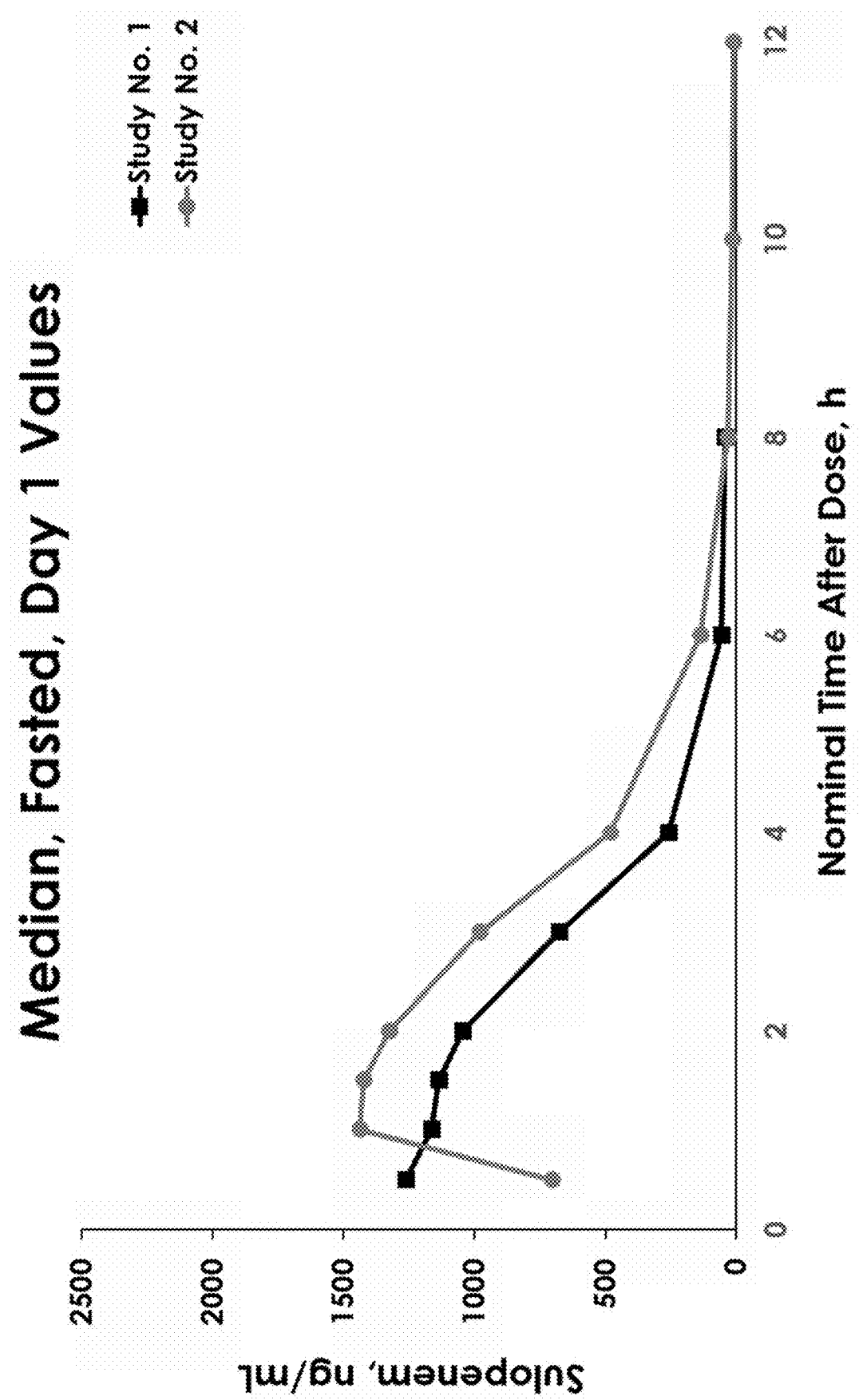
FIG. 2 is a diagram showing the effect of administrating the β-lactam compound (Compound III-2b) and probencid in the fasted state on the plasma level of the β-lactam compound (Compound IIb).
Figure 3:
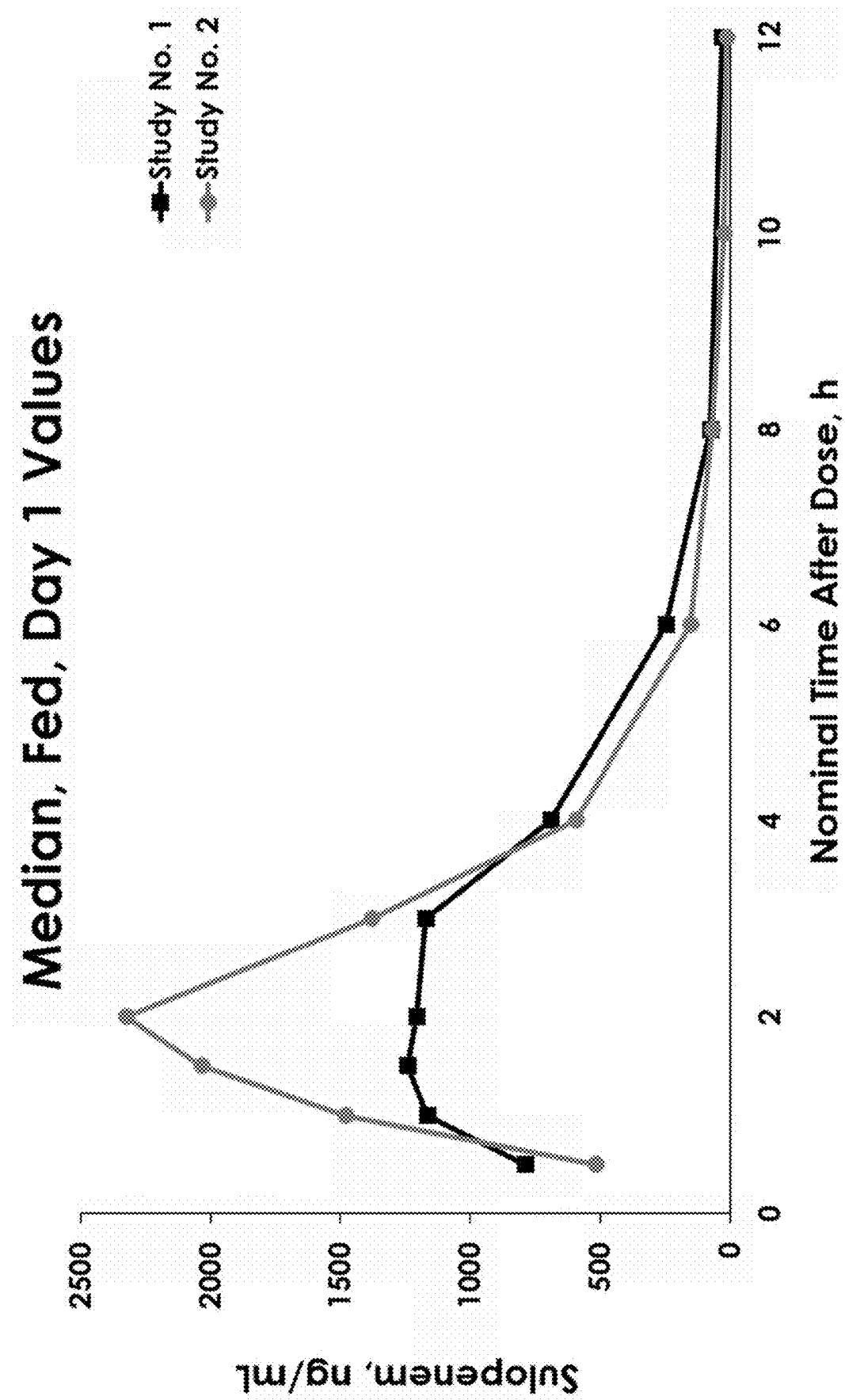
FIG. 3 is a diagram showing the effect of administrating the β-lactam compound (Compound III-2b) and probencid in the fed state on the plasma level of the β-lactam compound (Compound IIb).
Figure 4:
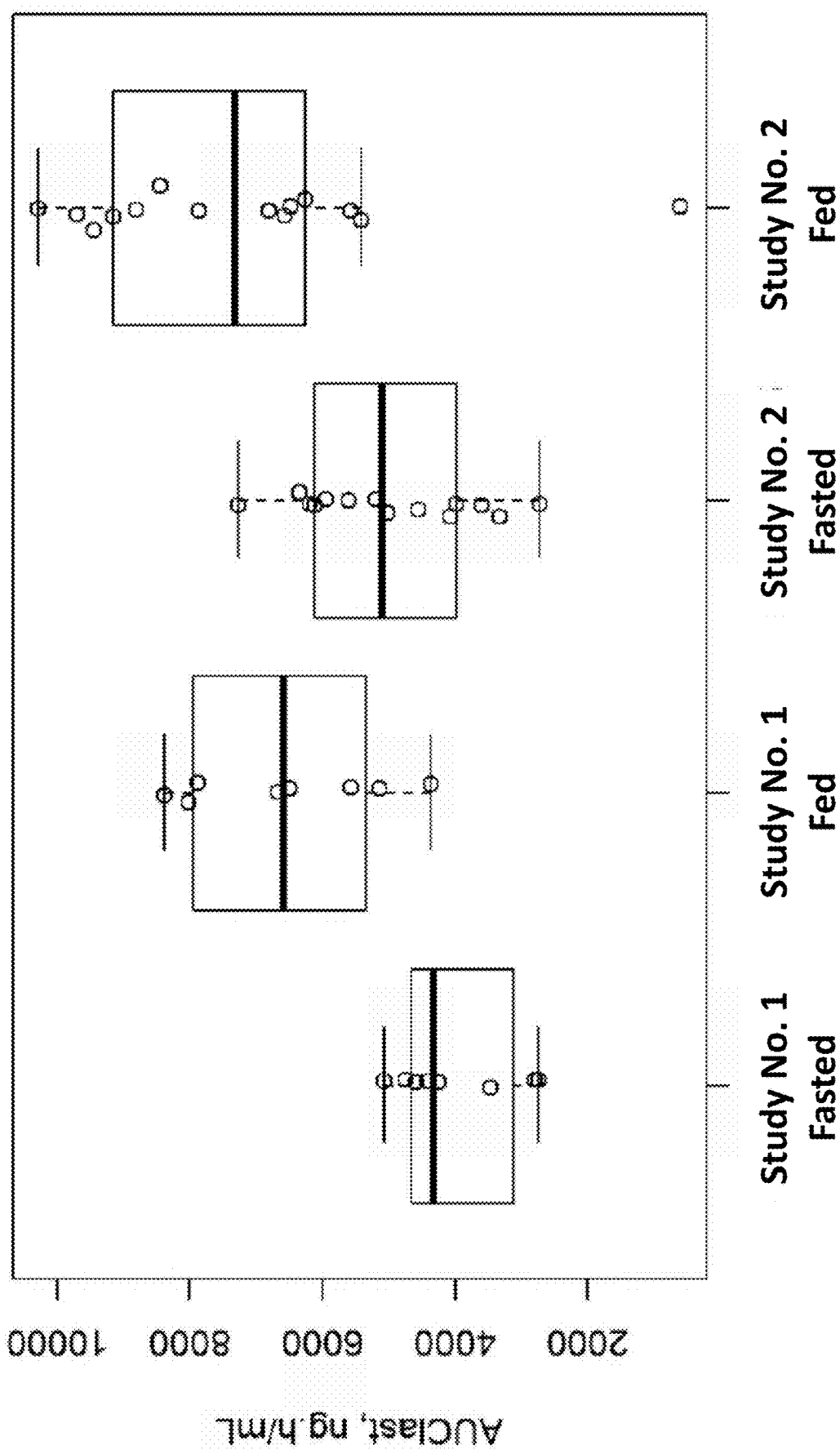
FIG. 4 is a graph showing the effect of administering a β-lactam compound (Compound III-2b) and probenecid by the same administration route (as compared to by different administration routes) on the area under the curve (AUC) for the β-lactam compound (Compound IIb).
Figure 5:
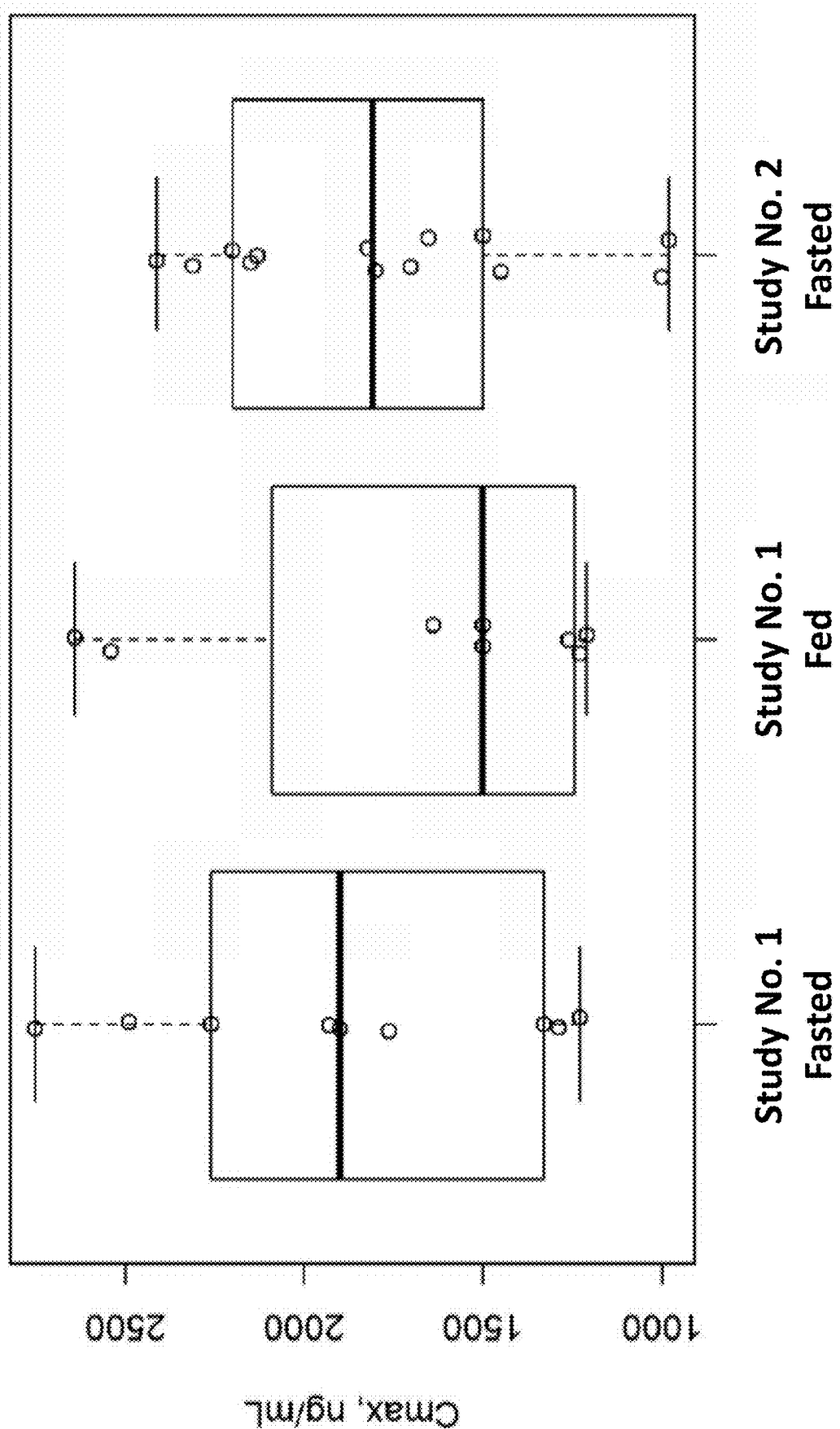
FIG. 5 is a graph showing the effect of administering a β-lactam compound (Compound III-2b) and probenecid by the same administration route (as compared to by different administration routes) on the maximum plasma concentration ($C_{max}$) for the β-lactam compound (Compound III-2b).

The present disclosure provides, inter alia, a method of treating or preventing a disease, comprising administering to a subject in need thereof a pharmaceutically effective amount of a β-lactam compound or a pharmaceutically acceptable salt thereof and probenecid or a pharmaceutically acceptable salt thereof, wherein the β-lactam compound or the pharmaceutically acceptable salt thereof and probenecid or the pharmaceutically acceptable salt thereof are administered by the same administration route.

In some aspects, the present disclosure provides a method of treating or preventing a disease, comprising administering to a subject in need thereof a pharmaceutically effective amount of a β-lactam compound or a pharmaceutically acceptable salt thereof and probenecid or a pharmaceutically acceptable salt thereof over a period of time, wherein the administration results in a plasma concentration for the β-lactam compound having:

an area under the curve (AUC) that is higher in the subject in need thereof as compared to a comparable subject being administered to the pharmaceutically effective amount of the β-lactam compound without probenecid over the period of time, a maximum plasma concentration ($C_{max}$) that is higher in the subject in need thereof as compared to the comparable subject being administered to the pharmaceutically effective amount of the β-lactam compound without probenecid over the period of time, or a combination thereof.

In some embodiments, the period of the time is longer than about 24 hours.

In some embodiments, the period of the time ranges from about 2 days to about 30 days, from about 3 days to about 20 days, from about 4 days to about 15 days, from about 5 days to about 10 days, or from about 6 days to about 8 days.

In some embodiments, the period of the time is about 7 days.

Effects on the AUC and/or $C_{max}$

In some embodiments, the administration results in a plasma concentration for the β-lactam compound having an area under the curve (AUC) that is higher in the subject in need thereof as compared to a comparable subject being administered with the β-lactam compound and probenecid by different administration routes.

In some embodiments, the administration results in a plasma concentration for the β-lactam compound having an area under the curve (AUC) that is higher in the subject in need thereof as compared to a comparable subject being administered with the β-lactam compound and probenecid by different administration routes by about 5% or greater, about 10% or greater, about 15% or greater, about 20% or greater, about 25% or greater, about 30% or greater, about 40% or greater, about 50% or greater, about 60% or greater, about 80% or greater, about 100% or greater, about 150% or greater, about 200% or greater, about 300% or greater, about 400% or greater, or about 500% or greater within about 30 minutes, about 1 hour, about 2 hours, about 3 hours, about 6 hours, about 12 hours, about 18 hours, about 1 day, about 2 days, about 3 days, about 4 days, about 5 days, about 6 days, or about 7 days from the administration.

In some embodiments, the administration results in a plasma concentration for the β-lactam compound having an area under the curve (AUC) that is higher in the subject in need thereof as compared to a comparable subject being administered with the β-lactam compound and probenecid by different administration routes about 10% or greater, about 15% or greater, about 20% or greater, about 25% or greater, or about 30% or greater within about 12 hours, about 18 hours, about 1 day, about 2 days, or about 3 days from the administration.

In some embodiments, the administration results in a plasma concentration for the β-lactam compound having an area under the curve (AUC) that is higher in the subject in need thereof as compared to a comparable subject being administered with the β-lactam compound and probenecid by different administration routes about 15% or greater, about 20% or greater, or about 25% or greater within about 18 hours, about 1 day, or about 2 days from the administration.

In some embodiments, the administration results in a plasma concentration for the 0-lactam compound having an area under the curve (AUC) that is higher in the subject in need thereof as compared to a comparable subject being administered with the β-lactam compound and probenecid by different administration routes about 15% or greater, about 20% or greater, or about 25% or greater within about 18 hours from the administration.

In some embodiments, the administration results in a plasma concentration for the β-lactam compound having an area under the curve (AUC) that is higher in the subject in need thereof as compared to a comparable subject being administered with the β-lactam compound and probenecid by different administration routes about 15% or greater, about 20% or greater, or about 25% or greater within about 1 day from the administration.

In some embodiments, the administration results in a plasma concentration for the β-lactam compound having an area under the curve (AUC) that is higher in the subject in need thereof as compared to a comparable subject being administered with the β-lactam compound and probenecid by different administration routes about 15% or greater, about 20% or greater, or about 25% or greater within about 2 days from the administration.

In some embodiments, the administration results in a plasma concentration for the β-lactam compound having an area under the curve (AUC) that is higher in the subject in need thereof as compared to a comparable subject being administered with the β-lactam compound and probenecid by different administration routes by about 20% or greater within about 1 day from the administration.

In some embodiments, the administration results in a plasma concentration for the β-lactam compound having a maximum plasma concentration ($C_{max}$) in the subject in need thereof that is from about 50% to about 150%, from about 60% to about 140%, from about 70% to about 130%, from about 80% to about 120%, from about 90% to about 110%, from about 95% to about 105%, or from 98% to about 102% as compared to a comparable subject being administered with the β-lactam compound and probenecid by different administration routes.

In some embodiments, the administration results in a plasma concentration for the β-lactam compound having a maximum plasma concentration ($C_{max}$) in the subject in need thereof that is from about 70% to about 130%, from about 80% to about 120%, from about 90% to about 110%, from about 95% to about 105%, or from 98% to about 102% as compared to a comparable subject being administered with the β-lactam compound and probenecid by different administration routes.

In some embodiments, the administration results in a plasma concentration for the β-lactam compound having a maximum plasma concentration ($C_{max}$) in the subject in need thereof that is from about 90% to about 110%, from about 95% to about 105%, or from 98% to about 102% as compared to a comparable subject being administered with the β-lactam compound and probenecid by different administration routes.

In some embodiments, the administration results in a plasma concentration for the β-lactam compound having a maximum plasma concentration ($C_{max}$) in the subject in need thereof that is from about 95% to about 105%, or from 98% to about 102% as compared to a comparable subject being administered with the β-lactam compound and probenecid by different administration routes.

In some embodiments, the administration results in a plasma concentration for the β-lactam compound having a maximum plasma concentration ($C_{max}$) in the subject in need thereof that is from 98% to about 102% as compared to a comparable subject being administered with the β-lactam compound and probenecid by different administration routes.

In some embodiments, administration results in a plasma concentration for the β-lactam compound having a maximum plasma concentration ($C_{max}$) in the subject in need thereof that is substantially the same as compared to a comparable subject being administered with the β-lactam compound and probenecid by different administration routes.

In some embodiments, the administration results in a plasma concentration for the β-lactam compound having:

an area under the curve (AUC) that is higher in the subject in need thereof as compared to a comparable subject being administered with the β-lactam compound and probenecid by different administration routes; and a maximum plasma concentration ($C_{max}$) in the subject in need thereof that is substantially the same as compared to a comparable subject being administered with the β-lactam compound and probenecid by different administration routes.

In some embodiments, the administration results in a plasma concentration for the β-lactam compound having:
an area under the curve (AUC) that is higher in the subject in need thereof as compared to a comparable subject being administered with the β-lactam compound and probenecid by different administration routes by about 5% or greater, about 10% or greater, about 15% or greater, about 20% or greater, about 25% or greater, about 30% or greater, about 40% or greater, about 50% or greater, about 60% or greater, about 80% or greater, about 100% or greater, about 150% or greater, about 200% or greater, about 300% or greater, about 400% or greater, or about 500% or greater within about 30 minutes, about 1 hour, about 2 hours, about 3 hours, about 6 hours, about 12 hours, about 18 hours, about 1 day, about 2 days, about 3 days, about 4 days, about 5 days, about 6 days, or about 7 days from the administration.

In some embodiments, the administration results in a plasma concentration for the β-lactam compound having:
an area under the curve (AUC) that is higher in the subject in need thereof as compared to a comparable subject being administered with the β-lactam compound and probenecid by different administration routes by about 5% or greater, about 10% or greater, about 15% or greater, about 20% or greater, about 25% or greater, about 30% or greater, about 40% or greater, about 50% or greater, about 60% or greater, about 80% or greater, about 100% or greater, about 150% or greater, about 200% or greater, about 300% or greater, about 400% or greater, or about 500% or greater within about 30 minutes, about 1 hour, about 2 hours, about 3 hours, about 6 hours, about 12 hours, about 18 hours, about 1 day, about 2 days, about 3 days, about 4 days, about 5 days, about 6 days, or about 7 days from the administration; and
a maximum plasma concentration ($C_{max}$) in the subject in need thereof that is from about 50% to about 150%, from about 60% to about 140%, from about 70% to about 130%, from about 80% to about 120%, from about 90% to about 110%, from about 95% to about 105%, or from 98% to about 102% as compared to a comparable subject being administered with the β-lactam compound and probenecid by different administration routes.

In some embodiments, the administration results in a plasma concentration for the β-lactam compound having:
an area under the curve (AUC) that is higher in the subject in need thereof as compared to a comparable subject being administered with the β-lactam compound and probenecid by different administration routes by about 5% or greater, about 10% or greater, about 15% or greater, about 20% or greater, about 25% or greater, about 30% or greater, about 40% or greater, about 50% or greater, about 60% or greater, about 80% or greater, about 100% or greater, about 150% or greater, about 200% or greater, about 300% or greater, about 400% or greater, or about 500% or greater within about 30 minutes, about 1 hour, about 2 hours, about 3 hours, about 6 hours, about 12 hours, about 18 hours, about 1 day, about 2 days, about 3 days, about 4 days, about 5 days, about 6 days, or about 7 days from the administration; and
a maximum plasma concentration ($C_{max}$) in the subject in need thereof that is substantially the same as compared to a comparable subject being administered with the β-lactam compound and probenecid by different administration routes.

In some embodiments, the administration results in a plasma concentration for the β-lactam compound having:
an area under the curve (AUC) that is higher in the subject in need thereof as compared to a comparable subject being administered with the β-lactam compound and probenecid in separate formulations by about 5% or greater, about 10% or greater, about 15% or greater, about 20% or greater, about 25% or greater, about 30% or greater, about 40% or greater, about 50% or greater, about 60% or greater, about 80% or greater, about 100% or greater, about 150% or greater, about 200% or greater, about 300% or greater, about 400% or greater, or about 500% or greater within about 30 minutes, about 1 hour, about 2 hours, about 3 hours, about 6 hours, about 12 hours, about 18 hours, about 1 day, about 2 days, about 3 days, about 4 days, about 5 days, about 6 days, or about 7 days from the administration.

In some embodiments, the administration results in a plasma concentration for the β-lactam compound having:
an area under the curve (AUC) that is higher in the subject in need thereof as compared to a comparable subject being administered with the β-lactam compound and probenecid in separate formulations by about 5% or greater, about 10% or greater, about 15% or greater, about 20% or greater, about 25% or greater, about 30% or greater, about 40% or greater, about 50% or greater, about 60% or greater, about 80% or greater, about 100% or greater, about 150% or greater, about 200% or greater, about 300% or greater, about 400% or greater, or about 500% or greater within about 30 minutes, about 1 hour, about 2 hours, about 3 hours, about 6 hours, about 12 hours, about 18 hours, about 1 day, about 2 days, about 3 days, about 4 days, about 5 days, about 6 days, or about 7 days from the administration; and
a maximum plasma concentration ($C_{max}$) in the subject in need thereof that is from about 50% to about 150%, from about 60% to about 140%, from about 70% to about 130%, from about 80% to about 120%, from about 90% to about 110%, from about 95% to about 105%, or from 98% to about 102% as compared to a comparable subject being administered with the β-lactam compound and probenecid in separate formulations.

In some embodiments, the administration results in a plasma concentration for the β-lactam compound having:
an area under the curve (AUC) that is higher in the subject in need thereof as compared to a comparable subject being administered with the β-lactam compound and probenecid in separate formulations by about 5% or greater, about 10% or greater, about 15% or greater, about 20% or greater, about 25% or greater, about 30% or greater, about 40% or greater, about 50% or greater, about 60% or greater, about 80% or greater, about 100% or greater, about 150% or greater, about 200% or greater, about 300% or greater, about 400% or greater, or about 500% or greater within about 30 minutes, about 1 hour, about 2 hours, about 3 hours, about 6 hours, about 12 hours, about 18 hours, about 1 day, about 2 days, about 3 days, about 4 days, about 5 days, about 6 days, or about 7 days from the administration; and a maximum plasma concentration ($C_{max}$) in the subject in need thereof that is substantially the same as compared to a comparable subject being administered with the β-lactam compound and probenecid in separate formulations.

In some embodiments, the administration results in a plasma concentration for the β-lactam compound having:

an area under the curve (AUC) that is higher in the subject in need thereof as compared to a comparable subject being administered with the β-lactam compound and probenecid without food (e.g., the comparable subject is fasted) by about 5% or greater, about 10% or greater, about 15% or greater, about 20% or greater, about 25% or greater, about 30% or greater, about 40% or greater, about 50% or greater, about 60% or greater, about 80% or greater, about 100% or greater, about 150% or greater, about 200% or greater, about 300% or greater, about 400% or greater, or about 500% or greater within about 30 minutes, about 1 hour, about 2 hours, about 3 hours, about 6 hours, about 12 hours, about 18 hours, about 1 day, about 2 days, about 3 days, about 4 days, about 5 days, about 6 days, or about 7 days from the administration.

In some embodiments, the administration results in a plasma concentration for the 0-lactam compound having:

an area under the curve (AUC) that is higher in the subject in need thereof as compared to a comparable subject being administered with the β-lactam compound and probenecid without food (e.g., the comparable subject is fasted) by about 5% or greater, about 10% or greater, about 15% or greater, about 20% or greater, about 25% or greater, about 30% or greater, about 40% or greater, about 50% or greater, about 60% or greater, about 80% or greater, about 100% or greater, about 150% or greater, about 200% or greater, about 300% or greater, about 400% or greater, or about 500% or greater within about 30 minutes, about 1 hour, about 2 hours, about 3 hours, about 6 hours, about 12 hours, about 18 hours, about 1 day, about 2 days, about 3 days, about 4 days, about 5 days, about 6 days, or about 7 days from the administration; and a maximum plasma concentration ($C_{max}$) in the subject in need thereof that is from about 50% to about 150%, from about 60% to about 140%, from about 70% to about 130%, from about 80% to about 120%, from about 90% to about 110%, from about 95% to about 105%, or from 98% to about 102% as compared to a comparable subject being administered with the β-lactam compound and probenecid without food (e.g., the comparable subject is fasted).

In some embodiments, the administration results in a plasma concentration for the β-lactam compound having:

an area under the curve (AUC) that is higher in the subject in need thereof as compared to a comparable subject being administered with the β-lactam compound and probenecid without food (e.g., the comparable subject is fasted) by about 5% or greater, about 10% or greater, about 15% or greater, about 20% or greater, about 25% or greater, about 30% or greater, about 40% or greater, about 50% or greater, about 60% or greater, about 80% or greater, about 100% or greater, about 150% or greater, about 200% or greater, about 300% or greater, about 400% or greater, or about 500% or greater within about 30 minutes, about 1 hour, about 2 hours, about 3 hours, about 6 hours, about 12 hours, about 18 hours, about 1 day, about 2 days, about 3 days, about 4 days, about 5 days, about 6 days, or about 7 days from the administration; and a maximum plasma concentration ($C_{max}$) in the subject in need thereof that is substantially the same as compared to a comparable subject being administered with the β-lactam compound and probenecid without food (e.g., the comparable subject is fasted).

In some embodiments, about 500±400 mg, about 500±300 mg, about 500±200 mg, about 500±100 mg, about 500±90 mg, about 500±80 mg, about 500±70 mg, about 500±60 mg, about 500±50 mg, about 500±40 mg, about 500±30 mg, about 500±20 mg, about 500±10 mg, or about 500±5 mg (e.g., about 500 mg) of the β-lactam compound (e.g., Compound III-2b) or the pharmaceutically acceptable salt and about 500±400 mg, about 500±300 mg, about 500±200 mg, about 500±100 mg, about 500±90 mg, about 500±80 mg, about 500±70 mg, about 500±60 mg, about 500±50 mg, about 500±40 mg, about 500±30 mg, about 500±20 mg, about 500±10 mg, or about 500±5 mg (e.g., about 500 mg) of the probenecid or the pharmaceutically acceptable salt are administered to the subject in need thereof by the same administration route, and the administration results in a plasma concentration for the β-lactam compound having:

an area under the curve (AUC) being from about 4325±3000 ng·h/mL, about 4325±2500 ng·h/mL, about 4325±2000 ng·h/mL, about 4325±1500 ng·h/mL, about 4325±1000 ng·h/mL, about 4325±900 ng·h/mL, about 4325±800 ng·h/mL, about 4325±700 ng·h/mL, about 4325±600 ng·h/mL, about 4325±500 ng·h/mL, about 4325±400 ng·h/mL, about 4325±300 ng·h/mL, about 4325±200 ng·h/mL, about 4325±100 ng·h/mL, about 4325±90 ng·h/mL, about 4325±80 ng·h/mL, about 4325±70 ng·h/mL, about 4325±60 ng·h/mL, about 4325±50 ng·h/mL, about 4325±40 ng·h/mL, about 4325±30 ng·h/mL, about 4325±20 ng·h/mL, or about 4325±10 ng·h/mL (e.g., about 4325 ng·h/mL) within about 1 day from the administration.

In some embodiments, about 500±400 mg, about 500±300 mg, about 500±200 mg, about 500±100 mg, about 500±90 mg, about 500±80 mg, about 500±70 mg, about 500±60 mg, about 500±50 mg, about 500±40 mg, about 500±30 mg, about 500±20 mg, about 500±10 mg, or about 500±5 mg (e.g., about 500 mg) of the β-lactam compound (e.g., Compound III-2b) or the pharmaceutically acceptable salt and about 500±400 mg, about 500±300 mg, about 500±200 mg, about 500±100 mg, about 500±90 mg, about 500±80 mg, about 500±70 mg, about 500±60 mg, about 500±50 mg, about 500±40 mg, about 500±30 mg, about 500±20 mg, about 500±10 mg, or about 500±5 mg (e.g., about 500 mg) of the probenecid or the pharmaceutically acceptable salt are administered to the subject in need thereof by the same administration route and with food (e.g., the subject is fed), and the administration results in a plasma concentration for the β-lactam compound having:

an area under the curve (AUC) being from about 6600±3000 ng·h/mL, about 6600±2500 ng·h/mL, about 6600±2000 ng·h/mL, about 6600±1500 ng·h/mL, about 6600±1000 ng·h/mL, about 6600±900 ng·h/mL, about 6600±800 ng·h/mL, about 6600±700 ng·h/mL, about 6600±600 ng·h/mL, about 6600±500 ng·h/mL, about 6600±400 ng·h/mL, about 6600±300 ng·h/mL, about 6600±200 ng·h/mL, about 6600±100 ng·h/mL, about 6600±90 ng·h/mL, about 6600±80 ng·h/mL, about 6600±70 ng·h/mL, about 6600±60 ng·h/mL, about 6600±50 ng·h/mL, about 6600±40 ng·h/mL, about 6600±30 ng·h/mL, about 6600±20 ng·h/mL, or about 6600±10 ng·h/mL (e.g., about 6600 ng·h/mL) within about 1 day from the administration.

In some embodiments, about 500±400 mg, about 500±300 mg, about 500±200 mg, about 500±100 mg, about 500±90 mg, about 500±80 mg, about 500±70 mg, about 500±60 mg, about 500±50 mg, about 500±40 mg, about 500±30 mg, about 500±20 mg, about 500±10 mg, or about 500±5 mg (e.g., about 500 mg) of the β-lactam compound (e.g., Compound III-2b) or the pharmaceutically acceptable salt and about 500±400 mg, about 500±300 mg, about 500±200 mg, about 500±100 mg, about 500±90 mg, about 500±80 mg, about 500±70 mg, about 500±60 mg, about 500±50 mg, about 500±40 mg, about 500±30 mg, about 500±20 mg, about 500±10 mg, or about 500±5 mg (e.g., about 500 mg) of the probenecid or the pharmaceutically acceptable salt are administered to the subject in need thereof in a co-formulation, and the administration results in a plasma concentration for the β-lactam compound having:
an area under the curve (AUC) being from about 5100±3000 ng·h/mL, about 5100±2500 ng·h/mL, about 5100±2000 ng·h/mL, about 5100±1500 ng·h/mL, about 5100±1000 ng·h/mL, about 5100±900 ng·h/mL, about 5100±800 ng·h/mL, about 5100±700 ng·h/mL, about 5100±600 ng·h/mL, about 5100±500 ng·h/mL, about 5100±400 ng·h/mL, about 5100±300 ng·h/mL, about 5100±200 ng·h/mL, about 5100±100 ng·h/mL, about 5100±90 ng·h/mL, about 5100±80 ng·h/mL, about 5100±70 ng·h/mL, about 5100±60 ng·h/mL, about 5100±50 ng·h/mL, about 5100±40 ng·h/mL, about 5100±30 ng·h/mL, about 5100±20 ng·h/mL, or about 5100±10 ng·h/mL (e.g., about 5100 ng·h/mL) within about 1 day from the administration.

In some embodiments, about 500±400 mg, about 500±300 mg, about 500±200 mg, about 500±100 mg, about 500±90 mg, about 500±80 mg, about 500±70 mg, about 500±60 mg, about 500±50 mg, about 500±40 mg, about 500±30 mg, about 500±20 mg, about 500±10 mg, or about 500±5 mg (e.g., about 500 mg) of the β-lactam compound (e.g., Compound III-2b) or the pharmaceutically acceptable salt and about 500±400 mg, about 500±300 mg, about 500±200 mg, about 500±100 mg, about 500±90 mg, about 500±80 mg, about 500±70 mg, about 500±60 mg, about 500±50 mg, about 500±40 mg, about 500±30 mg, about 500±20 mg, about 500±10 mg, or about 500±5 mg (e.g., about 500 mg) of the probenecid or the pharmaceutically acceptable salt are administered to the subject in need thereof in a co-formulation and with food (e.g., the subject is fed), and the administration results in a plasma concentration for the β-lactam compound having:
an area under the curve (AUC) being from about 7340±3000 ng·h/mL, about 7340±2500 ng·h/mL, about 7340±2000 ng·h/mL, about 7340±1500 ng·h/mL, about 7340±1000 ng·h/mL, about 7340±900 ng·h/mL, about 7340±800 ng·h/mL, about 7340±700 ng·h/mL, about 7340±600 ng·h/mL, about 7340±500 ng·h/mL, about 7340±400 ng·h/mL, about 7340±300 ng·h/mL, about 7340±200 ng·h/mL, about 7340±100 ng·h/mL, about 7340±90 ng·h/mL, about 7340±80 ng·h/mL, about 7340±70 ng·h/mL, about 7340±60 ng·h/mL, about 7340±50 ng·h/mL, about 7340±40 ng·h/mL, about 7340±30 ng·h/mL, about 7340±20 ng·h/mL, or about 7340±10 ng·h/mL (e.g., about 7340 ng·h/mL) within about 1 day from the administration.

In some embodiments, about 500 mg of the β-lactam compound or the pharmaceutically acceptable salt and about 500 mg of the probenecid or the pharmaceutically acceptable salt are administered to the subject in need thereof, and the administration results in a plasma concentration for the β-lactam compound having:
an area under the curve (AUC) being from about 4100 ng·h/mL to about 5500 ng·h/mL, from about 4200 ng·h/mL to about 5400 ng·h/mL, from about 4300 ng·h/mL to about 5300 ng·h/mL, from about 4400 ng·h/mL to about 5200 ng·h/mL, from about 4500 ng·h/mL to about 5100 ng·h/mL, from about 4650 ng·h/mL to about 5000 ng·h/mL, from about 4750 ng·h/mL to about 4900 ng·h/mL, or from about 4800 ng·h/mL to about 4850 ng·h/mL within about 12 hours from the administration; and
a maximum plasma concentration ($C_{max}$) being from about 1100 ng/mL to about 2500 ng/mL, from about 1200 ng/mL to about 2400 ng/mL, from about 1300 ng/mL to about 2300 ng/mL, from about 1400 ng/mL to about 2200 ng/mL, from about 1500 ng/mL to about 2100 ng/mL, from about 1650 ng/mL to about 2000 ng/mL, from about 1750 ng/mL to about 1900 ng/mL, or from about 1800 ng/mL to about 1850 ng/mL.

In some embodiments, about 500 mg of the β-lactam compound or the pharmaceutically acceptable salt and about 500 mg of the probenecid or the pharmaceutically acceptable salt are administered to the subject in need thereof, and the administration results in a plasma concentration for the β-lactam compound having:
an area under the curve (AUC) being from about 7000 ng·h/mL to about 8400 ng·h/mL, from about 7100 ng·h/mL to about 8300 ng·h/mL, from about 7200 ng·h/mL to about 8200 ng·h/mL, from about 7300 ng·h/mL to about 5100 ng·h/mL, from about 7450 ng·h/mL to about 8100 ng·h/mL, from about 7500 ng·h/mL to about 8050 ng·h/mL, or from about 7550 ng·h/mL to about 8000 ng·h/mL within about 12 hours from the administration; and
a maximum plasma concentration ($C_{max}$) being from about 2100 ng/mL to about 3300 ng/mL, from about 2200 ng/mL to about 3200 ng/mL, from about 2300 ng/mL to about 3100 ng/mL, from about 2400 ng/mL to about 3000 ng/mL, from about 2500 ng/mL to about 2900 ng/mL, from about 2550 ng/mL to about 2800 ng/mL, from about 2600 ng/mL to about 2750 ng/mL, or from about 2650 ng/mL to about 2700 ng/mL.

In some embodiments, the administration results in a plasma concentration for the β-lactam compound having an area under the curve (AUC) that is higher in the subject in need thereof as compared to a comparable subject being administered with the β-lactam compound and probenecid without food (e.g., the comparable subject is fasted).

In some embodiments, the administration results in a plasma concentration for the β-lactam compound having an area under the curve (AUC) that is higher in the subject in need thereof as compared to a comparable subject being administered with the β-lactam compound and probenecid without food (e.g., the comparable subject is fasted) by about 5% or greater, about 10% or greater, about 20% or greater, about 30% or greater, about 40% or greater, about 50% or greater, about 55% or greater, about 60% or greater, about 65% or greater, about 70% or greater, about 100% or greater, about 150% or greater, about 200% or greater, about 300% or greater, about 400% or greater, or about 500% or greater within about 30 minutes, about 1 hour, about 2 hours, about 3 hours, about 6 hours, about 12 hours, about 18 hours, about 1 day, about 2 days, about 3 days, about 4 days, about 5 days, about 6 days, or about 7 days from the administration.

In some embodiments, the administration results in a plasma concentration for the β-lactam compound having an area under the curve (AUC) that is higher in the subject in need thereof as compared to a comparable subject being administered with the β-lactam compound and probenecid without food (e.g., the comparable subject is fasted) about 50% or greater, about 55% or greater, about 60% or greater, about 65% or greater, or about 70% or greater within about 12 hours, about 18 hours, about 1 day, about 2 days, or about 3 days from the administration.

In some embodiments, the administration results in a plasma concentration for the β-lactam compound having an area under the curve (AUC) that is higher in the subject in need thereof as compared to a comparable subject being administered with the β-lactam compound and probenecid without food (e.g., the comparable subject is fasted) about 55% or greater, about 60% or greater, or about 65% or greater within about 12 hours, about 1 day, or about 2 days from the administration.

In some embodiments, the administration results in a plasma concentration for the β-lactam compound having an area under the curve (AUC) that is higher in the subject in need thereof as compared to a comparable subject being administered with the β-lactam compound and probenecid without food (e.g., the comparable subject is fasted) about 55% or greater, about 60% or greater, or about 65% or greater within about 12 hours from the administration.

In some embodiments, the administration results in a plasma concentration for the β-lactam compound having an area under the curve (AUC) that is higher in the subject in need thereof as compared to a comparable subject being administered with the β-lactam compound and probenecid without food (e.g., the comparable subject is fasted) about 55% or greater, about 60% or greater, or about 65% or greater within about 1 day from the administration.

In some embodiments, the administration results in a plasma concentration for the β-lactam compound having an area under the curve (AUC) that is higher in the subject in need thereof as compared to a comparable subject being administered with the β-lactam compound and probenecid without food (e.g., the comparable subject is fasted) about 55% or greater, about 60% or greater, or about 65% or greater within about 2 days from the administration.

In some embodiments, the administration results in a plasma concentration for the β-lactam compound having an area under the curve (AUC) that is higher in the subject in need thereof as compared to a comparable subject being administered with the β-lactam compound and probenecid without food (e.g., the comparable subject is fasted) by about 60% or greater within about 1 day from the administration.

In some embodiments, one or both of the AUC and $C_{max}$ of the plasma concentration for the β-lactam compound in the subject in need thereof is observed at a time being after about the first 24 hours of the administration.

In some embodiments, one or both of the AUC and $C_{max}$ of the plasma concentration for the β-lactam compound in the subject in need thereof is observed at a time being after about first 2 days and within about first 30 days, after about first 3 days and within about first 20 days, after about first 4 days and within about first 15 days, after about first 5 days and within about first 10 days, or after about first 6 days and within about first 8 days of the administration.

In some embodiments, one or both of the AUC and $C_{max}$ of the plasma concentration for the β-lactam compound in the subject in need thereof is observed at a time being about the 7th day of the administration.

In some embodiments, one or both of the AUC and $C_{max}$ of the plasma concentration for the β-lactam compound in the subject in need thereof is observed at a time being after about the first 24 hours of the administration, and being on or before about the 30th day, about the 20th day, about the 15th day, about the 10th day, about the 8th day, or about the 7th of the administration.

In some embodiments, one or both of the AUC and $C_{max}$ of the plasma concentration for the β-lactam compound in the comparable subject is lower at the end of the period of the time as compared to the first day of the administration, preferably, by an amount ranging from about 1% to about 60%, from about 3% to about 50%, from about 5% to about 40%, from about 8% to about 38%, or from about 10% to about 35%.

In some embodiments, one or both of the AUC and $C_{max}$ of the plasma concentration for the β-lactam compound is higher in the subject in need thereof at the end of the period of the time as compared to the comparable subject at the first day of the administration, preferably, by an amount ranging from about 2% to about 100%, from about 4% to about 80%, from about 6% to about 60%, from about 8% to about 40%, from about 10% to about 30%, from about 12% to about 25%, or from about 15% to about 20%.

In some embodiments, the resulted $C_{max}$ of the plasma concentration for the β-lactam compound in the comparable subject at the first day of the administration ranges from about 1.5 ng/mL to about 2.5 ng/mL, from about 1.6 ng/mL to about 2.4 ng/mL, from about 1.7 ng/mL to about 2.3 ng/mL, from about 1.8 ng/mL to about 2.2 ng/mL, or from about 1.9 ng/mL to about 2.1 ng/mL per mg of 3-lactam compound administered daily.

In some embodiments, the resulted $C_{max}$ of the plasma concentration for the β-lactam compound in the comparable subject at the first day of the administration is at about 2.0 ng/mL per mg of β-lactam compound administered daily.

In some embodiments, the resulted $C_{max}$ of the plasma concentration for the β-lactam compound in the comparable subject at the seventh day of the administration ranges from about 0.7 ng/mL to about 1.8 ng/mL, from about 0.8 ng/mL to about 1.7 ng/mL, from about 0.9 ng/mL to about 1.6 ng/mL, from about 1.0 ng/mL to about 1.5 ng/mL, from about 1.1 ng/mL to about 1.4 ng/mL, or from about 1.2 ng/mL to about 1.3 ng/mL per mg of 3-lactam compound administered daily.

In some embodiments, the resulted $C_{max}$ of the plasma concentration for the β-lactam compound in the comparable subject at the seventh day of the administration is at about 1.25 ng/mL per mg of 3-lactam compound administered daily.

In some embodiments, the resulted $C_{max}$ of the plasma concentration for the β-lactam compound in the subject in need thereof at the first day of the administration ranges from about 1.6 ng/mL to about 2.7 ng/mL, from about 1.7 ng/mL to about 2.6 ng/mL, from about 1.8 ng/mL to about 2.5 ng/mL, from about 1.9 ng/mL to about 2.4 ng/mL, from about 2.0 ng/mL to about 2.3 ng/mL, or from about 2.1 ng/mL to about 2.2 ng/mL per mg of 3-lactam compound administered daily.

In some embodiments, the resulted $C_{max}$ of the plasma concentration for the β-lactam compound in the subject in need thereof at the first day of the administration is at about 2.15 ng/mL per mg of 3-lactam compound administered daily.

In some embodiments, the resulted $C_{max}$ of the plasma concentration for the β-lactam compound in the subject in need thereof at the seventh day of the administration ranges from about 1.6 ng/mL to about 2.7 ng/mL, from about 1.7 ng/mL to about 2.6 ng/mL, from about 1.8 ng/mL to about 2.5 ng/mL, from about 1.9 ng/mL to about 2.4 ng/mL, from about 2.0 ng/mL to about 2.3 ng/mL, or from about 2.1 ng/mL to about 2.2 ng/mL per mg of 3-lactam compound administered daily.

In some embodiments, the resulted $C_{max}$ of the plasma concentration for the β-lactam compound in the subject in need thereof at the seventh day of the administration is at about 2.15 ng/mL per mg of 3-lactam compound administered daily.

In some embodiments, the resulted $C_{max}$ of the plasma concentration for the β-lactam compound in the comparable subject at the first day of the administration ranges from about 1.2 ng/mL to about 2.2 ng/mL, from about 1.3 ng/mL to about 2.1 ng/mL, from about 1.4 ng/mL to about 2.0 ng/mL, from about 1.5 ng/mL to about 1.9 ng/mL, or from about 1.6 ng/mL to about 1.8 ng/mL per mg of 3-lactam compound administered daily.

In some embodiments, the resulted $C_{max}$ of the plasma concentration for the β-lactam compound in the comparable subject at the first day of the administration is at about 1.7 ng/mL per mg of β-lactam compound administered daily.

In some embodiments, the resulted $C_{max}$ of the plasma concentration for the β-lactam compound in the comparable subject at the seventh day of the administration ranges from about 0.8 ng/mL to about 1.8 ng/mL, from about 0.9 ng/mL to about 1.7 ng/mL, from about 1.0 ng/mL to about 1.6 ng/mL, from about 1.1 ng/mL to about 1.5 ng/mL, or from about 1.2 ng/mL to about 1.4 ng/mL per mg of 3-lactam compound administered daily.

In some embodiments, the resulted $C_{max}$ of the plasma concentration for the β-lactam compound in the comparable subject at the seventh day of the administration is at about 1.3 ng/mL per mg of β-lactam compound administered daily.

In some embodiments, the resulted $C_{max}$ of the plasma concentration for the β-lactam compound in the subject in need thereof at the first day of the administration ranges from about 1.2 ng/mL to about 2.2 ng/mL, from about 1.3 ng/mL to about 2.1 ng/mL, from about 1.4 ng/mL to about 2.0 ng/mL, from about 1.5 ng/mL to about 1.9 ng/mL, or from about 1.6 ng/mL to about 1.8 ng/mL per mg of 3-lactam compound administered daily.

In some embodiments, the resulted $C_{max}$ of the plasma concentration for the β-lactam compound in the subject in need thereof at the first day of the administration is at about 1.7 ng/mL per mg of β-lactam compound administered daily.

In some embodiments, the resulted $C_{max}$ of the plasma concentration for the β-lactam compound in the subject in need thereof at the seventh day of the administration ranges from about 0.9 ng/mL to about 2.0 ng/mL, from about 1.0 ng/mL to about 1.9 ng/mL, from about 1.1 ng/mL to about 1.8 ng/mL, from about 1.2 ng/mL to about 1.7 ng/mL, from about 1.3 ng/mL to about 1.6 ng/mL, or from about 1.4 ng/mL to about 1.5 ng/mL per mg of 3-lactam compound administered daily.

In some embodiments, the resulted $C_{max}$ of the plasma concentration for the β-lactam compound in the subject in need thereof at the seventh day of the administration is at about 1.45 ng/mL per mg of 3-lactam compound administered daily.

In some embodiments, the resulted AUC of the plasma concentration for the β-lactam compound in the comparable subject at the first day of the administration from about 2.5 hr*ng/mL to about 3.2 hr*ng/mL, from about 2.6 hr*ng/mL to about 3.1 hr*ng/mL, from about 2.7 hr*ng/mL to about 3.0 hr*ng/mL, or from about 2.8 hr*ng/mL to about 2.9 hr*ng/mL per mg of 3-lactam compound administered daily.

In some embodiments, the resulted AUC of the plasma concentration for the β-lactam compound in the comparable subject at the first day of the administration is at about 2.85 hr*ng/mL per mg of 3-lactam compound administered daily.

In some embodiments, the resulted AUC of the plasma concentration for the β-lactam compound in the comparable subject at the seventh day of the administration ranges from about 1.6 hr*ng/mL to about 2.2 hr*ng/mL, from about 1.7 hr*ng/mL to about 2.1 hr*ng/mL, or from about 1.8 hr*ng/mL to about 2.0 hr*ng/mL per mg of β-lactam compound administered daily.

In some embodiments, the resulted AUC of the plasma concentration for the β-lactam compound in the comparable subject at the seventh day of the administration is at about 1.9 hr*ng/mL per mg of 3-lactam compound administered daily.

In some embodiments, the resulted AUC of the plasma concentration for the β-lactam compound in the subject in need thereof at the first day of the administration ranges from about 3.9 hr*ng/mL to about 4.5 hr*ng/mL, from about 4.0 hr*ng/mL to about 4.4 hr*ng/mL, or from about 4.1 hr*ng/mL to about 4.3 hr*ng/mL per mg of β-lactam compound administered daily.

In some embodiments, the resulted AUC of the plasma concentration for the β-lactam compound in the subject in need thereof at the first day of the administration is at about 4.2 hr*ng/mL per mg of 3-lactam compound administered daily.

In some embodiments, the resulted AUC of the plasma concentration for the β-lactam compound in the subject in need thereof at the seventh day of the administration ranges from about 4.1 hr*ng/mL to about 4.7 hr*ng/mL, from about 4.2 hr*ng/mL to about 4.6 hr*ng/mL, or from about 4.3 hr*ng/mL to about 4.5 hr*ng/mL per mg of β-lactam compound administered daily.

In some embodiments, the resulted AUC of the plasma concentration for the β-lactam compound in the subject in need thereof at the seventh day of the administration the resulted AUC is at about 4.4 hr*ng/mL per mg of β-lactam compound administered daily.

In some embodiments, the resulted AUC of the plasma concentration for the β-lactam compound in the comparable subject at the first day of the administration ranges from about 3.2 hr*ng/mL to about 4.0 hr*ng/mL, from about 3.3 hr*ng/mL to about 3.9 hr*ng/mL, from about 3.4 hr*ng/mL to about 3.8 hr*ng/mL, or from about 3.5 hr*ng/mL to about 3.7 hr*ng/mL per mg of 3-lactam compound administered daily.

In some embodiments, the resulted AUC of the plasma concentration for the β-lactam compound in the comparable subject at the first day of the administration is at about 3.6 hr*ng/mL per mg of β-lactam compound administered daily.

In some embodiments, the resulted AUC of the plasma concentration for the β-lactam compound in the comparable subject at the seventh day of the administration ranges from about 2.2 hr*ng/mL to about 3.1 hr*ng/mL, from about 2.3 hr*ng/mL to about 3.0 hr*ng/mL, from about 2.4 hr*ng/mL to about 2.9 hr*ng/mL, from about 2.5 hr*ng/mL to about 2.8 hr*ng/mL, or from about 2.6 hr*ng/mL to about 2.7 hr*ng/mL per mg of β-lactam compound administered daily.

In some embodiments, the resulted AUC of the plasma concentration for the β-lactam compound in the comparable subject at the seventh day of the administration is at about 2.65 hr*ng/mL per mg of 3-lactam compound administered daily.

In some embodiments, the resulted AUC of the plasma concentration for the β-lactam compound in the subject in need thereof at the first day of the administration ranges from about 3.4 hr*ng/mL to about 4.3 hr*ng/mL, from about 3.5 hr*ng/mL to about 4.2 hr*ng/mL, from about 3.6 hr*ng/mL to about 4.1 hr*ng/mL, from about 3.7 hr*ng/mL to about 4.0 hr*ng/mL, or from about 3.8 hr*ng/mL to about 3.9 hr*ng/mL per mg of β-lactam compound administered daily.

In some embodiments, the resulted AUC of the plasma concentration for the β-lactam compound in the subject in need thereof at the first day of the administration is at about 3.85 hr*ng/mL per mg of 3-lactam compound administered daily.

In some embodiments, the resulted AUC of the plasma concentration for the β-lactam compound in the subject in need thereof at the seventh day of the administration ranges from about 3.9 hr*ng/mL to about 4.7 hr*ng/mL, from about 4.0 hr*ng/mL to about 4.6 hr*ng/mL, from about 4.1 hr*ng/mL to about 4.4 hr*ng/mL, from about 4.2 hr*ng/mL to about 4.3 hr*ng/mL per mg of β-lactam compound administered daily.

In some embodiments, the resulted AUC of the plasma concentration for the β-lactam compound in the subject in need thereof at the seventh day of the administration is at about 4.25 hr*ng/mL per mg of 3-lactam compound administered daily.

In some embodiments, the resulted $C_{max}$ of the plasma concentration for the β-lactam compound in the comparable subject at the first day of the administration is at about 0.5 ng/mL, about 0.55 ng/mL, about 0.6 ng/mL, about 0.65 ng/mL, about 0.7 ng/mL, about 0.75 ng/mL, about 0.8 ng/mL, about 0.85 ng/mL, about 0.9 ng/mL, about 0.95 ng/mL, about 1 ng/mL, about 1.05 ng/mL, about 1.1 ng/mL, about 1.15 ng/mL, about 1.2 ng/mL, about 1.25 ng/mL, about 1.3 ng/mL, about 1.35 ng/mL, about 1.4 ng/mL, about 1.45 ng/mL, about 1.5 ng/mL, about 1.55 ng/mL, about 1.6 ng/mL, about 1.65 ng/mL, about 1.7 ng/mL, about 1.75 ng/mL, about 1.8 ng/mL, about 1.85 ng/mL, about 1.9 ng/mL, about 1.95 ng/mL, about 2 ng/mL, about 2.05 ng/mL, about 2.1 ng/mL, about 2.15 ng/mL, about 2.2 ng/mL, about 2.25 ng/mL, about 2.3 ng/mL, about 2.35 ng/mL, about 2.4 ng/mL, about 2.45 ng/mL, about 2.5 ng/mL, about 2.55 ng/mL, about 2.6 ng/mL, about 2.65 ng/mL, about 2.7 ng/mL, about 2.75 ng/mL, about 2.8 ng/mL, about 2.85 ng/mL, about 2.9 ng/mL, about 2.95 ng/mL, about 3 ng/mL, about 3.1 ng/mL, about 3.2 ng/mL, about 3.3 ng/mL, about 3.4 ng/mL, about 3.5 ng/mL, about 3.6 ng/mL, about 3.7 ng/mL, about 3.8 ng/mL, about 3.9 ng/mL, about 4 ng/mL, about 4.1 ng/mL, about 4.2 ng/mL, about 4.3 ng/mL, about 4.4 ng/mL, about 4.5 ng/mL, about 4.6 ng/mL, about 4.7 ng/mL, about 4.8 ng/mL, about 4.9 ng/mL, about 5 ng/mL, about 5.5 ng/mL, about 6 ng/mL, about 6.5 ng/mL, about 7 ng/mL, about 7.5 ng/mL, about 8 ng/mL, about 8.5 ng/mL, about 9 ng/mL, about 9.5 ng/mL, about 10 ng/mL, about 11 ng/mL, about 12 ng/mL, about 13 ng/mL, about 14 ng/mL, about 15 ng/mL, about 16 ng/mL, about 17 ng/mL, about 18 ng/mL, about 19 ng/mL, about 20 ng/mL, about 25 ng/mL, about 30 ng/mL, about 35 ng/mL, about 40 ng/mL, about 45 ng/mL, about 50 ng/mL, about 60 ng/mL, about 70 ng/mL, about 80 ng/mL, about 90 ng/mL, or about 100 ng/mL per mg of 3-lactam compound administered daily.

In some embodiments, the resulted $C_{max}$ of the plasma concentration for the β-lactam compound in the comparable subject at the seventh day of the administration is at about 0.5 ng/mL, about 0.55 ng/mL, about 0.6 ng/mL, about 0.65 ng/mL, about 0.7 ng/mL, about 0.75 ng/mL, about 0.8 ng/mL, about 0.85 ng/mL, about 0.9 ng/mL, about 0.95 ng/mL, about 1 ng/mL, about 1.05 ng/mL, about 1.1 ng/mL, about 1.15 ng/mL, about 1.2 ng/mL, about 1.25 ng/mL, about 1.3 ng/mL, about 1.35 ng/mL, about 1.4 ng/mL, about 1.45 ng/mL, about 1.5 ng/mL, about 1.55 ng/mL, about 1.6 ng/mL, about 1.65 ng/mL, about 1.7 ng/mL, about 1.75 ng/mL, about 1.8 ng/mL, about 1.85 ng/mL, about 1.9 ng/mL, about 1.95 ng/mL, about 2 ng/mL, about 2.05 ng/mL, about 2.1 ng/mL, about 2.15 ng/mL, about 2.2 ng/mL, about 2.25 ng/mL, about 2.3 ng/mL, about 2.35 ng/mL, about 2.4 ng/mL, about 2.45 ng/mL, about 2.5 ng/mL, about 2.55 ng/mL, about 2.6 ng/mL, about 2.65 ng/mL, about 2.7 ng/mL, about 2.75 ng/mL, about 2.8 ng/mL, about 2.85 ng/mL, about 2.9 ng/mL, about 2.95 ng/mL, about 3 ng/mL, about 3.1 ng/mL, about 3.2 ng/mL, about 3.3 ng/mL, about 3.4 ng/mL, about 3.5 ng/mL, about 3.6 ng/mL, about 3.7 ng/mL, about 3.8 ng/mL, about 3.9 ng/mL, about 4 ng/mL, about 4.1 ng/mL, about 4.2 ng/mL, about 4.3 ng/mL, about 4.4 ng/mL, about 4.5 ng/mL, about 4.6 ng/mL, about 4.7 ng/mL, about 4.8 ng/mL, about 4.9 ng/mL, about 5 ng/mL, about 5.5 ng/mL, about 6 ng/mL, about 6.5 ng/mL, about 7 ng/mL, about 7.5 ng/mL, about 8 ng/mL, about 8.5 ng/mL, about 9 ng/mL, about 9.5 ng/mL, about 10 ng/mL, about 11 ng/mL, about 12 ng/mL, about 13 ng/mL, about 14 ng/mL, about 15 ng/mL, about 16 ng/mL, about 17 ng/mL, about 18 ng/mL, about 19 ng/mL, about 20 ng/mL, about 25 ng/mL, about 30 ng/mL, about 35 ng/mL, about 40 ng/mL, about 45 ng/mL, about 50 ng/mL, about 60 ng/mL, about 70 ng/mL, about 80 ng/mL, about 90 ng/mL, or about 100 ng/mL per mg of β-lactam compound administered daily, or any range therebetween.

In some embodiments, the resulted $C_{max}$ of the plasma concentration for the β-lactam compound in the subject in need thereof at the first day of the administration is at about 0.5 ng/mL, about 0.55 ng/mL, about 0.6 ng/mL, about 0.65 ng/mL, about 0.7 ng/mL, about 0.75 ng/mL, about 0.8 ng/mL, about 0.85 ng/mL, about 0.9 ng/mL, about 0.95 ng/mL, about 1 ng/mL, about 1.05 ng/mL, about 1.1 ng/mL, about 1.15 ng/mL, about 1.2 ng/mL, about 1.25 ng/mL, about 1.3 ng/mL, about 1.35 ng/mL, about 1.4 ng/mL, about 1.45 ng/mL, about 1.5 ng/mL, about 1.55 ng/mL, about 1.6 ng/mL, about 1.65 ng/mL, about 1.7 ng/mL, about 1.75 ng/mL, about 1.8 ng/mL, about 1.85 ng/mL, about 1.9 ng/mL, about 1.95 ng/mL, about 2 ng/mL, about 2.05 ng/mL, about 2.1 ng/mL, about 2.15 ng/mL, about 2.2 ng/mL, about 2.25 ng/mL, about 2.3 ng/mL, about 2.35 ng/mL, about 2.4 ng/mL, about 2.45 ng/mL, about 2.5 ng/mL, about 2.55 ng/mL, about 2.6 ng/mL, about 2.65 ng/mL, about 2.7 ng/mL, about 2.75 ng/mL, about 2.8 ng/mL, about 2.85 ng/mL, about 2.9 ng/mL, about 2.95 ng/mL, about 3 ng/mL, about 3.1 ng/mL, about 3.2 ng/mL, about 3.3 ng/mL, about 3.4 ng/mL, about 3.5 ng/mL, about 3.6 ng/mL, about 3.7 ng/mL, about 3.8 ng/mL, about 3.9 ng/mL, about 4 ng/mL, about 4.1 ng/mL, about 4.2 ng/mL, about 4.3 ng/mL, about 4.4 ng/mL, about 4.5 ng/mL, about 4.6 ng/mL, about 4.7 ng/mL, about 4.8 ng/mL, about 4.9 ng/mL, about 5 ng/mL, about 5.5 ng/mL, about 6 ng/mL, about 6.5 ng/mL, about 7 ng/mL, about 7.5 ng/mL, about 8 ng/mL, about 8.5 ng/mL, about 9 ng/mL, about 9.5 ng/mL, about 10 ng/mL, about 11 ng/mL, about 12 ng/mL, about 13 ng/mL, about 14 ng/mL, about 15 ng/mL, about 16 ng/mL, about 17 ng/mL, about 18 ng/mL, about 19 ng/mL, about 20 ng/mL, about 25 ng/mL, about 30 ng/mL, about 35 ng/mL, about 40 ng/mL, about 45 ng/mL, about 50 ng/mL, about 60 ng/mL, about 70 ng/mL, about 80 ng/mL, about 90 ng/mL, or about 100 ng/mL per mg of β-lactam compound administered daily, or any range therebetween.

In some embodiments, the resulted $C_{max}$ of the plasma concentration for the β-lactam compound in the subject in need thereof at the seventh day of the administration is at about 0.5 ng/mL, about 0.55 ng/mL, about 0.6 ng/mL, about 0.65 ng/mL, about 0.7 ng/mL, about 0.75 ng/mL, about 0.8 ng/mL, about 0.85 ng/mL, about 0.9 ng/mL, about 0.95 ng/mL, about 1 ng/mL, about 1.05 ng/mL, about 1.1 ng/mL, about 1.15 ng/mL, about 1.2 ng/mL, about 1.25 ng/mL, about 1.3 ng/mL, about 1.35 ng/mL, about 1.4 ng/mL, about 1.45 ng/mL, about 1.5 ng/mL, about 1.55 ng/mL, about 1.6 ng/mL, about 1.65 ng/mL, about 1.7 ng/mL, about 1.75 ng/mL, about 1.8 ng/mL, about 1.85 ng/mL, about 1.9 ng/mL, about 1.95 ng/mL, about 2 ng/mL, about 2.05 ng/mL, about 2.1 ng/mL, about 2.15 ng/mL, about 2.2 ng/mL, about 2.25 ng/mL, about 2.3 ng/mL, about 2.35 ng/mL, about 2.4 ng/mL, about 2.45 ng/mL, about 2.5 ng/mL, about 2.55 ng/mL, about 2.6 ng/mL, about 2.65 ng/mL, about 2.7 ng/mL, about 2.75 ng/mL, about 2.8 ng/mL, about 2.85 ng/mL, about 2.9 ng/mL, about 2.95 ng/mL, about 3 ng/mL, about 3.1 ng/mL, about 3.2 ng/mL, about 3.3 ng/mL, about 3.4 ng/mL, about 3.5 ng/mL, about 3.6 ng/mL, about 3.7 ng/mL, about 3.8 ng/mL, about 3.9 ng/mL, about 4 ng/mL, about 4.1 ng/mL, about 4.2 ng/mL, about 4.3 ng/mL, about 4.4 ng/mL, about 4.5 ng/mL, about 4.6 ng/mL, about 4.7 ng/mL, about 4.8 ng/mL, about 4.9 ng/mL, about 5 ng/mL, about 5.5 ng/mL, about 6 ng/mL, about 6.5 ng/mL, about 7 ng/mL, about 7.5 ng/mL, about 8 ng/mL, about 8.5 ng/mL, about 9 ng/mL, about 9.5 ng/mL, about 10 ng/mL, about 11 ng/mL, about 12 ng/mL, about 13 ng/mL, about 14 ng/mL, about 15 ng/mL, about 16 ng/mL, about 17 ng/mL, about 18 ng/mL, about 19 ng/mL, about 20 ng/mL, about 25 ng/mL, about 30 ng/mL, about 35 ng/mL, about 40 ng/mL, about 45 ng/mL, about 50 ng/mL, about 60 ng/mL, about 70 ng/mL, about 80 ng/mL, about 90 ng/mL, or about 100 ng/mL per mg of β-lactam compound administered daily, or any range therebetween.

In some embodiments, the resulted AUC of the plasma concentration for the β-lactam compound in the comparable subject at the first day of the administration is at about 0.5 hr*ng/mL, about 0.55 hr*ng/mL, about 0.6 hr*ng/mL, about 0.65 hr*ng/mL, about 0.7 hr*ng/mL, about 0.75 hr*ng/mL, about 0.8 hr*ng/mL, about 0.85 hr*ng/mL, about 0.9 hr*ng/mL, about 0.95 hr*ng/mL, about 1 hr*ng/mL, about 1.05 hr*ng/mL, about 1.1 hr*ng/mL, about 1.15 hr*ng/mL, about 1.2 hr*ng/mL, about 1.25 hr*ng/mL, about 1.3 hr*ng/mL, about 1.35 hr*ng/mL, about 1.4 hr*ng/mL, about 1.45 hr*ng/mL, about 1.5 hr*ng/mL, about 1.55 hr*ng/mL, about 1.6 hr*ng/mL, about 1.65 hr*ng/mL, about 1.7 hr*ng/mL, about 1.75 hr*ng/mL, about 1.8 hr*ng/mL, about 1.85 hr*ng/mL, about 1.9 hr*ng/mL, about 1.95 hr*ng/mL, about 2 hr*ng/mL, about 2.05 hr*ng/mL, about 2.1 hr*ng/mL, about 2.15 hr*ng/mL, about 2.2 hr*ng/mL, about 2.25 hr*ng/mL, about 2.3 hr*ng/mL, about 2.35 hr*ng/mL, about 2.4 hr*ng/mL, about 2.45 hr*ng/mL, about 2.5 hr*ng/mL, about 2.55 hr*ng/mL, about 2.6 hr*ng/mL, about 2.65 hr*ng/mL, about 2.7 hr*ng/mL, about 2.75 hr*ng/mL, about 2.8 hr*ng/mL, about 2.85 hr*ng/mL, about 2.9 hr*ng/mL, about 2.95 hr*ng/mL, about 3 hr*ng/mL, about 3.1 hr*ng/mL, about 3.2 hr*ng/mL, about 3.3 hr*ng/mL, about 3.4 hr*ng/mL, about 3.5 hr*ng/mL, about 3.6 hr*ng/mL, about 3.7 hr*ng/mL, about 3.8 hr*ng/mL, about 3.9 hr*ng/mL, about 4 hr*ng/mL, about 4.1 hr*ng/mL, about 4.2 hr*ng/mL, about 4.3 hr*ng/mL, about 4.4 hr*ng/mL, about 4.5 hr*ng/mL, about 4.6 hr*ng/mL, about 4.7 hr*ng/mL, about 4.8 hr*ng/mL, about 4.9 hr*ng/mL, about 5 hr*ng/mL, about 5.5 hr*ng/mL, about 6 hr*ng/mL, about 6.5 hr*ng/mL, about 7 hr*ng/mL, about 7.5 hr*ng/mL, about 8 hr*ng/mL, about 8.5 hr*ng/mL, about 9 hr*ng/mL, about 9.5 hr*ng/mL, about 10 hr*ng/mL, about 11 hr*ng/mL, about 12 hr*ng/mL, about 13 hr*ng/mL, about 14 hr*ng/mL, about 15 hr*ng/mL, about 16 hr*ng/mL, about 17 hr*ng/mL, about 18 hr*ng/mL, about 19 hr*ng/mL, about 20 hr*ng/mL, about 25 hr*ng/mL, about 30 hr*ng/mL, about 35 hr*ng/mL, about 40 hr*ng/mL, about 45 hr*ng/mL, about 50 hr*ng/mL, about 60 hr*ng/mL, about 70 hr*ng/mL, about 80 hr*ng/mL, about 90 hr*ng/mL, or about 100 hr*ng/mL per mg of β-lactam compound administered daily, or any range therebetween.

In some embodiments, the resulted AUC of the plasma concentration for the β-lactam compound in the comparable subject at the seventh day of the administration is at about 0.5 hr*ng/mL, about 0.55 hr*ng/mL, about 0.6 hr*ng/mL, about 0.65 hr*ng/mL, about 0.7 hr*ng/mL, about 0.75 hr*ng/mL, about 0.8 hr*ng/mL, about 0.85 hr*ng/mL, about 0.9 hr*ng/mL, about 0.95 hr*ng/mL, about 1 hr*ng/mL, about 1.05 hr*ng/mL, about 1.1 hr*ng/mL, about 1.15 hr*ng/mL, about 1.2 hr*ng/mL, about 1.25 hr*ng/mL, about 1.3 hr*ng/mL, about 1.35 hr*ng/mL, about 1.4 hr*ng/mL, about 1.45 hr*ng/mL, about 1.5 hr*ng/mL, about 1.55 hr*ng/mL, about 1.6 hr*ng/mL, about 1.65 hr*ng/mL, about 1.7 hr*ng/mL, about 1.75 hr*ng/mL, about 1.8 hr*ng/mL, about 1.85 hr*ng/mL, about 1.9 hr*ng/mL, about 1.95 hr*ng/mL, about 2 hr*ng/mL, about 2.05 hr*ng/mL, about 2.1 hr*ng/mL, about 2.15 hr*ng/mL, about 2.2 hr*ng/mL, about 2.25 hr*ng/mL, about 2.3 hr*ng/mL, about 2.35 hr*ng/mL, about 2.4 hr*ng/mL, about 2.45 hr*ng/mL, about 2.5 hr*ng/mL, about 2.55 hr*ng/mL, about 2.6 hr*ng/mL, about 2.65 hr*ng/mL, about 2.7 hr*ng/mL, about 2.75 hr*ng/mL, about 2.8 hr*ng/mL, about 2.85 hr*ng/mL, about 2.9 hr*ng/mL, about 2.95 hr*ng/mL, about 3 hr*ng/mL, about 3.1 hr*ng/mL, about 3.2 hr*ng/mL, about 3.3 hr*ng/mL, about 3.4 hr*ng/mL, about 3.5 hr*ng/mL, about 3.6 hr*ng/mL, about 3.7 hr*ng/mL, about 3.8 hr*ng/mL, about 3.9 hr*ng/mL, about 4 hr*ng/mL, about 4.1 hr*ng/mL, about 4.2 hr*ng/mL, about 4.3 hr*ng/mL, about 4.4 hr*ng/mL, about 4.5 hr*ng/mL, about 4.6 hr*ng/mL, about 4.7 hr*ng/mL, about 4.8 hr*ng/mL, about 4.9 hr*ng/mL, about 5 hr*ng/mL, about 5.5 hr*ng/mL, about 6 hr*ng/mL, about 6.5 hr*ng/mL, about 7 hr*ng/mL, about 7.5 hr*ng/mL, about 8 hr*ng/mL, about 8.5 hr*ng/mL, about 9 hr*ng/mL, about 9.5 hr*ng/mL, about 10 hr*ng/mL, about 11 hr*ng/mL, about 12 hr*ng/mL, about 13 hr*ng/mL, about 14 hr*ng/mL, about 15 hr*ng/mL, about 16 hr*ng/mL, about 17 hr*ng/mL, about 18 hr*ng/mL, about 19 hr*ng/mL, about 20 hr*ng/mL, about 25 hr*ng/mL, about 30 hr*ng/mL, about 35 hr*ng/mL, about 40 hr*ng/mL, about 45 hr*ng/mL, about 50 hr*ng/mL, about 60 hr*ng/mL, about 70 hr*ng/mL, about 80 hr*ng/mL, about 90 hr*ng/mL, or about 100 hr*ng/mL per mg of β-lactam compound administered daily, or any range therebetween.

In some embodiments, the resulted AUC of the plasma concentration for the β-lactam compound in the subject in need thereof at the first day of the administration is at about 0.5 hr*ng/mL, about 0.55 hr*ng/mL, about 0.6 hr*ng/mL, about 0.65 hr*ng/mL, about 0.7 hr*ng/mL, about 0.75 hr*ng/mL, about 0.8 hr*ng/mL, about 0.85 hr*ng/mL, about 0.9 hr*ng/mL, about 0.95 hr*ng/mL, about 1 hr*ng/mL, about 1.05 hr*ng/mL, about 1.1 hr*ng/mL, about 1.15 hr*ng/mL, about 1.2 hr*ng/mL, about 1.25 hr*ng/mL, about 1.3 hr*ng/mL, about 1.35 hr*ng/mL, about 1.4 hr*ng/mL, about 1.45 hr*ng/mL, about 1.5 hr*ng/mL, about 1.55 hr*ng/mL, about 1.6 hr*ng/mL, about 1.65 hr*ng/mL, about 1.7 hr*ng/mL, about 1.75 hr*ng/mL, about 1.8 hr*ng/mL, about 1.85 hr*ng/mL, about 1.9 hr*ng/mL, about 1.95 hr*ng/mL, about 2 hr*ng/mL, about 2.05 hr*ng/mL, about 2.1 hr*ng/mL, about 2.15 hr*ng/mL, about 2.2 hr*ng/mL, about 2.25 hr*ng/mL, about 2.3 hr*ng/mL, about 2.35 hr*ng/mL, about 2.4 hr*ng/mL, about 2.45 hr*ng/mL, about 2.5 hr*ng/mL, about 2.55 hr*ng/mL, about 2.6 hr*ng/mL, about 2.65 hr*ng/mL, about 2.7 hr*ng/mL, about 2.75 hr*ng/mL, about 2.8 hr*ng/mL, about 2.85 hr*ng/mL, about 2.9 hr*ng/mL, about 2.95 hr*ng/mL, about 3 hr*ng/mL, about 3.1 hr*ng/mL, about 3.2 hr*ng/mL, about 3.3 hr*ng/mL, about 3.4 hr*ng/mL, about 3.5 hr*ng/mL, about 3.6 hr*ng/mL, about 3.7 hr*ng/mL, about 3.8 hr*ng/mL, about 3.9 hr*ng/mL, about 4 hr*ng/mL, about 4.1 hr*ng/mL, about 4.2 hr*ng/mL, about 4.3 hr*ng/mL, about 4.4 hr*ng/mL, about 4.5 hr*ng/mL, about 4.6 hr*ng/mL, about 4.7 hr*ng/mL, about 4.8 hr*ng/mL, about 4.9 hr*ng/mL, about 5 hr*ng/mL, about 5.5 hr*ng/mL, about 6 hr*ng/mL, about 6.5 hr*ng/mL, about 7 hr*ng/mL, about 7.5 hr*ng/mL, about 8 hr*ng/mL, about 8.5 hr*ng/mL, about 9 hr*ng/mL, about 9.5 hr*ng/mL, about 10 hr*ng/mL, about 11 hr*ng/mL, about 12 hr*ng/mL, about 13 hr*ng/mL, about 14 hr*ng/mL, about 15 hr*ng/mL, about 16 hr*ng/mL, about 17 hr*ng/mL, about 18 hr*ng/mL, about 19 hr*ng/mL, about 20 hr*ng/mL, about 25 hr*ng/mL, about 30 hr*ng/mL, about 35 hr*ng/mL, about 40 hr*ng/mL, about 45 hr*ng/mL, about 50 hr*ng/mL, about 60 hr*ng/mL, about 70 hr*ng/mL, about 80 hr*ng/mL, about 90 hr*ng/mL, or about 100 hr*ng/mL per mg of β-lactam compound administered daily, or any range therebetween.

In some embodiments, the resulted AUC of the plasma concentration for the β-lactam compound in the subject in need thereof at the seventh day of the administration is at about 0.5 hr*ng/mL, about 0.55 hr*ng/mL, about 0.6 hr*ng/mL, about 0.65 hr*ng/mL, about 0.7 hr*ng/mL, about 0.75 hr*ng/mL, about 0.8 hr*ng/mL, about 0.85 hr*ng/mL, about 0.9 hr*ng/mL, about 0.95 hr*ng/mL, about 1 hr*ng/mL, about 1.05 hr*ng/mL, about 1.1 hr*ng/mL, about 1.15 hr*ng/mL, about 1.2 hr*ng/mL, about 1.25 hr*ng/mL, about 1.3 hr*ng/mL, about 1.35 hr*ng/mL, about 1.4 hr*ng/mL, about 1.45 hr*ng/mL, about 1.5 hr*ng/mL, about 1.55 hr*ng/mL, about 1.6 hr*ng/mL, about 1.65 hr*ng/mL, about 1.7 hr*ng/mL, about 1.75 hr*ng/mL, about 1.8 hr*ng/mL, about 1.85 hr*ng/mL, about 1.9 hr*ng/mL, about 1.95 hr*ng/mL, about 2 hr*ng/mL, about 2.05 hr*ng/mL, about 2.1 hr*ng/mL, about 2.15 hr*ng/mL, about 2.2 hr*ng/mL, about 2.25 hr*ng/mL, about 2.3 hr*ng/mL, about 2.35 hr*ng/mL, about 2.4 hr*ng/mL, about 2.45 hr*ng/mL, about 2.5 hr*ng/mL, about 2.55 hr*ng/mL, about 2.6 hr*ng/mL, about 2.65 hr*ng/mL, about 2.7 hr*ng/mL, about 2.75 hr*ng/mL, about 2.8 hr*ng/mL, about 2.85 hr*ng/mL, about 2.9 hr*ng/mL, about 2.95 hr*ng/mL, about 3 hr*ng/mL, about 3.1 hr*ng/mL, about 3.2 hr*ng/mL, about 3.3 hr*ng/mL, about 3.4 hr*ng/mL, about 3.5 hr*ng/mL, about 3.6 hr*ng/mL, about 3.7 hr*ng/mL, about 3.8 hr*ng/mL, about 3.9 hr*ng/mL, about 4 hr*ng/mL, about 4.1 hr*ng/mL, about 4.2 hr*ng/mL, about 4.3 hr*ng/mL, about 4.4 hr*ng/mL, about 4.5 hr*ng/mL, about 4.6 hr*ng/mL, about 4.7 hr*ng/mL, about 4.8 hr*ng/mL, about 4.9 hr*ng/mL, about 5 hr*ng/mL, about 5.5 hr*ng/mL, about 6 hr*ng/mL, about 6.5 hr*ng/mL, about 7 hr*ng/mL, about 7.5 hr*ng/mL, about 8 hr*ng/mL, about 8.5 hr*ng/mL, about 9 hr*ng/mL, about 9.5 hr*ng/mL, about 10 hr*ng/mL, about 11 hr*ng/mL, about 12 hr*ng/mL, about 13 hr*ng/mL, about 14 hr*ng/mL, about 15 hr*ng/mL, about 16 hr*ng/mL, about 17 hr*ng/mL, about 18 hr*ng/mL, about 19 hr*ng/mL, about 20 hr*ng/mL, about 25 hr*ng/mL, about 30 hr*ng/mL, about 35 hr*ng/mL, about 40 hr*ng/mL, about 45 hr*ng/mL, about 50 hr*ng/mL, about 60 hr*ng/mL, about 70 hr*ng/mL, about 80 hr*ng/mL, about 90 hr*ng/mL, or about 100 hr*ng/mL per mg of β-lactam compound administered daily, or any range therebetween.

In some embodiments, the resulted $C_{max}$ of the plasma concentration for the β-lactam compound in the comparable subject at the first day of the administration ranges from about 1500 ng/mL to about 2500 ng/mL, from about 1600 ng/mL to about 2400 ng/mL, from about 1700 ng/mL to about 2300 ng/mL, from about 1800 ng/mL to about 2200 ng/mL, from about 1900 ng/mL to about 2100 ng/mL, from about 1950 ng/mL to about 2050 ng/mL, from about 1980 ng/mL to about 2020 ng/mL, from about 1990 ng/mL to about 2010 ng/mL.

In some embodiments, the resulted $C_{max}$ of the plasma concentration for the β-lactam compound in the comparable subject at the first day of the administration is at about 2000 ng/mL.

In some embodiments, the resulted $C_{max}$ of the plasma concentration for the β-lactam compound in the comparable subject at the seventh day of the administration ranges from about 700 ng/mL to about 1800 ng/mL, from about 800 ng/mL to about 1700 ng/mL, from about 900 ng/mL to about 1600 ng/mL, from about 1000 ng/mL to about 1500 ng/mL, from about 1100 ng/mL to about 1400 ng/mL, from about 1200 ng/mL to about 1300 ng/mL, from about 1230 ng/mL to about 1270 ng/mL, from about 1240 ng/mL to about 1260 ng/mL.

In some embodiments, the resulted $C_{max}$ of the plasma concentration for the β-lactam compound in the comparable subject at the seventh day of the administration is at about 1250 ng/mL.

In some embodiments, the resulted $C_{max}$ of the plasma concentration for the β-lactam compound in the subject in need thereof at the first day of the administration ranges from about 1600 ng/mL to about 2700 ng/mL, from about 1700 ng/mL to about 2600 ng/mL, from about 1800 ng/mL to about 2500 ng/mL, from about 1900 ng/mL to about 2400 ng/mL, from about 2000 ng/mL to about 2300 ng/mL, from about 2100 ng/mL to about 2200 ng/mL, from about 2130 ng/mL to about 2170 ng/mL, from about 2140 ng/mL to about 2160 ng/mL.

In some embodiments, the resulted $C_{max}$ of the plasma concentration for the β-lactam compound in the subject in need thereof at the first day of the administration is at about 2150 ng/mL.

In some embodiments, the resulted $C_{max}$ of the plasma concentration for the β-lactam compound in the subject in need thereof at the seventh day of the administration ranges from about 1600 ng/mL to about 2700 ng/mL, from about 1700 ng/mL to about 2600 ng/mL, from about 1800 ng/mL to about 2500 ng/mL, from about 1900 ng/mL to about 2400 ng/mL, from about 2000 ng/mL to about 2300 ng/mL, from about 2050 ng/mL to about 2200 ng/mL, from about 2100 ng/mL to about 2140 ng/mL, from about 2110 ng/mL to about 2130 ng/mL.

In some embodiments, the resulted $C_{max}$ of the plasma concentration for the β-lactam compound in the subject in need thereof at the seventh day of the administration is at about 2120 ng/mL.

In some embodiments, the resulted $C_{max}$ of the plasma concentration for the β-lactam compound in the comparable subject at the first day of the administration ranges from about 1200 ng/mL to about 2200 ng/mL, from about 1300 ng/mL to about 2100 ng/mL, from about 1400 ng/mL to about 2000 ng/mL, from about 1500 ng/mL to about 1900 ng/mL, from about 1600 ng/mL to about 1800 ng/mL, from about 1650 ng/mL to about 1750 ng/mL, from about 1680 ng/mL to about 1720 ng/mL, from about 1690 ng/mL to about 1710 ng/mL.

In some embodiments, the resulted $C_{max}$ of the plasma concentration for the β-lactam compound in the comparable subject at the first day of the administration is at about 1700 ng/mL.

In some embodiments, the resulted $C_{max}$ of the plasma concentration for the β-lactam compound in the comparable subject at the seventh day of the administration ranges from about 800 ng/mL to about 1800 ng/mL, from about 900 ng/mL to about 1700 ng/mL, from about 1000 ng/mL to about 1600 ng/mL, from about 1100 ng/mL to about 1500 ng/mL, from about 1200 ng/mL to about 1400 ng/mL, from about 1250 ng/mL to about 1350 ng/mL, from about 1270 ng/mL to about 1310 ng/mL, from about 1280 ng/mL to about 1300 ng/mL.

In some embodiments, the resulted $C_{max}$ of the plasma concentration for the β-lactam compound in the comparable subject at the seventh day of the administration is at about 1290 ng/mL.

In some embodiments, the resulted $C_{max}$ of the plasma concentration for the β-lactam compound in the subject in need thereof at the first day of the administration ranges from about 1200 ng/mL to about 2200 ng/mL, from about 1300 ng/mL to about 2100 ng/mL, from about 1400 ng/mL to about 2000 ng/mL, from about 1500 ng/mL to about 1900 ng/mL, from about 1600 ng/mL to about 1850 ng/mL, from about 1650 ng/mL to about 1800 ng/mL, from about 1700 ng/mL to about 1740 ng/mL, from about 1710 ng/mL to about 1730 ng/mL.

In some embodiments, the resulted $C_{max}$ of the plasma concentration for the β-lactam compound in the subject in need thereof at the first day of the administration is at about 1720 ng/mL.

In some embodiments, the resulted $C_{max}$ of the plasma concentration for the β-lactam compound in the subject in need thereof at the seventh day of the administration ranges from about 900 ng/mL to about 2000 ng/mL, from about 1000 ng/mL to about 1900 ng/mL, from about 1100 ng/mL to about 1800 ng/mL, from about 1200 ng/mL to about 1700 ng/mL, from about 1300 ng/mL to about 1600 ng/mL, from about 1400 ng/mL to about 1550 ng/mL, from about 1460 ng/mL to about 1500 ng/mL, from about 1470 ng/mL to about 1490 ng/mL.

In some embodiments, the resulted $C_{max}$ of the plasma concentration for the β-lactam compound in the subject in need thereof at the seventh day of the administration is at about 1480 ng/mL.

In some embodiments, the resulted AUC of the plasma concentration for the β-lactam compound in the comparable subject at the first day of the administration ranges from about 2500 hr*ng/mL to about 3200 hr*ng/mL, from about 2600 hr*ng/mL to about 3100 hr*ng/mL, from about 2700 hr*ng/mL to about 3000 hr*ng/mL, from about 2750 hr*ng/mL to about 2950 hr*ng/mL, from about 2800 hr*ng/mL to about 2870 hr*ng/mL, ranges from about 2810 hr*ng/mL to about 2860 hr*ng/mL, or from about 2820 hr*ng/mL to about 2850 hr*ng/mL.

In some embodiments, the resulted AUC of the plasma concentration for the β-lactam compound in the comparable subject at the first day of the administration is at about 2840 hr*ng/mL.

In some embodiments, the resulted AUC of the plasma concentration for the β-lactam compound in the comparable subject at the seventh day of the administration ranges from about 1600 hr*ng/mL to about 2200 hr*ng/mL, from about 1700 hr*ng/mL to about 2100 hr*ng/mL, from about 1800 hr*ng/mL to about 2000 hr*ng/mL, from about 1850 hr*ng/mL to about 1950 hr*ng/mL, from about 1860 hr*ng/mL to about 1920 hr*ng/mL, ranges from about 1870 hr*ng/mL to about 1910 hr*ng/mL, or from about 1880 hr*ng/mL to about 1900 hr*ng/mL.

In some embodiments, the resulted AUC of the plasma concentration for the β-lactam compound in the comparable subject at the seventh day of the administration is at about 1890 hr*ng/mL.

In some embodiments, the resulted AUC of the plasma concentration for the β-lactam compound in the subject in need thereof at the first day of the administration ranges from about 3900 hr*ng/mL to about 4500 hr*ng/mL, from about 4000 hr*ng/mL to about 4400 hr*ng/mL, from about 4100 hr*ng/mL to about 4300 hr*ng/mL, from about 4150 hr*ng/mL to about 4250 hr*ng/mL, from about 4160 hr*ng/mL to about 4220 hr*ng/mL, ranges from about 4170 hr*ng/mL to about 4210 hr*ng/mL, or from about 4180 hr*ng/mL to about 4200 hr*ng/mL.

In some embodiments, the resulted AUC of the plasma concentration for the β-lactam compound in the subject in need thereof at the first day of the administration is at about 4190 hr*ng/mL.

In some embodiments, the resulted AUC of the plasma concentration for the β-lactam compound in the subject in need thereof at the seventh day of the administration ranges from about 4100 hr*ng/mL to about 4700 hr*ng/mL, from about 4200 hr*ng/mL to about 4600 hr*ng/mL, from about 4300 hr*ng/mL to about 4500 hr*ng/mL, from about 4350 hr*ng/mL to about 4450 hr*ng/mL, from about 4370 hr*ng/mL to about 4430 hr*ng/mL, ranges from about 4380 hr*ng/mL to about 4420 hr*ng/mL, or from about 4390 hr*ng/mL to about 4410 hr*ng/mL.

In some embodiments, the resulted AUC of the plasma concentration for the β-lactam compound in the subject in need thereof at the seventh day of the administration is at about 4400 hr*ng/mL.

In some embodiments, the resulted AUC of the plasma concentration for the β-lactam compound in the comparable subject at the first day of the administration ranges from about 3200 hr*ng/mL to about 4000 hr*ng/mL, from about 3300 hr*ng/mL to about 3900 hr*ng/mL, from about 3400 hr*ng/mL to about 3800 hr*ng/mL, from about 3500 hr*ng/mL to about 3700 hr*ng/mL, from about 3590 hr*ng/mL to about 3650 hr*ng/mL, ranges from about 3600 hr*ng/mL to about 3640 hr*ng/mL, or from about 3610 hr*ng/mL to about 3630 hr*ng/mL.

In some embodiments, the resulted AUC of the plasma concentration for the β-lactam compound in the comparable subject at the first day of the administration is at about 3620 hr*ng/mL.

In some embodiments, the resulted AUC of the plasma concentration for the β-lactam compound in the comparable subject at the seventh day of the administration ranges from about 2200 hr*ng/mL to about 3100 hr*ng/mL, from about 2300 hr*ng/mL to about 3000 hr*ng/mL, from about 2400 hr*ng/mL to about 2900 hr*ng/mL, from about 2500 hr*ng/mL to about 2800 hr*ng/mL, from about 2600 hr*ng/mL to about 2700 hr*ng/mL, ranges from about 2610 hr*ng/mL to about 2650 hr*ng/mL, or from about 2620 hr*ng/mL to about 2640 hr*ng/mL.

In some embodiments, the resulted AUC of the plasma concentration for the β-lactam compound in the comparable subject at the seventh day of the administration is at about 2630 hr*ng/mL.

In some embodiments, the resulted AUC of the plasma concentration for the β-lactam compound in the subject in need thereof at the first day of the administration ranges from about 3400 hr*ng/mL to about 4300 hr*ng/mL, from about 3500 hr*ng/mL to about 4200 hr*ng/mL, from about 3600 hr*ng/mL to about 4100 hr*ng/mL, from about 3700 hr*ng/mL to about 4000 hr*ng/mL, from about 3800 hr*ng/mL to about 3900 hr*ng/mL, ranges from about 3840 hr*ng/mL to about 3880 hr*ng/mL, or from about 3850 hr*ng/mL to about 3870 hr*ng/mL.

In some embodiments, the resulted AUC of the plasma concentration for the β-lactam compound in the subject in need thereof at the first day of the administration is at about 3860 hr*ng/mL.

In some embodiments, the resulted AUC of the plasma concentration for the β-lactam compound in the subject in need thereof at the seventh day of the administration ranges from about 3900 hr*ng/mL to about 4700 hr*ng/mL, from about 4000 hr*ng/mL to about 4600 hr*ng/mL, from about 4100 hr*ng/mL to about 4400 hr*ng/mL, from about 4200 hr*ng/mL to about 4400 hr*ng/mL, from about 4250 hr*ng/mL to about 4350 hr*ng/mL, ranges from about 4260 hr*ng/mL to about 4300 hr*ng/mL, or from about 4270 hr*ng/mL to about 4290 hr*ng/mL.

In some embodiments, the resulted AUC of the plasma concentration for the β-lactam compound in the subject in need thereof at the seventh day of the administration is at about 4280 hr*ng/mL.

In some embodiments, the resulted $C_{max}$ of the plasma concentration for the β-lactam compound in the comparable subject at the first day of the administration is at about 100 ng/mL, about 150 ng/mL, about 200 ng/mL, about 250 ng/mL, about 300 ng/mL, about 350 ng/mL, about 400 ng/mL, about 450 ng/mL, about 500 ng/mL, about 550 ng/mL, about 600 ng/mL, about 650 ng/mL, about 700 ng/mL, about 750 ng/mL, about 800 ng/mL, about 850 ng/mL, about 900 ng/mL, about 950 ng/mL, about 1000 ng/mL, about 1050 ng/mL, about 1100 ng/mL, about 1150 ng/mL, about 1200 ng/mL, about 1250 ng/mL, about 1300 ng/mL, about 1350 ng/mL, about 1400 ng/mL, about 1450 ng/mL, about 1500 ng/mL, about 1550 ng/mL, about 1600 ng/mL, about 1650 ng/mL, about 1700 ng/mL, about 1750 ng/mL, about 1800 ng/mL, about 1850 ng/mL, about 1900 ng/mL, about 1950 ng/mL, about 2000 ng/mL, about 2050 ng/mL, about 2100 ng/mL, about 2150 ng/mL, about 2200 ng/mL, about 2250 ng/mL, about 2300 ng/mL, about 2350 ng/mL, about 2400 ng/mL, about 2450 ng/mL, about 2500 ng/mL, about 2550 ng/mL, about 2600 ng/mL, about 2650 ng/mL, about 2700 ng/mL, about 2750 ng/mL, about 2800 ng/mL, about 2850 ng/mL, about 2900 ng/mL, about 2950 ng/mL, about 3000 ng/mL, about 3050 ng/mL, about 3100 ng/mL, about 3150 ng/mL, about 3200 ng/mL, about 3250 ng/mL, about 3300 ng/mL, about 3350 ng/mL, about 3400 ng/mL, about 3450 ng/mL, about 3500 ng/mL, about 3550 ng/mL, about 3600 ng/mL, about 3650 ng/mL, about 3700 ng/mL, about 3750 ng/mL, about 3800 ng/mL, about 3850 ng/mL, about 3900 ng/mL, about 3950 ng/mL, about 4000 ng/mL, about 4050 ng/mL, about 4100 ng/mL, about 4150 ng/mL, about 4200 ng/mL, about 4250 ng/mL, about 4300 ng/mL, about 4350 ng/mL, about 4400 ng/mL, about 4450 ng/mL, about 4500 ng/mL, about 4550 ng/mL, about 4600 ng/mL, about 4650 ng/mL, about 4700 ng/mL, about 4750 ng/mL, about 4800 ng/mL, about 4850 ng/mL, about 4900 ng/mL, about 4950 ng/mL, about 5000 ng/mL, about 5100 ng/mL, about 5200 ng/mL, about 5300 ng/mL, about 5400 ng/mL, about 5500 ng/mL, about 5600 ng/mL, about 5700 ng/mL, about 5800 ng/mL, about 5900 ng/mL, about 6000 ng/mL, about 6500 ng/mL, about 7000 ng/mL, about 7500 ng/mL, about 8000 ng/mL, about 8500 ng/mL, about 9000 ng/mL, about 9500 ng/mL, about 10000 ng/mL, about 11000 ng/mL, about 12000 ng/mL, about 13000 ng/mL, about 14000 ng/mL, about 15000 ng/mL, about 16000 ng/mL, about 17000 ng/mL, about 18000 ng/mL, about 19000 ng/mL, or about 20000 ng/mL, or any range therebetween.

In some embodiments, the resulted $C_{max}$ of the plasma concentration for the β-lactam compound in the comparable subject at the seventh day of the administration is at about 100 ng/mL, about 150 ng/mL, about 200 ng/mL, about 250 ng/mL, about 300 ng/mL, about 350 ng/mL, about 400 ng/mL, about 450 ng/mL, about 500 ng/mL, about 550 ng/mL, about 600 ng/mL, about 650 ng/mL, about 700 ng/mL, about 750 ng/mL, about 800 ng/mL, about 850 ng/mL, about 900 ng/mL, about 950 ng/mL, about 1000 ng/mL, about 1050 ng/mL, about 1100 ng/mL, about 1150 ng/mL, about 1200 ng/mL, about 1250 ng/mL, about 1300 ng/mL, about 1350 ng/mL, about 1400 ng/mL, about 1450 ng/mL, about 1500 ng/mL, about 1550 ng/mL, about 1600 ng/mL, about 1650 ng/mL, about 1700 ng/mL, about 1750 ng/mL, about 1800 ng/mL, about 1850 ng/mL, about 1900 ng/mL, about 1950 ng/mL, about 2000 ng/mL, about 2050 ng/mL, about 2100 ng/mL, about 2150 ng/mL, about 2200 ng/mL, about 2250 ng/mL, about 2300 ng/mL, about 2350 ng/mL, about 2400 ng/mL, about 2450 ng/mL, about 2500 ng/mL, about 2550 ng/mL, about 2600 ng/mL, about 2650 ng/mL, about 2700 ng/mL, about 2750 ng/mL, about 2800 ng/mL, about 2850 ng/mL, about 2900 ng/mL, about 2950 ng/mL, about 3000 ng/mL, about 3050 ng/mL, about 3100 ng/mL, about 3150 ng/mL, about 3200 ng/mL, about 3250 ng/mL, about 3300 ng/mL, about 3350 ng/mL, about 3400 ng/mL, about 3450 ng/mL, about 3500 ng/mL, about 3550 ng/mL, about 3600 ng/mL, about 3650 ng/mL, about 3700 ng/mL, about 3750 ng/mL, about 3800 ng/mL, about 3850 ng/mL, about 3900 ng/mL, about 3950 ng/mL, about 4000 ng/mL, about 4050 ng/mL, about 4100 ng/mL, about 4150 ng/mL, about 4200 ng/mL, about 4250 ng/mL, about 4300 ng/mL, about 4350 ng/mL, about 4400 ng/mL, about 4450 ng/mL, about 4500 ng/mL, about 4550 ng/mL, about 4600 ng/mL, about 4650 ng/mL, about 4700 ng/mL, about 4750 ng/mL, about 4800 ng/mL, about 4850 ng/mL, about 4900 ng/mL, about 4950 ng/mL, about 5000 ng/mL, about 5100 ng/mL, about 5200 ng/mL, about 5300 ng/mL, about 5400 ng/mL, about 5500 ng/mL, about 5600 ng/mL, about 5700 ng/mL, about 5800 ng/mL, about 5900 ng/mL, about 6000 ng/mL, about 6500 ng/mL, about 7000 ng/mL, about 7500 ng/mL, about 8000 ng/mL, about 8500 ng/mL, about 9000 ng/mL, about 9500 ng/mL, about 10000 ng/mL, about 11000 ng/mL, about 12000 ng/mL, about 13000 ng/mL, about 14000 ng/mL, about 15000 ng/mL, about 16000 ng/mL, about 17000 ng/mL, about 18000 ng/mL, about 19000 ng/mL, or about 20000 ng/mL, or any range therebetween.

In some embodiments, the resulted $C_{max}$ of the plasma concentration for the β-lactam compound in the subject in need thereof at the first day of the administration is at about 100 ng/mL, about 150 ng/mL, about 200 ng/mL, about 250 ng/mL, about 300 ng/mL, about 350 ng/mL, about 400 ng/mL, about 450 ng/mL, about 500 ng/mL, about 550 ng/mL, about 600 ng/mL, about 650 ng/mL, about 700 ng/mL, about 750 ng/mL, about 800 ng/mL, about 850 ng/mL, about 900 ng/mL, about 950 ng/mL, about 1000 ng/mL, about 1050 ng/mL, about 1100 ng/mL, about 1150 ng/mL, about 1200 ng/mL, about 1250 ng/mL, about 1300 ng/mL, about 1350 ng/mL, about 1400 ng/mL, about 1450 ng/mL, about 1500 ng/mL, about 1550 ng/mL, about 1600 ng/mL, about 1650 ng/mL, about 1700 ng/mL, about 1750 ng/mL, about 1800 ng/mL, about 1850 ng/mL, about 1900 ng/mL, about 1950 ng/mL, about 2000 ng/mL, about 2050 ng/mL, about 2100 ng/mL, about 2150 ng/mL, about 2200 ng/mL, about 2250 ng/mL, about 2300 ng/mL, about 2350 ng/mL, about 2400 ng/mL, about 2450 ng/mL, about 2500 ng/mL, about 2550 ng/mL, about 2600 ng/mL, about 2650 ng/mL, about 2700 ng/mL, about 2750 ng/mL, about 2800 ng/mL, about 2850 ng/mL, about 2900 ng/mL, about 2950 ng/mL, about 3000 ng/mL, about 3050 ng/mL, about 3100 ng/mL, about 3150 ng/mL, about 3200 ng/mL, about 3250 ng/mL, about 3300 ng/mL, about 3350 ng/mL, about 3400 ng/mL, about 3450 ng/mL, about 3500 ng/mL, about 3550 ng/mL, about 3600 ng/mL, about 3650 ng/mL, about 3700 ng/mL, about 3750 ng/mL, about 3800 ng/mL, about 3850 ng/mL, about 3900 ng/mL, about 3950 ng/mL, about 4000 ng/mL, about 4050 ng/mL, about 4100 ng/mL, about 4150 ng/mL, about 4200 ng/mL, about 4250 ng/mL, about 4300 ng/mL, about 4350 ng/mL, about 4400 ng/mL, about 4450 ng/mL, about 4500 ng/mL, about 4550 ng/mL, about 4600 ng/mL, about 4650 ng/mL, about 4700 ng/mL, about 4750 ng/mL, about 4800 ng/mL, about 4850 ng/mL, about 4900 ng/mL, about 4950 ng/mL, about 5000 ng/mL, about 5100 ng/mL, about 5200 ng/mL, about 5300 ng/mL, about 5400 ng/mL, about 5500 ng/mL, about 5600 ng/mL, about 5700 ng/mL, about 5800 ng/mL, about 5900 ng/mL, about 6000 ng/mL, about 6500 ng/mL, about 7000 ng/mL, about 7500 ng/mL, about 8000 ng/mL, about 8500 ng/mL, about 9000 ng/mL, about 9500 ng/mL, about 10000 ng/mL, about 11000 ng/mL, about 12000 ng/mL, about 13000 ng/mL, about 14000 ng/mL, about 15000 ng/mL, about 16000 ng/mL, about 17000 ng/mL, about 18000 ng/mL, about 19000 ng/mL, or about 20000 ng/mL, or any range therebetween.

In some embodiments, the resulted $C_{max}$ of the plasma concentration for the β-lactam compound in the subject in need thereof at the seventh day of the administration is at about 100 ng/mL, about 150 ng/mL, about 200 ng/mL, about 250 ng/mL, about 300 ng/mL, about 350 ng/mL, about 400 ng/mL, about 450 ng/mL, about 500 ng/mL, about 550 ng/mL, about 600 ng/mL, about 650 ng/mL, about 700 ng/mL, about 750 ng/mL, about 800 ng/mL, about 850 ng/mL, about 900 ng/mL, about 950 ng/mL, about 1000 ng/mL, about 1050 ng/mL, about 1100 ng/mL, about 1150 ng/mL, about 1200 ng/mL, about 1250 ng/mL, about 1300 ng/mL, about 1350 ng/mL, about 1400 ng/mL, about 1450 ng/mL, about 1500 ng/mL, about 1550 ng/mL, about 1600 ng/mL, about 1650 ng/mL, about 1700 ng/mL, about 1750 ng/mL, about 1800 ng/mL, about 1850 ng/mL, about 1900 ng/mL, about 1950 ng/mL, about 2000 ng/mL, about 2050 ng/mL, about 2100 ng/mL, about 2150 ng/mL, about 2200 ng/mL, about 2250 ng/mL, about 2300 ng/mL, about 2350 ng/mL, about 2400 ng/mL, about 2450 ng/mL, about 2500 ng/mL, about 2550 ng/mL, about 2600 ng/mL, about 2650 ng/mL, about 2700 ng/mL, about 2750 ng/mL, about 2800 ng/mL, about 2850 ng/mL, about 2900 ng/mL, about 2950 ng/mL, about 3000 ng/mL, about 3050 ng/mL, about 3100 ng/mL, about 3150 ng/mL, about 3200 ng/mL, about 3250 ng/mL, about 3300 ng/mL, about 3350 ng/mL, about 3400 ng/mL, about 3450 ng/mL, about 3500 ng/mL, about 3550 ng/mL, about 3600 ng/mL, about 3650 ng/mL, about 3700 ng/mL, about 3750 ng/mL, about 3800 ng/mL, about 3850 ng/mL, about 3900 ng/mL, about 3950 ng/mL, about 4000 ng/mL, about 4050 ng/mL, about 4100 ng/mL, about 4150 ng/mL, about 4200 ng/mL, about 4250 ng/mL, about 4300 ng/mL, about 4350 ng/mL, about 4400 ng/mL, about 4450 ng/mL, about 4500 ng/mL, about 4550 ng/mL, about 4600 ng/mL, about 4650 ng/mL, about 4700 ng/mL, about 4750 ng/mL, about 4800 ng/mL, about 4850 ng/mL, about 4900 ng/mL, about 4950 ng/mL, about 5000 ng/mL, about 5100 ng/mL, about 5200 ng/mL, about 5300 ng/mL, about 5400 ng/mL, about 5500 ng/mL, about 5600 ng/mL, about 5700 ng/mL, about 5800 ng/mL, about 5900 ng/mL, about 6000 ng/mL, about 6500 ng/mL, about 7000 ng/mL, about 7500 ng/mL, about 8000 ng/mL, about 8500 ng/mL, about 9000 ng/mL, about 9500 ng/mL, about 10000 ng/mL, about 11000 ng/mL, about 12000 ng/mL, about 13000 ng/mL, about 14000 ng/mL, about 15000 ng/mL, about 16000 ng/mL, about 17000 ng/mL, about 18000 ng/mL, about 19000 ng/mL, or about 20000 ng/mL, or any range therebetween.

In some embodiments, the resulted AUC of the plasma concentration for the β-lactam compound in the comparable subject at the first day of the administration is at about 100 hr*ng/mL, about 150 hr*ng/mL, about 200 hr*ng/mL, about 250 hr*ng/mL, about 300 hr*ng/mL, about 350 hr*ng/mL, about 400 hr*ng/mL, about 450 hr*ng/mL, about 500 hr*ng/mL, about 550 hr*ng/mL, about 600 hr*ng/mL, about 650 hr*ng/mL, about 700 hr*ng/mL, about 750 hr*ng/mL, about 800 hr*ng/mL, about 850 hr*ng/mL, about 900 hr*ng/mL, about 950 hr*ng/mL, about 1000 hr*ng/mL, about 1050 hr*ng/mL, about 1100 hr*ng/mL, about 1150 hr*ng/mL, about 1200 hr*ng/mL, about 1250 hr*ng/mL, about 1300 hr*ng/mL, about 1350 hr*ng/mL, about 1400 hr*ng/mL, about 1450 hr*ng/mL, about 1500 hr*ng/mL, about 1550 hr*ng/mL, about 1600 hr*ng/mL, about 1650 hr*ng/mL, about 1700 hr*ng/mL, about 1750 hr*ng/mL, about 1800 hr*ng/mL, about 1850 hr*ng/mL, about 1900 hr*ng/mL, about 1950 hr*ng/mL, about 2000 hr*ng/mL, about 2050 hr*ng/mL, about 2100 hr*ng/mL, about 2150 hr*ng/mL, about 2200 hr*ng/mL, about 2250 hr*ng/mL, about 2300 hr*ng/mL, about 2350 hr*ng/mL, about 2400 hr*ng/mL, about 2450 hr*ng/mL, about 2500 hr*ng/mL, about 2550 hr*ng/mL, about 2600 hr*ng/mL, about 2650 hr*ng/mL, about 2700 hr*ng/mL, about 2750 hr*ng/mL, about 2800 hr*ng/mL, about 2850 hr*ng/mL, about 2900 hr*ng/mL, about 2950 hr*ng/mL, about 3000 hr*ng/mL, about 3050 hr*ng/mL, about 3100 hr*ng/mL, about 3150 hr*ng/mL, about 3200 hr*ng/mL, about 3250 hr*ng/mL, about 3300 hr*ng/mL, about 3350 hr*ng/mL, about 3400 hr*ng/mL, about 3450 hr*ng/mL, about 3500 hr*ng/mL, about 3550 hr*ng/mL, about 3600 hr*ng/mL, about 3650 hr*ng/mL, about 3700 hr*ng/mL, about 3750 hr*ng/mL, about 3800 hr*ng/mL, about 3850 hr*ng/mL, about 3900 hr*ng/mL, about 3950 hr*ng/mL, about 4000 hr*ng/mL, about 4050 hr*ng/mL, about 4100 hr*ng/mL, about 4150 hr*ng/mL, about 4200 hr*ng/mL, about 4250 hr*ng/mL, about 4300 hr*ng/mL, about 4350 hr*ng/mL, about 4400 hr*ng/mL, about 4450 hr*ng/mL, about 4500 hr*ng/mL, about 4550 hr*ng/mL, about 4600 hr*ng/mL, about 4650 hr*ng/mL, about 4700 hr*ng/mL, about 4750 hr*ng/mL, about 4800 hr*ng/mL, about 4850 hr*ng/mL, about 4900 hr*ng/mL, about 4950 hr*ng/mL, about 5000 hr*ng/mL, about 5100 hr*ng/mL, about 5200 hr*ng/mL, about 5300 hr*ng/mL, about 5400 hr*ng/mL, about 5500 hr*ng/mL, about 5600 hr*ng/mL, about 5700 hr*ng/mL, about 5800 hr*ng/mL, about 5900 hr*ng/mL, about 6000 hr*ng/mL, about 6500 hr*ng/mL, about 7000 hr*ng/mL, about 7500 hr*ng/mL, about 8000 hr*ng/mL, about 8500 hr*ng/mL, about 9000 hr*ng/mL, about 9500 hr*ng/mL, about 10000 hr*ng/mL, about 11000 hr*ng/mL, about 12000 hr*ng/mL, about 13000 hr*ng/mL, about 14000 hr*ng/mL, about 15000 hr*ng/mL, about 16000 hr*ng/mL, about 17000 hr*ng/mL, about 18000 hr*ng/mL, about 19000 hr*ng/mL, or about 20000 hr*ng/mL, or any range therebetween.

In some embodiments, the resulted AUC of the plasma concentration for the β-lactam compound in the comparable subject at the seventh day of the administration is at about 100 hr*ng/mL, about 150 hr*ng/mL, about 200 hr*ng/mL, about 250 hr*ng/mL, about 300 hr*ng/mL, about 350 hr*ng/mL, about 400 hr*ng/mL, about 450 hr*ng/mL, about 500 hr*ng/mL, about 550 hr*ng/mL, about 600 hr*ng/mL, about 650 hr*ng/mL, about 700 hr*ng/mL, about 750 hr*ng/mL, about 800 hr*ng/mL, about 850 hr*ng/mL, about 900 hr*ng/mL, about 950 hr*ng/mL, about 1000 hr*ng/mL, about 1050 hr*ng/mL, about 1100 hr*ng/mL, about 1150 hr*ng/mL, about 1200 hr*ng/mL, about 1250 hr*ng/mL, about 1300 hr*ng/mL, about 1350 hr*ng/mL, about 1400 hr*ng/mL, about 1450 hr*ng/mL, about 1500 hr*ng/mL, about 1550 hr*ng/mL, about 1600 hr*ng/mL, about 1650 hr*ng/mL, about 1700 hr*ng/mL, about 1750 hr*ng/mL, about 1800 hr*ng/mL, about 1850 hr*ng/mL, about 1900 hr*ng/mL, about 1950 hr*ng/mL, about 2000 hr*ng/mL, about 2050 hr*ng/mL, about 2100 hr*ng/mL, about 2150 hr*ng/mL, about 2200 hr*ng/mL, about 2250 hr*ng/mL, about 2300 hr*ng/mL, about 2350 hr*ng/mL, about 2400 hr*ng/mL, about 2450 hr*ng/mL, about 2500 hr*ng/mL, about 2550 hr*ng/mL, about 2600 hr*ng/mL, about 2650 hr*ng/mL, about 2700 hr*ng/mL, about 2750 hr*ng/mL, about 2800 hr*ng/mL, about 2850 hr*ng/mL, about 2900 hr*ng/mL, about 2950 hr*ng/mL, about 3000 hr*ng/mL, about 3050 hr*ng/mL, about 3100 hr*ng/mL, about 3150 hr*ng/mL, about 3200 hr*ng/mL, about 3250 hr*ng/mL, about 3300 hr*ng/mL, about 3350 hr*ng/mL, about 3400 hr*ng/mL, about 3450 hr*ng/mL, about 3500 hr*ng/mL, about 3550 hr*ng/mL, about 3600 hr*ng/mL, about 3650 hr*ng/mL, about 3700 hr*ng/mL, about 3750 hr*ng/mL, about 3800 hr*ng/mL, about 3850 hr*ng/mL, about 3900 hr*ng/mL, about 3950 hr*ng/mL, about 4000 hr*ng/mL, about 4050 hr*ng/mL, about 4100 hr*ng/mL, about 4150 hr*ng/mL, about 4200 hr*ng/mL, about 4250 hr*ng/mL, about 4300 hr*ng/mL, about 4350 hr*ng/mL, about 4400 hr*ng/mL, about 4450 hr*ng/mL, about 4500 hr*ng/mL, about 4550 hr*ng/mL, about 4600 hr*ng/mL, about 4650 hr*ng/mL, about 4700 hr*ng/mL, about 4750 hr*ng/mL, about 4800 hr*ng/mL, about 4850 hr*ng/mL, about 4900 hr*ng/mL, about 4950 hr*ng/mL, about 5000 hr*ng/mL, about 5100 hr*ng/mL, about 5200 hr*ng/mL, about 5300 hr*ng/mL, about 5400 hr*ng/mL, about 5500 hr*ng/mL, about 5600 hr*ng/mL, about 5700 hr*ng/mL, about 5800 hr*ng/mL, about 5900 hr*ng/mL, about 6000 hr*ng/mL, about 6500 hr*ng/mL, about 7000 hr*ng/mL, about 7500 hr*ng/mL, about 8000 hr*ng/mL, about 8500 hr*ng/mL, about 9000 hr*ng/mL, about 9500 hr*ng/mL, about 10000 hr*ng/mL, about 11000 hr*ng/mL, about 12000 hr*ng/mL, about 13000 hr*ng/mL, about 14000 hr*ng/mL, about 15000 hr*ng/mL, about 16000 hr*ng/mL, about 17000 hr*ng/mL, about 18000 hr*ng/mL, about 19000 hr*ng/mL, or about 20000 hr*ng/mL, or any range therebetween.

In some embodiments, the resulted AUC of the plasma concentration for the β-lactam compound in the subject in need thereof at the first day of the administration is at about 100 hr*ng/mL, about 150 hr*ng/mL, about 200 hr*ng/mL, about 250 hr*ng/mL, about 300 hr*ng/mL, about 350 hr*ng/mL, about 400 hr*ng/mL, about 450 hr*ng/mL, about 500 hr*ng/mL, about 550 hr*ng/mL, about 600 hr*ng/mL, about 650 hr*ng/mL, about 700 hr*ng/mL, about 750 hr*ng/mL, about 800 hr*ng/mL, about 850 hr*ng/mL, about 900 hr*ng/mL, about 950 hr*ng/mL, about 1000 hr*ng/mL, about 1050 hr*ng/mL, about 1100 hr*ng/mL, about 1150 hr*ng/mL, about 1200 hr*ng/mL, about 1250 hr*ng/mL, about 1300 hr*ng/mL, about 1350 hr*ng/mL, about 1400 hr*ng/mL, about 1450 hr*ng/mL, about 1500 hr*ng/mL, about 1550 hr*ng/mL, about 1600 hr*ng/mL, about 1650 hr*ng/mL, about 1700 hr*ng/mL, about 1750 hr*ng/mL, about 1800 hr*ng/mL, about 1850 hr*ng/mL, about 1900 hr*ng/mL, about 1950 hr*ng/mL, about 2000 hr*ng/mL, about 2050 hr*ng/mL, about 2100 hr*ng/mL, about 2150 hr*ng/mL, about 2200 hr*ng/mL, about 2250 hr*ng/mL, about 2300 hr*ng/mL, about 2350 hr*ng/mL, about 2400 hr*ng/mL, about 2450 hr*ng/mL, about 2500 hr*ng/mL, about 2550 hr*ng/mL, about 2600 hr*ng/mL, about 2650 hr*ng/mL, about 2700 hr*ng/mL, about 2750 hr*ng/mL, about 2800 hr*ng/mL, about 2850 hr*ng/mL, about 2900 hr*ng/mL, about 2950 hr*ng/mL, about 3000 hr*ng/mL, about 3050 hr*ng/mL, about 3100 hr*ng/mL, about 3150 hr*ng/mL, about 3200 hr*ng/mL, about 3250 hr*ng/mL, about 3300 hr*ng/mL, about 3350 hr*ng/mL, about 3400 hr*ng/mL, about 3450 hr*ng/mL, about 3500 hr*ng/mL, about 3550 hr*ng/mL, about 3600 hr*ng/mL, about 3650 hr*ng/mL, about 3700 hr*ng/mL, about 3750 hr*ng/mL, about 3800 hr*ng/mL, about 3850 hr*ng/mL, about 3900 hr*ng/mL, about 3950 hr*ng/mL, about 4000 hr*ng/mL, about 4050 hr*ng/mL, about 4100 hr*ng/mL, about 4150 hr*ng/mL, about 4200 hr*ng/mL, about 4250 hr*ng/mL, about 4300 hr*ng/mL, about 4350 hr*ng/mL, about 4400 hr*ng/mL, about 4450 hr*ng/mL, about 4500 hr*ng/mL, about 4550 hr*ng/mL, about 4600 hr*ng/mL, about 4650 hr*ng/mL, about 4700 hr*ng/mL, about 4750 hr*ng/mL, about 4800 hr*ng/mL, about 4850 hr*ng/mL, about 4900 hr*ng/mL, about 4950 hr*ng/mL, about 5000 hr*ng/mL, about 5100 hr*ng/mL, about 5200 hr*ng/mL, about 5300 hr*ng/mL, about 5400 hr*ng/mL, about 5500 hr*ng/mL, about 5600 hr*ng/mL, about 5700 hr*ng/mL, about 5800 hr*ng/mL, about 5900 hr*ng/mL, about 6000 hr*ng/mL, about 6500 hr*ng/mL, about 7000 hr*ng/mL, about 7500 hr*ng/mL, about 8000 hr*ng/mL, about 8500 hr*ng/mL, about 9000 hr*ng/mL, about 9500 hr*ng/mL, about 10000 hr*ng/mL, about 11000 hr*ng/mL, about 12000 hr*ng/mL, about 13000 hr*ng/mL, about 14000 hr*ng/mL, about 15000 hr*ng/mL, about 16000 hr*ng/mL, about 17000 hr*ng/mL, about 18000 hr*ng/mL, about 19000 hr*ng/mL, or about 20000 hr*ng/mL, or any range therebetween.

In some embodiments, the resulted AUC of the plasma concentration for the β-lactam compound in the subject in need thereof at the seventh day of the administration is at about 100 hr*ng/mL, about 150 hr*ng/mL, about 200 hr*ng/mL, about 250 hr*ng/mL, about 300 hr*ng/mL, about 350 hr*ng/mL, about 400 hr*ng/mL, about 450 hr*ng/mL, about 500 hr*ng/mL, about 550 hr*ng/mL, about 600 hr*ng/mL, about 650 hr*ng/mL, about 700 hr*ng/mL, about 750 hr*ng/mL, about 800 hr*ng/mL, about 850 hr*ng/mL, about 900 hr*ng/mL, about 950 hr*ng/mL, about 1000 hr*ng/mL, about 1050 hr*ng/mL, about 1100 hr*ng/mL, about 1150 hr*ng/mL, about 1200 hr*ng/mL, about 1250 hr*ng/mL, about 1300 hr*ng/mL, about 1350 hr*ng/mL, about 1400 hr*ng/mL, about 1450 hr*ng/mL, about 1500 hr*ng/mL, about 1550 hr*ng/mL, about 1600 hr*ng/mL, about 1650 hr*ng/mL, about 1700 hr*ng/mL, about 1750 hr*ng/mL, about 1800 hr*ng/mL, about 1850 hr*ng/mL, about 1900 hr*ng/mL, about 1950 hr*ng/mL, about 2000 hr*ng/mL, about 2050 hr*ng/mL, about 2100 hr*ng/mL, about 2150 hr*ng/mL, about 2200 hr*ng/mL, about 2250 hr*ng/mL, about 2300 hr*ng/mL, about 2350 hr*ng/mL, about 2400 hr*ng/mL, about 2450 hr*ng/mL, about 2500 hr*ng/mL, about 2550 hr*ng/mL, about 2600 hr*ng/mL, about 2650 hr*ng/mL, about 2700 hr*ng/mL, about 2750 hr*ng/mL, about 2800 hr*ng/mL, about 2850 hr*ng/mL, about 2900 hr*ng/mL, about 2950 hr*ng/mL, about 3000 hr*ng/mL, about 3050 hr*ng/mL, about 3100 hr*ng/mL, about 3150 hr*ng/mL, about 3200 hr*ng/mL, about 3250 hr*ng/mL, about 3300 hr*ng/mL, about 3350 hr*ng/mL, about 3400 hr*ng/mL, about 3450 hr*ng/mL, about 3500 hr*ng/mL, about 3550 hr*ng/mL, about 3600 hr*ng/mL, about 3650 hr*ng/mL, about 3700 hr*ng/mL, about 3750 hr*ng/mL, about 3800 hr*ng/mL, about 3850 hr*ng/mL, about 3900 hr*ng/mL, about 3950 hr*ng/mL, about 4000 hr*ng/mL, about 4050 hr*ng/mL, about 4100 hr*ng/mL, about 4150 hr*ng/mL, about 4200 hr*ng/mL, about 4250 hr*ng/mL, about 4300 hr*ng/mL, about 4350 hr*ng/mL, about 4400 hr*ng/mL, about 4450 hr*ng/mL, about 4500 hr*ng/mL, about 4550 hr*ng/mL, about 4600 hr*ng/mL, about 4650 hr*ng/mL, about 4700 hr*ng/mL, about 4750 hr*ng/mL, about 4800 hr*ng/mL, about 4850 hr*ng/mL, about 4900 hr*ng/mL, about 4950 hr*ng/mL, about 5000 hr*ng/mL, about 5100 hr*ng/mL, about 5200 hr*ng/mL, about 5300 hr*ng/mL, about 5400 hr*ng/mL, about 5500 hr*ng/mL, about 5600 hr*ng/mL, about 5700 hr*ng/mL, about 5800 hr*ng/mL, about 5900 hr*ng/mL, about 6000 hr*ng/mL, about 6500 hr*ng/mL, about 7000 hr*ng/mL, about 7500 hr*ng/mL, about 8000 hr*ng/mL, about 8500 hr*ng/mL, about 9000 hr*ng/mL, about 9500 hr*ng/mL, about 10000 hr*ng/mL, about 11000 hr*ng/mL, about 12000 hr*ng/mL, about 13000 hr*ng/mL, about 14000 hr*ng/mL, about 15000 hr*ng/mL, about 16000 hr*ng/mL, about 17000 hr*ng/mL, about 18000 hr*ng/mL, about 19000 hr*ng/mL, or about 20000 hr*ng/mL, or any range therebetween.

Other Effects of the Methods

The method of the present disclosure may result in one or more additional effects to the subject in need thereof.

In some embodiments, the administration results a half life of the beta-lactam compound that is longer in the subject in need thereof as compared to a comparable subject being administered to the pharmaceutically effective amount of the β-lactam compound without probenecid over the period of time.

In some embodiments, the administration results a half life of the beta-lactam compound that is about 10%, about 20%, about 30%, about 40%, about 50%, about 60%, about 70%, about 80%, about 90%, about 100%, about 200%, about 300%, about 400%, or about 500% longer in the subject in need thereof as compared to a comparable subject being administered to the pharmaceutically effective amount of the β-lactam compound without probenecid over the period of time.

In some embodiments, the administration results a time over minimum inhibitory concentration (MIC) for the beta-lactam compound that is longer in the subject in need thereof as compared to a comparable subject being administered to the pharmaceutically effective amount of the β-lactam compound without probenecid over the period of time.

In some embodiments, the administration results a time over MIC for the beta-lactam compound that is about 10%, about 20%, about 30%, about 40%, about 50%, about 60%, about 70%, about 80%, about 90%, about 100%, about 200%, about 300%, about 400%, or about 500% longer in the subject in need thereof as compared to a comparable subject being administered to the pharmaceutically effective amount of the β-lactam compound without probenecid over the period of time.

In some embodiments, the administration of the probenecid or a pharmaceutically acceptable salt thereof does not substantially increase the elimination rate of the β-lactam compound or a pharmaceutically acceptable salt thereof in the subject in need thereof.

In some embodiments, the elimination rate of the β-lactam compound or a pharmaceutically acceptable salt thereof in the subject in need thereof is about 150% or less, about 120% or less, about 110% or less, about 105% or less, about 103% or less, or about 101% or less, as compared to the comparable subject.

In some embodiments, the elimination rate of the β-lactam compound or a pharmaceutically acceptable salt thereof in the subject in need thereof is about the same as compared to the comparable subject.

In some embodiments, the administration of the probenecid or a pharmaceutically acceptable salt thereof enhances the absorption rate of the β-lactam compound or a pharmaceutically acceptable salt thereof in the subject in need thereof.

In some embodiments, the absorption rate of the β-lactam compound or a pharmaceutically acceptable salt thereof in the subject in need thereof is higher as compared to the comparable subject an amount ranging from about 2% to about 100%, from about 4% to about 80%, from about 6% to about 60%, from about 8% to about 40%, from about 10% to about 30%, from about 12% to about 25%, or from about 15% to about 20%.

Treated Subjects and Diseases

In some embodiments, the subject in need thereof is an animal. In some embodiments, the subject in need thereof is a human.

In some embodiments, the subject in need thereof is a human of 18 years or older.

In some embodiments, the subject in need thereof is a human younger than 18 years.

In some embodiments, the disease is associated with an increased or decreased population of one or more microorganisms (e.g., bacteria) in the subject.

In some embodiments, the disease is associated with an increased population of one or more microorganisms (e.g., bacteria) in the subject. In some embodiments, the method of the present disclosure results in a decrease population of the one or more microorganisms (e.g., bacteria) in the subject.

In some embodiments, the disease is associated with a decreased population of one or more microorganisms (e.g., bacteria) in the subject. In some embodiments, the method of the present disclosure results in an increased population of the one or more microorganisms (e.g., bacteria) in the subject.

In some embodiments, the disease is associated with an increased or decreased population of one or more bacteria selected from *Escherichia coli, Klebsiella pneumoniae, Proteus mirabilis, Enterobacter cloacae, Klebsiella oxytoca, Citrobacter freundii* complex, *Clostridium clostridioforme, Eubacterium lentum, Peptostreptococcus* species, *Bacteroides fragilis, Bacteroides distasonis, Bacteroides ovatus, Bacteroides thetaiotaomicron, Bacteroides uniformis, Bacteroides coprocola, Prevotella copri, Porphyromonas asaccharolytica,* and *Prevotella bivia* or any organisms in the following genera: *Succinivibrio, Alistipes, Prevotella, Paraprevotella, Parabacteroides,* and *Odoribacter.*

In some embodiments, the disease is associated with an increased or decreased population of one or more bacteria selected from *Staphylococcus epidermidis, Streptococcus* pneumonia, *Staphylococcus aureus, Streptococcus agalactiae*, and *Streptococcus pyogenes*.

In some embodiments, the disease is associated with an increased or decreased population of one or more bacteria selected from *Citrobacter freundii, Citrobacter koseri, Enterobacter aerogenes, Enterobacter cloacae, Haemophilus influenza, Haemophilus parainfluenzae, Klebsiella oxytoca, Moraxella catarrhalis, Morganella morganii, Proteus vulgaris, Providencia rettgeri, Providencia stuartii,* and *Serratia marcescens*.

In some embodiments, the disease is associated with an increased or decreased population of one or more bacteria selected from *Bacteroides vulgatus, Clostridium perfringens,* and *Fusobacterium* spp.

In some embodiments, the disease is associated with an infection. In some embodiments, the infection is a gram-negative infection. In some embodiments, the infection is a gram-positive infection.

In some embodiments, the infection is resistant to one or more antibiotics when being administered without probenecid or the pharmaceutically acceptable salt thereof.

In some embodiments, the infection is resistant to one or more β-lactam compounds when being administered without probenecid or the pharmaceutically acceptable salt thereof.

In some embodiments, the disease is an uncomplicated urinary tract infection, a complicated urinary tract infection, a complicated intra-abdominal infection, an uncomplicated intra-abdominal infection, pneumonia, otitis media, sinusitis, gonococcal urethritis, pelvic inflammatory disease, prostatitis, bone infection, joint infection, diabetic foot infection and infectious diarrhea.

In some embodiments, the disease is associated with (e.g., resulted from) the alteration of the microbiome in the subject.

In some embodiments, the disease is associated with (e.g., resulted from) the alteration of the microbiome in the human subject.

In some embodiments, the disease is a neurodegenerative disease.

In some embodiments, the disease is amyotrophic lateral sclerosis, Parkinson's disease, Alzheimer's disease, schizophrenia or Huntington's disease.

In some embodiments, the disease is Alzheimer's disease. It is noted that probenecid has been found to increase the concentrations of β-lactam compounds in the cerebrospinal fluid (Ralph G. Dacey and Merle A. Sande, *Antimicrobial Agents and Chemotherapy* 6:437-441 (1974)). More recently, a bacterial pathogen, *Porphyromonas gingivalis*, has been found in brain in association with pathologic lesions, which are associated with Alzheimer's disease (Dominy et al., *Sci. Adv.* 5:eaau3333 (2019), and sulopenem is active against this bacterium (Lois M. Ednie and Peter C. Appelbaum, *Antimicrobial Agents and Chemotherapy* 53: 2163-2170 (2009)). Without wishing to be bound by theory, it is understood that the beta-lactam compounds (e.g., Compound III-2b), when being dosed with probenecid, may lead to more effective treatment of a brain infection with this organism relative to treatment with sulopenem alone.

In some embodiments, the disease is cancer.

In some embodiments, the cancer is a solid cancer, e.g., ovarian cancer, breast cancer, head and neck cancer, renal cancer, bladder cancer, hepatocellular cancer, colorectal cancer, or lymphoma, or any combination thereof.

In some embodiments, the cancer is sarcoma or carcinoma, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, hepatoma, bile duct carcinoma, choriocarcinoma, seminoma, embryonal carcinoma, Wilms' tumor, cervical cancer, testicular tumor, lung carcinoma, small cell lung carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma.

In some embodiments, the cancer is leukemia, e.g., acute lymphocytic leukemia and acute myelocytic leukemia (myeloblastic, promyelocytic, myelomonocytic, monocytic and erythroleukemia); or chronic leukemia (chronic myelocytic (granulocytic) leukemia and chronic lymphocytic leukemia).

In some embodiments, the cancer is polycythemia vera, lymphoma (Hodgkin's disease and non-Hodgkin's disease), multiple myeloma, Waldenström's macroglobulinemia, or heavy chain disease.

In some embodiments, the disease is an inflammatory bowel disease.

In some embodiments, the inflammatory bowel disease is Crohn's disease, ulcerative colitis, indeterminate colitis, irritable bowel syndrome, microscopic colitis, deversion colitis, or Behcet's disease.

β-Lactam Compounds

In some embodiments, the β-lactam compound is a monobactam or a prodrug thereof.

In some embodiments, the β-lactam compound is aztreonam, tigemonam, carumonam, nocardicin A, a prodrug thereof, an analog thereof, or a derivative thereof.

In some embodiments, the β-lactam compound is a penem, a carbapenem, a clavam, or a prodrug thereof.

In some embodiments, the β-lactam compound is benzylpenicillin, benzathine benzylpenicillin, procaine benzylpenicillin, phenoxymethylpenicillin, propicillin, pheneticillin, azidocillin, clometocillin, penamecillin, cloxacillin (e.g., dicloxacillin or flucloxacillin), oxacillin, nafcillin, methicillin, amoxicillin, ampicillin (e.g., pivampicillin, hetacillin, bacampicillin, metampicillin, talampicillin), epicillin, ticarcillin, carbenicillin, carindacillin, temocillin, piperacillin, azlocillin, mezlocillin, mecillinam (e.g., pivmecillinam), sulbenicillin, a pharmaceutically acceptable salt thereof, a prodrug thereof, an analog thereof, or a derivative thereof.

In some embodiments, the β-lactam compound is a penem, a carbapenem, or a prodrug thereof.

In some embodiments, the β-lactam compound a thiopenem, an oxypenem, an aminopenem, an alkylpenems, an arylpenem, or a prodrug thereof.

In some embodiments, the β-lactam compound is ertapenem, an antipseudomonal carbapenem (e.g., doripenem, imipenem, meropenem), biapenem, panipenem, sulopenem, tebipenem, faropenem, a pharmaceutically acceptable salt thereof, a prodrug thereof, an analog thereof, or a derivative thereof.

In some embodiments, the β-lactam compound is a cephem, a carbacephem, an oxacephem, or a prodrug thereof.

In some embodiments, the β-lactam compound is cefazolin, cefalexin, cefadroxil, cefapirin, cefazedone, cefazaflur, cefradine, cefroxadine, ceftezole, cefaloglycin, cefacetrile, cefalonium, cefaloridine, cefalotin, cefatrizine, cefaclor, cefotetan, cephamycin (e.g., cefoxitin, cefprozil, cefuroxime, cefuroxime axetil, cefamandole, cefminox, cefonicid, ceforanide, cefotiam, cefbuperazone, cefuzonam, cefmetazole), carbacephem (e.g., loracarbef), cefixime, ceftriaxone, antipseudomonal (e.g, ceftazidime, cefoperazone), cefdinir, cefcapene, cefdaloxime, ceftizoxime, cefmenoxime, cefotaxime, cefpiramide, cefpodoxime, ceftibuten, cefditoren, cefetamet, cefodizime, cefpimizole, cefsulodin, cefteram, ceftiolene, oxacephem (e.g., flomoxef, latamoxef), cefepime, cefozopran, cefpirome, cefquinome, ceftaroline fosamil, ceftolozane, ceftobiprole, ceftiofur, cefquinome, cefovecin, a pharmaceutically acceptable salt thereof, a prodrug thereof, an analog thereof, or a derivative thereof.

In some embodiments, the β-lactam compound is a thiopenem or a prodrug thereof.

In some embodiments, the β-lactam compound is of Formula (I):

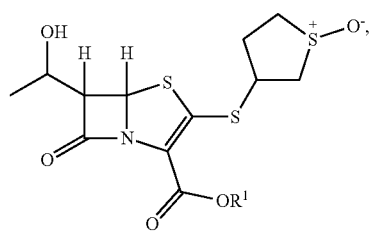

(I)

a pharmaceutically acceptable salt thereof, a prodrug thereof, an analog thereof, or a derivative thereof, wherein $R^1$ is H or optionally substituted alkyl.

In some embodiments, the β-lactam compound is of Formula (Ia):

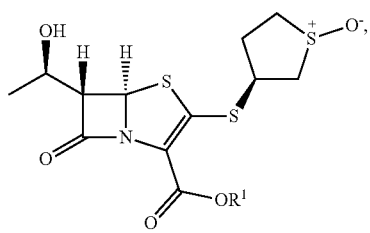

(Ia)

a pharmaceutically acceptable salt thereof, a prodrug thereof, an analog thereof, or a derivative thereof.

In some embodiments, the β-lactam compound is of Formula (Ib):

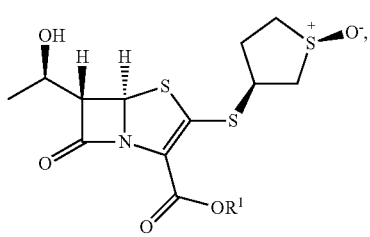

(Ib)

a pharmaceutically acceptable salt thereof, a prodrug thereof, an analog thereof, or a derivative thereof.

In some embodiments, $R^1$ is H.

In some embodiments, the β-lactam compound is of Formula (II):

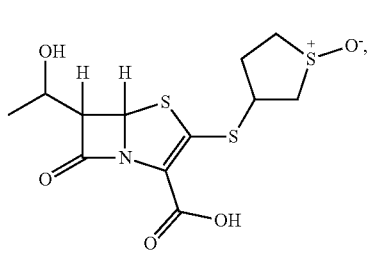

(II)

a pharmaceutically acceptable salt thereof, a prodrug thereof, an analog thereof, or a derivative thereof.

In some embodiments, the β-lactam compound is of Formula (IIa):

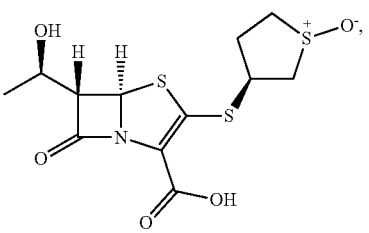

(IIa)

a pharmaceutically acceptable salt thereof, a prodrug thereof, an analog thereof, or a derivative thereof.

In some embodiments, the β-lactam compound is of Formula (IIb):

(IIb)

a pharmaceutically acceptable salt thereof, a prodrug thereof, an analog thereof, or a derivative thereof.

In some embodiments, $R^1$ is optionally substituted alkyl.

In some embodiments, the β-lactam compound is of any one of Formulae (III), (IIIa), and (IIIb):

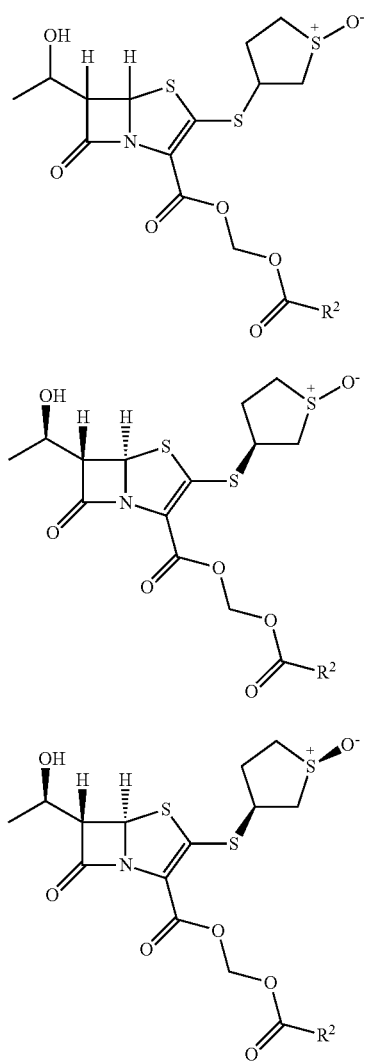

(III)

(IIIa)

(IIIb)

a pharmaceutically acceptable salt thereof, a prodrug thereof, an analog thereof, or a derivative thereof, wherein R² is H or optionally substituted alkyl.

In some embodiments, the β-lactam compound is selected from the group consisting of:

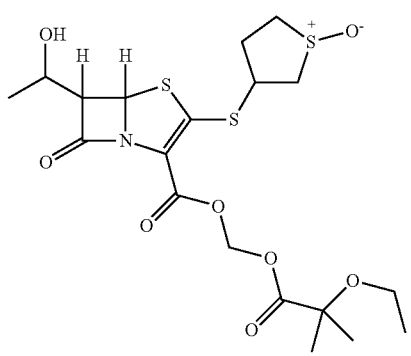

(Compound III-1)

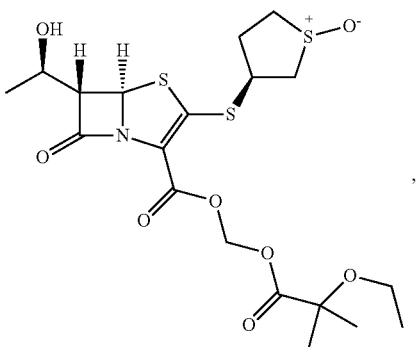

(Compound III-1a)

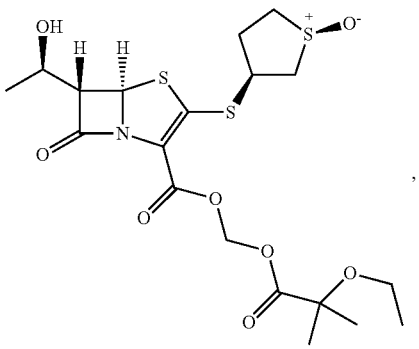

(Compound III-1b)

pharmaceutically acceptable salts thereof, prodrugs thereof, analogs thereof, and derivatives thereof.

In some embodiments, the β-lactam compound is selected from the group consisting of:

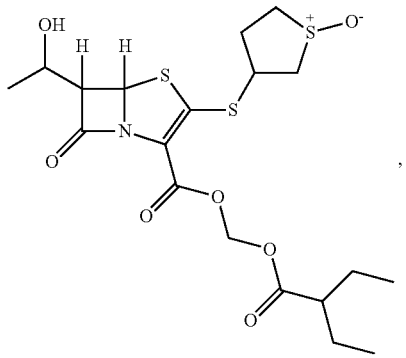

(Compound III-2)

-continued

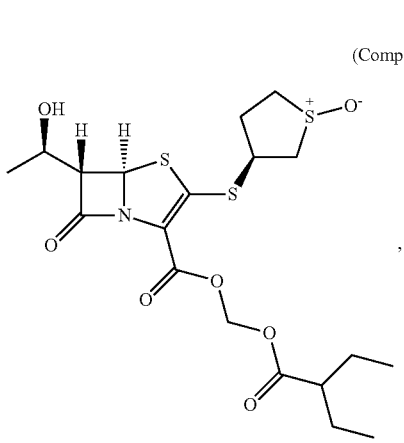
(Compound III-2a)

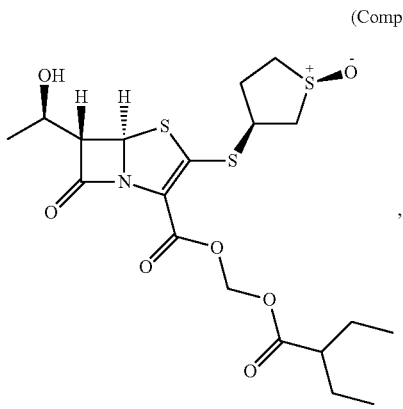
(Compound III-2b)

pharmaceutically acceptable salts thereof, prodrugs thereof, analogs thereof, and derivatives thereof.

In some embodiments, the β-lactam compound is selected from

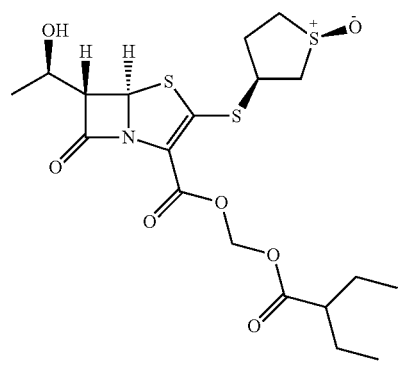

(Compound III-2b; also known as Sulopenem Etzadroxil), pharmaceutically acceptable salts thereof, prodrugs thereof, analogs thereof, and derivatives thereof.

In some embodiments, the β-lactam compound is

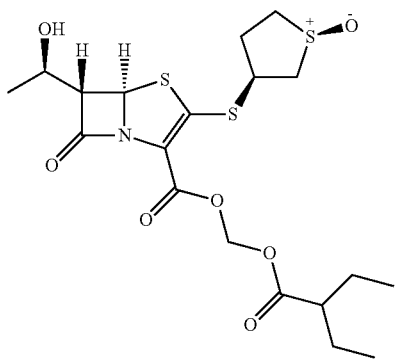

(Compound III-2b; also known as Sulopenem Etzadroxil).

In some embodiments, the β-lactam compound is of any one of Formulae (IV), (IVa), and (IVb):

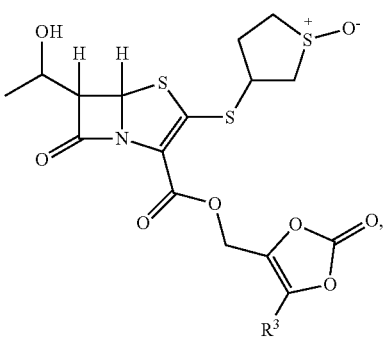
(IV)

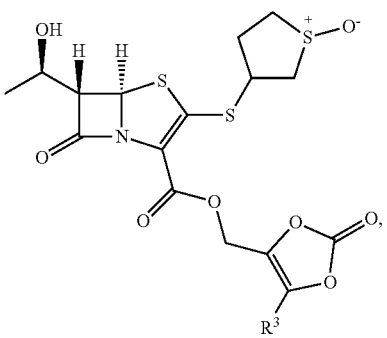
(IVa)

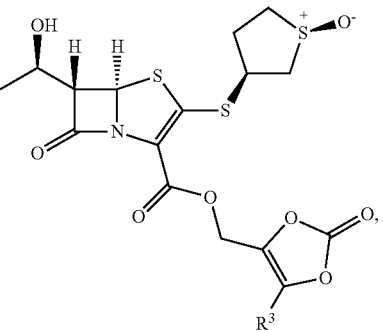
(IVb)

a pharmaceutically acceptable salt thereof, a prodrug thereof, an analog thereof, or a derivative thereof, wherein $R^3$ is H or optionally substituted alkyl.

In some embodiments, $R^3$ is $C_2$-$C_8$ alkyl.

In some embodiments, $R^3$ is $CH_2CH_3$, $CH_2CH_2CH_3$, or $CH_2CH(CH_3)_2$.

Administrations of β-Lactam Compounds and Probenecid

In some embodiments, the β-lactam compound or the pharmaceutically acceptable salt thereof and probenecid or the pharmaceutically acceptable salt thereof are administered simultaneously.

In some embodiments, the β-lactam compound or the pharmaceutically acceptable salt thereof and probenecid or the pharmaceutically acceptable salt thereof are both administered by enteral administration.

In some embodiments, the enteral administration is oral administration.

In some embodiments, an oral co-formulation comprising the β-lactam compound or the pharmaceutically acceptable salt thereof and probenecid or the pharmaceutically acceptable salt thereof is administered.

In some embodiments, a tablet comprising the β-lactam compound or the pharmaceutically acceptable salt thereof and probenecid or the pharmaceutically acceptable salt thereof is administered.

In some embodiments, the β-lactam compound or the pharmaceutically acceptable salt thereof and probenecid or the pharmaceutically acceptable salt thereof are both administered in separate oral formulations.

In some embodiments, the β-lactam compound or the pharmaceutically acceptable salt thereof and probenecid or the pharmaceutically acceptable salt thereof are both administered in separate tablets.

In some embodiments, the β-lactam compound or the pharmaceutically acceptable salt thereof and probenecid or the pharmaceutically acceptable salt thereof are both administered by parenteral administration.

In some embodiments, the parenteral administration is intravenous administration.

In some embodiments, the β-lactam compound or the pharmaceutically acceptable salt thereof and probenecid or the pharmaceutically acceptable salt thereof are administered in a co-formulation.

In some embodiments, the co-formulation is administered to the subject one or more times daily.

In some embodiments, the co-formulation is an oral co-formulation (e.g., a tablet).

In some embodiments, the oral co-formulation comprises:
from 20 mg to about 5 g, from about 50 mg to about 2 g, from about 80 mg to about 1 g, from about 100 mg to about 900 mg, from about 200 mg to about 800 mg, from about 300 mg to about 700 mg, from about 400 mg to about 600 mg, from about 450 mg to about 550 mg, or from about 480 mg to about 520 mg of the β-lactam compound or the pharmaceutically acceptable salt thereof; and
from 20 mg to about 5 g, from about 50 mg to about 2 g, from about 80 mg to about 1 g, from about 100 mg to about 900 mg, from about 200 mg to about 800 mg, from about 300 mg to about 700 mg, from about 400 mg to about 600 mg, from about 450 mg to about 550 mg, or from about 480 mg to about 520 mg of probenecid or the pharmaceutically acceptable salt thereof.

In some embodiments, the oral co-formulation comprises about 500 mg of the β-lactam compound or the pharmaceutically acceptable salt thereof and about 500 mg of probenecid or the pharmaceutically acceptable salt thereof.

In some embodiments, the oral co-formulation is administered to the subject once daily, two times daily, three times daily, or four times daily for about 1 day, about 2 days, about 3 days, about 4 days, about 5 days, about 6 days, about 7 days, about 14 days, about 21 days, or about 28 days.

In some embodiments, the oral co-formulation is administered to the subject two times daily for about 5 days.

In some embodiments, the β-lactam compound or the pharmaceutically acceptable salt thereof and probenecid or the pharmaceutically acceptable salt thereof are administered in separate formulations.

In some embodiments, the β-lactam compound or the pharmaceutically acceptable salt thereof and probenecid or the pharmaceutically acceptable salt thereof are administered simultaneously, sequentially, or in alternation.

In some embodiments, the β-lactam compound or the pharmaceutically acceptable salt thereof and probenecid or the pharmaceutically acceptable salt thereof are administered simultaneously.

In some embodiments, the β-lactam compound or the pharmaceutically acceptable salt thereof and probenecid or the pharmaceutically acceptable salt thereof are administered sequentially.

In some embodiments, the β-lactam compound or the pharmaceutically acceptable salt thereof and probenecid or the pharmaceutically acceptable salt thereof are administered in temporal proximity.

In some embodiments, the β-lactam compound or the pharmaceutically acceptable salt thereof is administered prior to the administration of probenecid or the pharmaceutically acceptable salt thereof.

In some embodiments, probenecid or the pharmaceutically acceptable salt thereof is administered prior to the administration of the β-lactam compound or the pharmaceutically acceptable salt thereof.

In some embodiments, the β-lactam compound or the pharmaceutically acceptable salt thereof and probenecid or the pharmaceutically acceptable salt thereof are administered or in alternation.

In some embodiments, the β-lactam compound or the pharmaceutically acceptable salt thereof is administered one or more times daily at a daily dosage ranging from about 20 mg to about 5 g, from about 50 mg to about 2 g, from about 80 mg to about 1 g, from about 100 mg to about 900 mg, from about 200 mg to about 800 mg, from about 300 mg to about 700 mg, from about 400 mg to about 600 mg, from about 450 mg to about 550 mg, or from about 480 mg to about 520 mg.

In some embodiments, the β-lactam compound or the pharmaceutically acceptable salt thereof is administered one or more times daily at a daily dosage at about 500 mg.

In some embodiments, the β-lactam compound or the pharmaceutically acceptable salt thereof is administered one or more times daily at a daily dosage ranging from about 50 mg to about 10 g, from about 100 mg to about 5 g, from about 200 mg to about 3 g, from about 400 mg to about 2 g, from about 600 mg to about 1.5 g, from about 800 mg to about 1.2 g, or from about 900 mg to about 1.1 g.

In some embodiments, the β-lactam compound or the pharmaceutically acceptable salt thereof is administered one or more times daily at a daily dosage at about 1 g.

In some embodiments, the β-lactam compound or the pharmaceutically acceptable salt thereof is administered one or more times daily at a daily dosage ranging from about 100 mg to about 10 g, from about 200 mg to about 5 g, from about 500 mg to about 3 g, from about 800 mg to about 2.5 g, from about 1 g to about 2 g, from about 1.2 g to about 1.8 g, or from about 1.4 g to about 1.6 g.

In some embodiments, the β-lactam compound or the pharmaceutically acceptable salt thereof is administered on or more times daily at a daily dosage at about 1.5 g.

In some embodiments, the β-lactam compound or the pharmaceutically acceptable salt thereof is administered once daily.

In some embodiments, the β-lactam compound or the pharmaceutically acceptable salt thereof is administered twice daily.

In some embodiments, the β-lactam compound or the pharmaceutically acceptable salt thereof is administered three or more times daily.

In some embodiments, the β-lactam compound or the pharmaceutically acceptable salt thereof is administered continuously.

In some embodiments, the β-lactam compound or the pharmaceutically acceptable salt thereof is administered for more than about 1 day.

In some embodiments, the β-lactam compound or the pharmaceutically acceptable salt thereof is administered for about 2 days, about 3 days, about 4 days, about 5 days, about 6 days, about 7 days, about 14 days, or about 30 days.

In some embodiments, the β-lactam compound or the pharmaceutically acceptable salt thereof is administered with one or more drug holidays.

In some embodiments, the β-lactam compound or the pharmaceutically acceptable salt thereof is administered without any drug holiday.

In some embodiments, the β-lactam compound or the pharmaceutically acceptable salt thereof is administered by an enteral administration.

In some embodiments, the β-lactam compound or the pharmaceutically acceptable salt thereof is administered by an oral administration or a rectum administration.

In some embodiments, the β-lactam compound or the pharmaceutically acceptable salt thereof is administered by an oral administration.

In some embodiments, the β-lactam compound or the pharmaceutically acceptable salt thereof is administered by a parenteral administration.

In some embodiments, the β-lactam compound or the pharmaceutically acceptable salt thereof is administered by an intravenous administration. In some embodiments, an injectable formulation of the β-lactam compound or the pharmaceutically acceptable salt thereof is administered to the subject.

In some embodiments, the injectable formulation is an intravenous infusion.

In some embodiments, the injectable formulation comprises about 50 mg to about 10 g, from about 100 mg to about 5 g, from about 200 mg to about 3 g, from about 400 mg to about 2 g, from about 600 mg to about 1.5 g, from about 800 mg to about 1.2 g, or from about 900 mg to about 1.1 g of the β-lactam compound or the pharmaceutically acceptable salt thereof.

In some embodiments, the injectable formulation comprises about 1 g of the β-lactam compound or the pharmaceutically acceptable salt thereof.

In some embodiments, the injectable formulation is administered to the subject by intravenous infusion over about 30 minutes, about 1 hour, about 2 hours, about 3 hours, about 4 hours, about 6 hours, or about 12 hours.

In some embodiments, the injectable formulation is administered to the subject by intravenous infusion over about 3 hours.

In some embodiments, the injectable formulation is administered to the subject once every 6 hours, once every 12 hours, once every 24 hours, once every hours, or once ever 48 hours, for from about 1 day to about 30 days, from about 2 days to about 28 days, from about 3 days to about 24 days, from about 4 days to about 21 days, from about 5 days to about 18 days, from about 6 days to about 15 days, or from about 7 days to about 14 days.

In some embodiments, the injectable formulation is administered to the subject once every 24 hours for about 7 days, about 8 days, about 9 days, about 10 days, about 11 days, about 12 days, about 13 days, or about 14 days.

In some embodiments, the subject has renal impairment, and wherein:
  the injectable formulation comprises from about 10 mg to about 2 g, from about 25 mg to about 1 g, from about 40 mg to about 500 mg, from about 50 mg to about 450 mg, from about 100 mg to about 400 mg, from about 150 mg to about 350 mg, from about 200 mg to about 300 mg, from about 225 mg to about 275 mg, or from about 240 mg to about 260 mg of the β-lactam compound or the pharmaceutically acceptable salt thereof;
  the injectable formulation is administered to the subject by intravenous infusion over about 30 minutes, about 1 hour, about 2 hours, about 3 hours, about 4 hours, about 6 hours, or about 12 hours; and
  the injectable formulation is administered to the subject once every 6 hours, once every 12 hours, once every 24 hours, once every hours, or once ever 48 hours.

In some embodiments, the subject has renal impairment, and wherein:
  the injectable formulation comprises about 250 mg of the β-lactam compound or the pharmaceutically acceptable salt thereof;
  the injectable formulation is administered to the subject once every 24 hours by intravenous infusion over about 3 hours.

In some embodiments, the subject in need thereof is not fasted within about 1 hour, about 2 hours, about 3 hours, about 6 hours, about 12 hours, about 24 hours, about 2 days, about 5 days, or about 10 days prior to administration of the β-lactam compound or the pharmaceutically acceptable salt thereof.

In some embodiments, the subject in need thereof is fasted for about 1 hour, about 2 hours, ab out 3 hours, about 6 hours, about 12 hours, about 24 hours, about 2 days, about 5 days, or about 10 days prior to administration of the β-lactam compound or the pharmaceutically acceptable salt thereof.

In some embodiments, the subject in need thereof is not fasted within about 1 hour, about 2 hours, ab out 3 hours, about 6 hours, about 12 hours, about 24 hours, about 2 days, about 5 days, or about 10 days after administration of the β-lactam compound or the pharmaceutically acceptable salt thereof.

In some embodiments, the subject in need thereof is fasted for about 1 hour, about 2 hours, ab out 3 hours, about 6 hours, about 12 hours, about 24 hours, about 2 days, about 5 days, or about 10 days after administration of the β-lactam compound or the pharmaceutically acceptable salt thereof.

In some embodiments, the probenecid or the pharmaceutically acceptable salt thereof is administered one or more times daily at a daily dosage ranging from about 20 mg to about 5 g, from about 50 mg to about 2 g, from about 80 mg to about 1 g, from about 100 mg to about 900 mg, from about 200 mg to about 800 mg, from about 300 mg to about 700 mg, from about 400 mg to about 600 mg, from about 450 mg to about 550 mg, or from about 480 mg to about 520 mg.

In some embodiments, the probenecid or the pharmaceutically acceptable salt thereof is administered one or more times daily at a daily dosage at about 500 mg.

In some embodiments, the probenecid or the pharmaceutically acceptable salt thereof is administered one or more times daily at a daily dosage ranging from about 50 mg to about 10 g, from about 100 mg to about 5 g, from about 200 mg to about 3 g, from about 400 mg to about 2 g, from about 600 mg to about 1.5 g, from about 800 mg to about 1.2 g, or from about 900 mg to about 1.1 g.

In some embodiments, the probenecid or the pharmaceutically acceptable salt thereof is administered one or more times daily at a daily dosage at about 1 g.

In some embodiments, the probenecid or the pharmaceutically acceptable salt thereof is administered one or more times daily at a daily dosage ranging from about 100 mg to about 10 g, from about 200 mg to about 5 g, from about 500 mg to about 3 g, from about 800 mg to about 2.5 g, from about 1 g to about 2 g, from about 1.2 g to about 1.8 g, or from about 1.4 g to about 1.6 g.

In some embodiments, the probenecid or the pharmaceutically acceptable salt thereof is administered one or more times daily at a daily dosage at about 1.5 g.

In some embodiments, the probenecid or the pharmaceutically acceptable salt thereof is administered once daily.

In some embodiments, the probenecid or the pharmaceutically acceptable salt thereof is administered twice daily.

In some embodiments, the probenecid or the pharmaceutically acceptable salt thereof is administered three or more times daily.

In some embodiments, the probenecid or the pharmaceutically acceptable salt thereof is administered continuously.

In some embodiments, the probenecid or the pharmaceutically acceptable salt thereof is administered for more than about 1 day.

In some embodiments, the probenecid or the pharmaceutically acceptable salt thereof is administered for about 2 days, about 3 days, about 4 days, about 5 days, about 6 days, about 7 days, about 14 days, or about 30 days.

In some embodiments, the probenecid or the pharmaceutically acceptable salt thereof is administered with one or more drug holidays.

In some embodiments, the probenecid or the pharmaceutically acceptable salt thereof is administered without any drug holiday.

In some embodiments, the probenecid or the pharmaceutically acceptable salt thereof is administered by an enteral administration.

In some embodiments, the probenecid or the pharmaceutically acceptable salt thereof is administered by an oral administration or a rectum administration.

In some embodiments, the probenecid or the pharmaceutically acceptable salt thereof is administered by an oral administration.

In some embodiments, the probenecid or the pharmaceutically acceptable salt thereof is administered by a parenteral administration.

In some embodiments, the probenecid or the pharmaceutically acceptable salt thereof is administered by an intravenous administration.

In some embodiments, the subject in need thereof is not fasted within about 1 hour, about 2 hours, about 3 hours, about 6 hours, about 12 hours, about 24 hours, about 2 days, about 5 days, or about 10 days prior to administration of the probenecid or the pharmaceutically acceptable salt thereof.

In some embodiments, the subject in need thereof is fasted for about 1 hour, about 2 hours, about 3 hours, about 6 hours, about 12 hours, about 24 hours, about 2 days, about 5 days, or about 10 days prior to administration of the probenecid or the pharmaceutically acceptable salt thereof.

In some embodiments, the subject in need thereof is not fasted within about 1 hour, about 2 hours, about 3 hours, about 6 hours, about 12 hours, about 24 hours, about 2 days, about 5 days, or about 10 days after administration of the probenecid or the pharmaceutically acceptable salt thereof.

In some embodiments, the subject in need thereof is fasted for about 1 hour, about 2 hours, about 3 hours, about 6 hours, about 12 hours, about 24 hours, about 2 days, about 5 days, or about 10 days after administration of the probenecid or the pharmaceutically acceptable salt thereof.

Alternatives Uses of β-Lactam Compounds and Probenecids

In some aspects, the present disclosure provides a β-lactam compound or a pharmaceutically acceptable salt thereof for use in combination with probenecid or a pharmaceutically acceptable salt thereof in treating or preventing a disease in a subject in need thereof, wherein the β-lactam compound or the pharmaceutically acceptable salt thereof and probenecid or the pharmaceutically acceptable salt thereof are administered to the subject by the same administration route.

In some aspects, the present disclosure provides probenecid or a pharmaceutically acceptable salt thereof for use in combination with a β-lactam compound or a pharmaceutically acceptable salt thereof in treating or preventing a disease in a subject in need thereof, wherein the β-lactam compound or the pharmaceutically acceptable salt thereof and probenecid or the pharmaceutically acceptable salt thereof are administered to the subject by the same administration route.

In some aspects, the present disclosure provides a combination of a β-lactam compound or a pharmaceutically acceptable salt thereof and probenecid or a pharmaceutically acceptable salt thereof for use in treating or preventing a disease in a subject in need thereof, wherein the β-lactam compound or the pharmaceutically acceptable salt thereof and probenecid or the pharmaceutically acceptable salt thereof are administered to the subject by the same administration route.

In some aspects, the present disclosure provides use of a β-lactam compound in combination with probenecid or a pharmaceutically acceptable salt thereof in the manufacture of a medicament for treating or preventing a disease in a subject in need thereof, wherein the β-lactam compound or the pharmaceutically acceptable salt thereof and probenecid or the pharmaceutically acceptable salt thereof are administered to the subject by the same administration route.

In some aspects, the present disclosure provides use of probenecid in combination with a β-lactam compound or a pharmaceutically acceptable salt thereof in the manufacture of a medicament for treating or preventing a disease in a subject in need thereof, wherein the β-lactam compound or the pharmaceutically acceptable salt thereof and probenecid or the pharmaceutically acceptable salt thereof are administered to the subject by the same administration route.

In some aspects, the present disclosure provides use of a combination of a β-lactam compound or a pharmaceutically acceptable salt thereof and probenecid or a pharmaceutically acceptable salt thereof in the manufacture of a medicament for treating or preventing a disease in a subject in need thereof, wherein the β-lactam compound or the pharmaceutically acceptable salt thereof and probenecid or the pharmaceutically acceptable salt thereof are administered to the subject by the same administration route.

In some aspects, the present disclosure provides a β-lactam compound or a pharmaceutically acceptable salt thereof for use in combination with probenecid or a pharmaceutically acceptable salt thereof in treating or preventing a disease, wherein:
   the β-lactam compound or the pharmaceutically acceptable salt thereof and the probenecid or a pharmaceutically acceptable salt thereof are administered to a subject in need over a period of time, wherein the administration results in a plasma concentration for the β-lactam compound having:
   an area under the curve (AUC) that is higher in the subject in need thereof as compared to a comparable subject being administered to the pharmaceutically effective amount of the β-lactam compound without probenecid over the period of time,
   a maximum plasma concentration ($C_{max}$) that is higher in the subject in need thereof as compared to the comparable subject being administered to the pharmaceutically effective amount of the β-lactam compound without probenecid over the period of time, or
   a combination thereof.

In some aspects, the present disclosure provides probenecid or a pharmaceutically acceptable salt thereof for use in combination with a β-lactam compound or a pharmaceutically acceptable salt thereof in treating or preventing a disease, wherein:
   the β-lactam compound or the pharmaceutically acceptable salt thereof and the probenecid or a pharmaceutically acceptable salt thereof are administered to a subject in need over a period of time, wherein the administration results in a plasma concentration for the β-lactam compound having:
   an area under the curve (AUC) that is higher in the subject in need thereof as compared to a comparable subject being administered to the pharmaceutically effective amount of the β-lactam compound without probenecid over the period of time,
   a maximum plasma concentration ($C_{max}$) that is higher in the subject in need thereof as compared to the comparable subject being administered to the pharmaceutically effective amount of the β-lactam compound without probenecid over the period of time, or
   a combination thereof.

In some aspects, the present disclosure provides a combination of a β-lactam compound or a pharmaceutically acceptable salt thereof and probenecid or a pharmaceutically acceptable salt thereof for use in treating or preventing a disease, wherein:
   the β-lactam compound or the pharmaceutically acceptable salt thereof and the probenecid or a pharmaceutically acceptable salt thereof are administered to a subject in need over a period of time, wherein the administration results in a plasma concentration for the β-lactam compound having:
   an area under the curve (AUC) that is higher in the subject in need thereof as compared to a comparable subject being administered to the pharmaceutically effective amount of the β-lactam compound without probenecid over the period of time,
   a maximum plasma concentration ($C_{max}$) that is higher in the subject in need thereof as compared to the comparable subject being administered to the pharmaceutically effective amount of the β-lactam compound without probenecid over the period of time, or
   a combination thereof.

In some aspects, the present disclosure provides use of a β-lactam compound or a pharmaceutically acceptable salt thereof in combination with probenecid or a pharmaceutically acceptable salt thereof in the manufacture of a medicament for treating or preventing a disease, wherein administration of the medicament to a subject in need over a period of time results in a plasma concentration for the β-lactam compound having:
   an area under the curve (AUC) that is higher in the subject in need thereof as compared to a comparable subject being administered to the pharmaceutically effective amount of the β-lactam compound without probenecid over the period of time,
   a maximum plasma concentration ($C_{max}$) that is higher in the subject in need thereof as compared to the comparable subject being administered to the pharmaceutically effective amount of the β-lactam compound without probenecid over the period of time, or
   a combination thereof.

In some aspects, the present disclosure provides use of probenecid or a pharmaceutically acceptable salt thereof in combination with a β-lactam compound or a pharmaceutically acceptable salt thereof in the manufacture of a medicament for treating or preventing a disease, wherein administration of the medicament to a subject in need over a period of time results in a plasma concentration for the β-lactam compound having:
   an area under the curve (AUC) that is higher in the subject in need thereof as compared to a comparable subject being administered to the pharmaceutically effective amount of the β-lactam compound without probenecid over the period of time,
   a maximum plasma concentration ($C_{max}$) that is higher in the subject in need thereof as compared to the comparable subject being administered to the pharmaceutically effective amount of the β-lactam compound without probenecid over the period of time, or
   a combination thereof.

In some aspects, the present disclosure provides use of a combination of a β-lactam compound or a pharmaceutically acceptable salt thereof and probenecid or a pharmaceutically acceptable salt thereof in the manufacture of a medicament for treating or preventing a disease, wherein administration of the medicament to a subject in need over a period of time results in a plasma concentration for the β-lactam compound having:
   the β-lactam compound or the pharmaceutically acceptable salt thereof and the probenecid or a pharmaceutically acceptable salt thereof are administered to a subject in need over a period of time, wherein the administration results in a plasma concentration for the β-lactam compound having:
   an area under the curve (AUC) that is higher in the subject in need thereof as compared to a comparable subject being administered to the pharmaceutically effective amount of the β-lactam compound without probenecid over the period of time,
   a maximum plasma concentration ($C_{max}$) that is higher in the subject in need thereof as compared to the comparable subject being administered to the pharmaceutically effective amount of the β-lactam compound without probenecid over the period of time, or
   a combination thereof.

Exemplary Methods
   In some aspects, the present disclosure provides a method of treating or preventing a disease, comprising administering to a subject in need thereof an oral co-formulation of about 500 mg of Compound III-2b and about 500 mg of probenecid,
  wherein the administration results in a plasma concentration for Compound III-2b having:
    an area under the curve (AUC) that is higher in the subject in need thereof as compared to a comparable subject being administered with Compound III-2b and probenecid by different administration routes by about 20% or greater within about 1 day from the administration; and
    a maximum plasma concentration ($C_{max}$) in the subject in need thereof that is substantially the same as compared to a comparable subject being administered with Compound III-2b and probenecid by different administration routes.

In some aspects, the present disclosure provides a method of treating or preventing a disease, comprising administering to a subject in need thereof an oral co-formulation of about 500 mg of Compound III-2b and about 500 mg of probenecid,
  wherein the administration results in a plasma concentration for Compound III-2b having an area under the curve (AUC) being from about 4800 ng·h/mL to about 4850 ng·h/mL within about 12 hours from the administration and a maximum plasma concentration ($C_{max}$) of Compound III-2b being from about 1800 ng/mL to about 1850 ng/mL.

In some aspects, the present disclosure provides a method of treating or preventing a disease, comprising administering to a subject in need thereof an oral co-formulation of about 500 mg of Compound III-2b and about 500 mg of probenecid,
  wherein the administration results in a plasma concentration for Compound III-2b having an area under the curve (AUC) being from about 7550 ng·h/mL to about 8000 ng·h/mL within about 12 hours from the administration and a maximum plasma concentration ($C_{max}$) of Compound III-2b being from about 2650 ng/mL to about 2700 ng/mL.

Pharmaceutical Compositions and Pharmaceutical Kits

In some aspects, the present disclosure provides a pharmaceutical composition comprising a β-lactam compound or a pharmaceutically acceptable salt thereof and probenecid or a pharmaceutically acceptable salt thereof.

In some embodiments, the pharmaceutical composition is in an oral dosage form.

In some embodiments, the pharmaceutical composition comprises:
  from 20 mg to about 5 g, from about 50 mg to about 2 g, from about 80 mg to about 1 g, from about 100 mg to about 900 mg, from about 200 mg to about 800 mg, from about 300 mg to about 700 mg, from about 400 mg to about 600 mg, from about 450 mg to about 550 mg, or from about 480 mg to about 520 mg of the β-lactam compound or the pharmaceutically acceptable salt thereof; and
  from 20 mg to about 5 g, from about 50 mg to about 2 g, from about 80 mg to about 1 g, from about 100 mg to about 900 mg, from about 200 mg to about 800 mg, from about 300 mg to about 700 mg, from about 400 mg to about 600 mg, from about 450 mg to about 550 mg, or from about 480 mg to about 520 mg of probenecid or the pharmaceutically acceptable salt thereof.

In some embodiments, the pharmaceutical composition comprises about 500 mg of the β-lactam compound or the pharmaceutically acceptable salt thereof, and about 500 mg of probenecid or the pharmaceutically acceptable salt thereof.

In some embodiments, the pharmaceutical composition comprises about 500 mg of Compound III-2b and about 500 mg of probenecid.

In some embodiments, the pharmaceutical composition, when being administered to a subject in need thereof, results in one or more of the effects disclosed herein (e.g., the AUC and/or $C_{max}$ for the β-lactam compound disclosed herein).

In some aspects, the present disclosure provides a pharmaceutical kit comprising a β-lactam compound or a pharmaceutically acceptable salt thereof in a first package and probenecid or a pharmaceutically acceptable salt thereof in a second package.

In some embodiments, at least one of the β-lactam compound or the pharmaceutically acceptable salt thereof or the probenecid or the pharmaceutically acceptable salt thereof is in an oral dosage form;
  preferably, the β-lactam compound or the pharmaceutically acceptable salt thereof is in an oral dosage form, or the probenecid or the pharmaceutically acceptable salt thereof is in an oral dosage form;
  more preferably, both of the β-lactam compound or the pharmaceutically acceptable salt thereof and the probenecid or the pharmaceutically acceptable salt thereof are in oral dosage forms.

In some embodiments, the pharmaceutical kit, when being used by a subject in need thereof, results in one or more of the effects disclosed herein (e.g., the AUC and/or Cma for the 0-lactam compound disclosed herein).

In some embodiments, the pharmaceutical kit comprises:
  from 20 mg to about 5 g, from about 50 mg to about 2 g, from about 80 mg to about 1 g, from about 100 mg to about 900 mg, from about 200 mg to about 800 mg, from about 300 mg to about 700 mg, from about 400 mg to about 600 mg, from about 450 mg to about 550 mg, or from about 480 mg to about 520 mg of the β-lactam compound or the pharmaceutically acceptable salt thereof in the first package; and
  from 20 mg to about 5 g, from about 50 mg to about 2 g, from about 80 mg to about 1 g, from about 100 mg to about 900 mg, from about 200 mg to about 800 mg, from about 300 mg to about 700 mg, from about 400 mg to about 600 mg, from about 450 mg to about 550 mg, or from about 480 mg to about 520 mg of probenecid or the pharmaceutically acceptable salt thereof in the second package.

In some embodiments, the pharmaceutical composition comprises about 500 mg of the β-lactam compound or the pharmaceutically acceptable salt thereof in the first package; and about 500 mg of probenecid or the pharmaceutically acceptable salt thereof in the second package.

In some embodiments, the pharmaceutical composition comprises about 500 mg of Compound III-2b in the first package and about 500 mg of probenecid in the second package.

Other Suitable Compounds

In some aspects, the present disclosure provides a compound or a pharmaceutical salt thereof, wherein administration of the compound or the pharmaceutical salt thereof in combination with probenecid or a pharmaceutically acceptable salt thereof into a subject in need thereof by the same administration route results in a plasma concentration versus time curve for the compound having:
  an area under the curve (AUC) that is higher in the subject in need thereof as compared to a comparable subject being administered with the compound and probenecid by different administration routes;

a maximum plasma concentration ($C_{max}$) in the subject in need thereof that is substantially the same as compared to a comparable subject being administered with the compound and probenecid by different administration routes; or a combination thereof.

In some aspects, the present disclosure provides a compound or a pharmaceutical salt thereof, wherein administration of the compound or the pharmaceutical salt thereof in combination with probenecid or a pharmaceutically acceptable salt thereof into a subject in need thereof over a period of time results in a plasma concentration versus time curve for the compound having:

an area under the curve (AUC) that is higher in the subject in need thereof as compared to a comparable subject being administered to the pharmaceutically effective amount of the compound without probenecid over the period of time, a maximum plasma concentration ($C_{max}$) for the compound that is higher in the subject in need thereof as compared to the comparable subject being administered to the pharmaceutically effective amount of the compound without probenecid over the period of time, or a combination thereof.

In some embodiments, the compound is selected from the group consisting of:
Latanopost acid
$PGH_2$
$PGE_1$
$PGE_2$
$PGF_{2n}$
Thromboxane $B_2$
pharmaceutically acceptable salts thereof, prodrugs thereof, analogs thereof, and derivatives thereof.

In some embodiments, the compound is selected from the group consisting of:
Aliskiren
Atorvastatin
Benzylpenicillin
BDE47
BDE99
BDE153
Bosentan
Bromosulphophathalein
CP-671,305
Dehydroepiandrosterone-3-sulphate
Eltrombopag
Estrone-3-sulphate
Ezetimibe glucuronide
Fexofenadine
Fluvastatin
Glibenclamide
Latanoprost acid
M1705S
Mesalazine
Montelukast
Pravastatin
Pitavastatin
Pregnenolone sulphate
$PGE_2$
Rosuvastatin
Talinolol
Taurocholate
Tebipenem pivoxil
Thyroxine (T4)
Unoprostone metabolite
pharmaceutically acceptable salts thereof, prodrugs thereof, analogs thereof, and derivatives thereof.

In some embodiments, the compound is selected from the group consisting of:
Acebutolol
APD-ajmalinium
Atenolol
Atrasentan
Bamet-R2
Bamet-UD2
Bilirubin
BQ-123
Bromosulphophthalein
Celiprolo
Chlorambucil-taurocholate
Cholate
Ciproiloxacin
CRC220
Darunavir
Dehydroeplandrosterone-3-sulphate
Deltorphin II
[D-penicillamine$^{2,3}$]enkephalin
Enoxacin
Epicatechin gallate
Epigallocatechin galate
Erythromycin
Estradiol-170-glucuronide
Estrone-3-sulphate
Fexofenadine
Gatifloxacin
Gd-820790
Glycocholate
Hydroxyurea
Imatinib
Labetalol
Levofloxacin
Lomefloxacin
Lopinavir
Methotrexate
Microcystin
N-methylquinidine
N-methylquinine
Nadolol
Norfloxacin
Ouabain
Pitavastatin
$PGE_2$
Reverse triiodothyronine (rT3)
Rocuronium
Rosuvastatin
Saquinavir
Sotalol
Talinolol
Taurocholate
Taurochenodeoxycholate
Tauroursodeoxycholate
Thyroxine (T4)
Tebipenem pivoxil
TR-14035
Triiodothyronine (T3)
Unoprostone metabolite
pharmaceutically acceptable salts thereof, prodrugs thereof, analogs thereof, and derivatives thereof.

In some embodiments, the compound is a monobactam.

In some embodiments, the compound is aztreonam tigemonam, carumonam, nocardicin A, an analog thereof, or a derivative thereof.

In some embodiments, the compound is a penem, a carbapenem, or a clavam.

In some embodiments, the compound is benzylpenicillin, benzathine benzylpenicillin, procaine benzylpenicillin, phenoxymethylpenicillin, propicillin, pheneticillin, azidocillin, clometocillin, penamecillin, cloxacillin (e.g., dicloxacillin or flucloxacillin), oxacillin, nafcillin, methicillin, amoxicillin, ampicillin (e.g., pivampicillin, hetacillin, bacampicillin, metampicillin, talampicillin), epicillin, ticarcillin, carbenicillin, carindacillin, temocillin, piperacillin, azlocillin, mezlocillin, mecillinam (e.g., pivmecillinam), sulbenicillin, a pharmaceutically acceptable salt thereof, a prodrug thereof, an analog thereof, or a derivative thereof.

In some embodiments, the compound is a penem or a carbapenem.

In some embodiments, the compound is a thiopenem, an oxypenem, an aminopenem, an alkylpenems, or an arylpenem.

In some embodiments, the compound is ertapenem, antipseudomonal (e.g., doripenem, imipenem, meropenem), biapenem, panipenem, sulopenem, a pharmaceutically acceptable salt thereof, a prodrug thereof, an analog thereof, or a derivative thereof.

In some embodiments, the compound is a cephem, a carbacephem, or an oxacephem.

In some embodiments, the compound is cefazolin, cefalexin, cefadroxil, cefapirin, cefazedone, cefazaflur, cefradine, cefroxadine, ceftezole, cefaloglycin, cefacetrile, cefalonium, cefaloridine, cefalotin, cefatrizine, cefaclor, cefotetan, cephamycin (e.g., cefoxitin, cefprozil, cefuroxime, cefuroxime axetil, cefamandole, cefminox, cefonicid, ceforanide, cefotiam, cefbuperazone, cefuzonam, cefmetazole), carbacephem (e.g., loracarbef), cefixime, ceftriaxone, antipseudomonal (e.g, ceftazidime, cefoperazone), cefdinir, cefcapene, cefdaloxime, ceftizoxime, cefmenoxime, cefotaxime, cefpiramide, cefpodoxime, ceftibuten, cefditoren, cefetamet, cefodizime, cefpimizole, cefsulodin, cefteram, ceftiolene, oxacephem (e.g., flomoxef, latamoxef), cefepime, cefozopran, cefpirome, cefquinome, ceftaroline fosamil, ceftolozane, ceftobiprole, ceftiofur, cefquinome, cefovecin, a pharmaceutically acceptable salt thereof, a prodrug thereof, an analog thereof, or a derivative thereof.

In some embodiments, the compound is a thiopenem.

In some embodiments, the compound is of Formula (I):

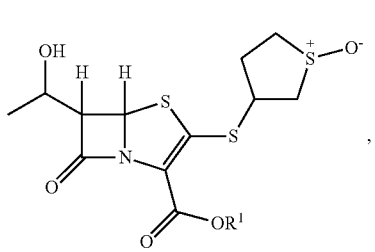

(I)

a pharmaceutically acceptable salt thereof, a prodrug thereof, an analog thereof, or a derivative thereof, wherein $R^1$ is H or optionally substituted alkyl.

In some embodiments, the compound is of Formula (Ia):

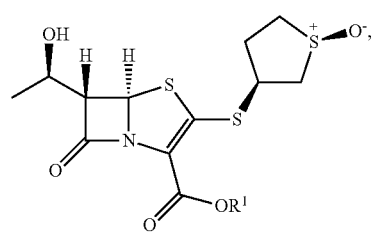

(Ia)

a pharmaceutically acceptable salt thereof, a prodrug thereof, an analog thereof, or a derivative thereof.

In some embodiments, the compound is of Formula (Ib):

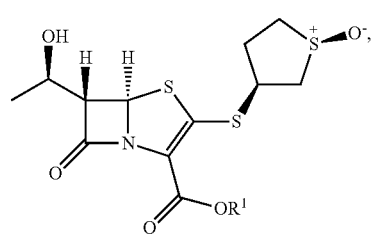

(Ib)

a pharmaceutically acceptable salt thereof, a prodrug thereof, an analog thereof, or a derivative thereof.

In some embodiments, $R^1$ is H.

In some embodiments, the compound is of Formula (II):

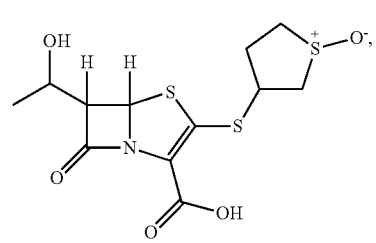

(II)

a pharmaceutically acceptable salt thereof, a prodrug thereof, an analog thereof, or a derivative thereof.

In some embodiments, the compound is of Formula (IIa):

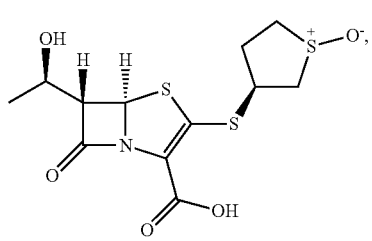

(IIa)

a pharmaceutically acceptable salt thereof, a prodrug thereof, an analog thereof, or a derivative thereof.

In some embodiments, the compound is of Formula (IIb):

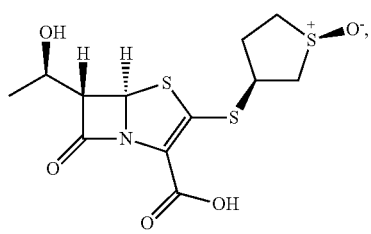
(IIb)

a pharmaceutically acceptable salt thereof, a prodrug thereof, an analog thereof, or a derivative thereof.

In some embodiments, R¹ is optionally substituted alkyl.

In some embodiments, the compound is of any one of Formulae (III), (IIIa), and (IIIb):

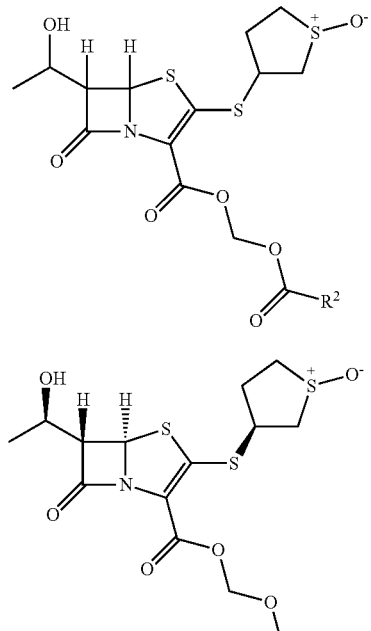
(III)

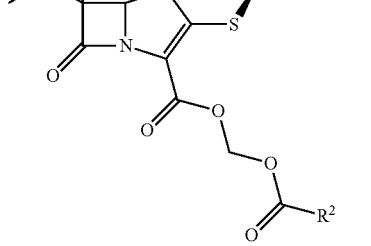
(IIIa)

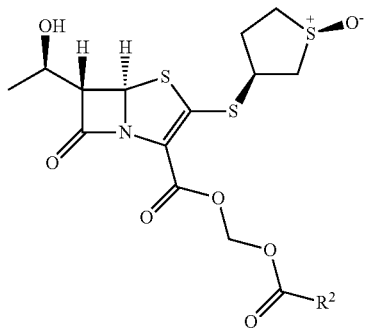
(IIIb)

a pharmaceutically acceptable salt thereof, a prodrug thereof, an analog thereof, or a derivative thereof, wherein R² is H or optionally substituted alkyl.

In some embodiments, the compound is selected from the group consisting of:

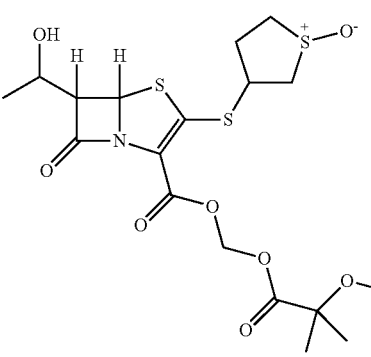
(Compound III-1)

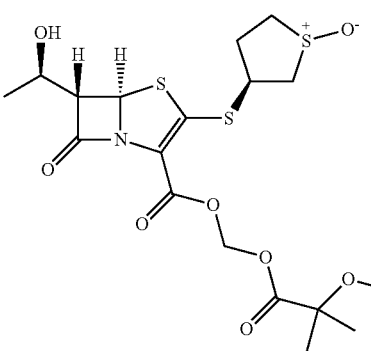
(Compound III-1a)

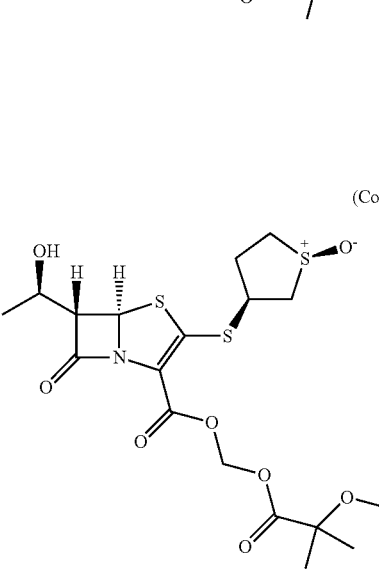
(Compound III-1b)

pharmaceutically acceptable salts thereof, prodrugs thereof, analogs thereof, and derivatives thereof.

In some embodiments, the compound is selected from the group consisting of:

(Compound III-2)

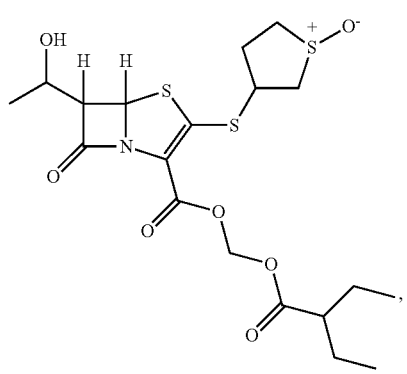

(Compound III-2a)

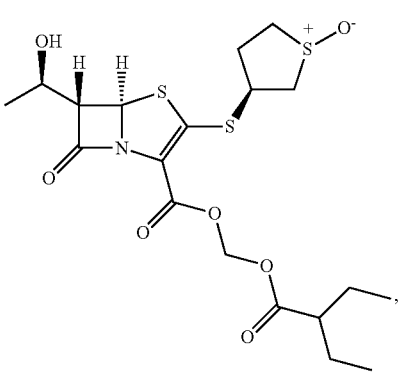

(Compound III-2b)

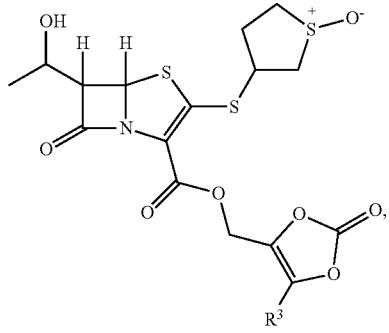

pharmaceutically acceptable salts thereof, prodrugs thereof, analogs thereof, and derivatives thereof.

In some embodiments, the compound is of any one of Formulae (IV), (IVa), and (IVb):

(IV)

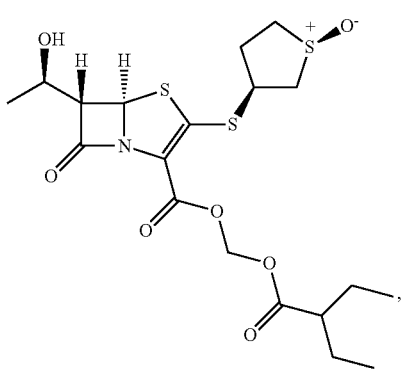

(IVa)

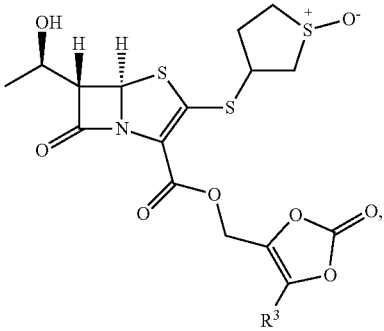

(IVb)

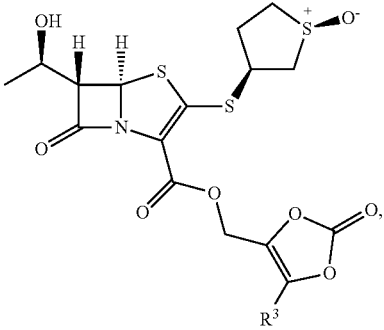

a pharmaceutically acceptable salt thereof, a prodrug thereof, an analog thereof, or a derivative thereof, wherein $R^3$ is H or optionally substituted alkyl.

In some embodiments, $R^3$ is $C_2$-$C_8$ alkyl.

In some embodiments, $R^3$ is $CH_2CH_3$, $CH_2CH_2CH_3$, or $CH_2CH(CH_3)_2$.

Definitions

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl. In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "cycloalkyl" refers to a saturated or unsaturated nonaromatic hydrocarbon mono- or multi-ring (e.g., fused, bridged, or spiro rings) system having 3 to 30 carbon atoms (e.g., $C_3$-$C_{12}$, $C_3$-$C_{10}$, or $C_3$-$C_8$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, 1,2,3,4-tetrahydronaphthalenyl, and adamantyl.

As used herein, the term "heterocycloalkyl" refers to a saturated or unsaturated nonaromatic 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, P, or Se), e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur, unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, 3-azabicyclo[3.1.0]hexanyl, 3-azabicyclo[3.1.0]hexan-3-yl, 1,4,5,6-tetrahydropyrrolo[3,4-c]pyrazolyl, 3,4,5,6,7,8-hexahydropyrido[4,3-d]pyrimidinyl, 4,5,6,7-tetrahydro-1H-pyrazolo[3,4-c]pyridinyl, 5,6,7,8-tetrahydropyrido[4,3-d]pyrimidinyl, 2-azaspiro[3.3]heptanyl, 2-methyl-2-azaspiro[3.3]heptanyl, 2-azaspiro[3.5]nonanyl, 2-methyl-2-azaspiro[3.5]nonanyl, 2-azaspiro[4.5]decanyl, 2-methyl-2-azaspiro[4.5]decanyl, 2-oxa-azaspiro[3.4]octanyl, 2-oxa-azaspiro[3.4]octan-6-yl, and the like. In the case of multicyclic non-aromatic rings, only one of the rings needs to be non-aromatic (e.g., 1,2,3,4-tetrahydronaphthalenyl or 2,3-dihydroindole).

As used herein, the term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, the term "alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

As used herein, the term "alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms. As used herein, "$C_2$-$C_6$ alkenylene linker" or "$C_2$-$C_6$ alkynylene linker" is intended to include $C_2$, $C_3$, $C_4$, $C_5$ or $C_6$ chain (linear or branched) divalent unsaturated aliphatic hydrocarbon groups. For example, $C_2$-$C_6$ alkenylene linker is intended to include $C_2$, $C_3$, $C_4$, $C_5$ and $C_6$ alkenylene linker groups.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

As used herein, the term "aryl" includes groups with aromaticity, including "conjugated," or multicyclic systems with one or more aromatic rings and do not contain any heteroatom in the ring structure. Examples include phenyl, naphthalenyl, etc.

As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1. Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, quinoline, isoquinoline, naphthrydine, indole, benzofuran, purine, benzofuran, deazapurine, indolizine.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl such as benzo[d][1,3]dioxole-5-yl).

As used herein, the term "carbocycle" or "carbocyclic ring" is intended to include any stable monocyclic, bicyclic or tricyclic ring having the specified number of carbons, any of which may be saturated, unsaturated, or aromatic. Carbocycle includes cycloalkyl and aryl. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, and [4.4.0] bicyclodecane and [2.2.2] bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, the term "heterocycle" or "heterocyclic group" includes any ring structure (saturated, unsaturated, or aromatic) which contains at least one ring heteroatom (e.g., 1-4 heteroatoms selected from N, O and S). Heterocycle includes heterocycloalkyl and heteroaryl.

Examples of heterocycles include, but are not limited to, morpholine, pyrrolidine, tetrahydrothiophene, piperidine, piperazine, oxetane, pyran, tetrahydropyran, azetidine, and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl (e.g., benzo[d][1,3]dioxole-5-yl), morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

As used herein, the term "substituted," means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., R) occurs more than one time in any constituent or formula for a compound, its definition at each occurrence is independent of its definition at every other occurrence. Thus, for example, if a group is shown to be substituted with 0-2 R moieties, then the group may optionally be substituted with up to two R moieties and R at each occurrence is selected independently from the definition of R. Also, combinations of substituents and/or variables are permissible, but only if such combinations result in stable compounds.

As used herein, the term "hydroxy" or "hydroxyl" includes groups with an —OH or —O⁻.

As used herein, the term "halo" or "halogen" refers to fluoro, chloro, bromo and iodo. The term "perhalogenated" generally refers to a moiety wherein all hydrogen atoms are replaced by halogen atoms. The term "haloalkyl" or "haloalkoxyl" refers to an alkyl or alkoxyl substituted with one or more halogen atoms.

As used herein, the term "carbonyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

As used herein, the term "carboxyl" refers to —COOH or its $C_1$-$C_6$ alkyl ester.

As used herein, the term "acyl" includes moieties that contain the acyl radical (R—C(O)—) or a carbonyl group. As used herein, the term "substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, the term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

As used herein, the term "ether" or "alkoxy" includes compounds or moieties which contain an oxygen bonded to two carbon atoms or heteroatoms. For example, the term includes "alkoxyalkyl," which refers to an alkyl, alkenyl, or alkynyl group covalently bonded to an oxygen atom which is covalently bonded to an alkyl group.

As used herein, the term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

As used herein, the term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

As used herein, the term "thiocarbonyl" or "thiocarboxy" includes compounds and moieties which contain a carbon connected with a double bond to a sulfur atom.

As used herein, the term "thioether" includes moieties which contain a sulfur atom bonded to two carbon atoms or heteroatoms. Examples of thioethers include, but are not limited to alkthioalkyls, alkthioalkenyls, and alkthioalkynyls. The term "alkthioalkyls" include moieties with an alkyl, alkenyl, or alkynyl group bonded to a sulfur atom which is bonded to an alkyl group. Similarly, the term "alkthioalkenyls" refers to moieties wherein an alkyl, alkenyl or alkynyl group is bonded to a sulfur atom which is covalently bonded to an alkenyl group; and alkthioalkynyls" refers to moieties wherein an alkyl, alkenyl or alkynyl group is bonded to a sulfur atom which is covalently bonded to an alkynyl group.

As used herein, the term "amine" or "amino" refers to —NH$_2$. "Alkylamino" includes groups of compounds wherein the nitrogen of —NH$_2$ is bound to at least one alkyl group.

Examples of alkylamino groups include benzylamino, methylamino, ethylamino, phenethylamino, etc.

As used herein, the term "dialkylamino" includes groups wherein the nitrogen of —NH$_2$ is bound to two alkyl groups. Examples of dialkylamino groups include, but are not limited to, dimethylamino and diethylamino.

As used herein, the terms "arylamino" and "diarylamino" include groups wherein the nitrogen is bound to at least one or two aryl groups, respectively.

As used herein, the terms "aminoaryl" and "aminoaryloxy" refer to aryl and aryloxy substituted with amino.

As used herein, the terms "alkylarylamino," "alkylaminoaryl" or "arylaminoalkyl" refers to an amino group which is bound to at least one alkyl group and at least one aryl group.

As used herein, the terms "alkaminoalkyl" refers to an alkyl, alkenyl, or alkynyl group bound to a nitrogen atom which is also bound to an alkyl group.

As used herein, the terms "acylamino" includes groups wherein nitrogen is bound to an acyl group. Examples of acylamino include, but are not limited to, alkylcarbonylamino, arylcarbonylamino, carbamoyl and ureido groups.

As used herein, the term"amide" or "aminocarboxy" includes compounds or moieties that contain a nitrogen atom that is bound to the carbon of a carbonyl or a thiocarbonyl group.

As used herein, the term "alkaminocarboxy" includes alkyl, alkenyl or alkynyl groups bound to an amino group which is bound to the carbon of a carbonyl or thiocarbonyl group.

As used herein, the term"arylaminocarboxy" includes aryl or heteroaryl moieties bound to an amino group that is bound to the carbon of a carbonyl or thiocarbonyl group.

As used herein, the terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group.

Amides can be substituted with substituents such as straight chain alkyl, branched alkyl, cycloalkyl, aryl, heteroaryl or heterocycle. Substituents on amide groups may be further substituted.

It is understood that probenecid (e.g., sold under the brandname Probalan) is of the following structure:

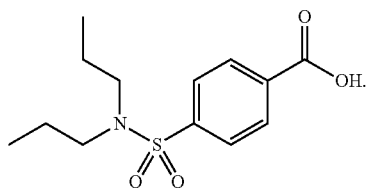 [SMILES: CCCN(CCC)S(=O)(=O)c1ccc(C(=O)O)cc1]

Compounds of the present disclosure that contain nitrogens can be converted to N-oxides by treatment with an oxidizing agent (e.g., 3-chloroperoxybenzoic acid (mCPBA) and/or hydrogen peroxides) to afford other compounds of the present disclosure. Thus, all shown and claimed nitrogen-containing compounds are considered, when allowed by valency and structure, to include both the compound as shown and its N-oxide derivative (which can be designated as N→O or N$^+$—O$^-$). Furthermore, in other instances, the nitrogens in the compounds of the present disclosure can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

In the present specification, the structural formula of the compound represents a certain isomer for convenience in some cases, but the present disclosure includes all isomers, such as geometrical isomers, optical isomers based on an asymmetrical carbon, stereoisomers, tautomers, and the like, it being understood that not all isomers may have the same level of activity. In addition, a crystal polymorphism may be present for the compounds represented by the formula. It is noted that any crystal form, crystal form mixture, or anhydride or hydrate thereof is included in the scope of the present disclosure.

As used herein, the term "isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

As used herein, the term "chiral center" refers to a carbon atom bonded to four nonidentical substituents.

As used herein, the term "chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

As used herein, the term "geometric isomer" means the diastereomers that owe their existence to hindered rotation about double bonds or a cycloalkyl linker (e.g., 1,3-cylcobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present disclosure may be depicted as different chiral isomers or geometric isomers. It is also to be understood that when compounds have chiral isomeric or geometric isomeric forms, all isomeric forms are intended to be included in the scope of the present disclosure, and the naming of the compounds does not exclude any isomeric forms, it being understood that not all isomers may have the same level of activity.

It is to be understood that the structures and other compounds discussed in this disclosure include all atropic isomers thereof. It is also to be understood that not all atropic isomers may have the same level of activity.

As used herein, the term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

As used herein, the term "tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertible by tautomerizations is called tautomerism. Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

It is to be understood that the compounds of the present disclosure may be depicted as different tautomers. It should also be understood that when compounds have tautomeric forms, all tautomeric forms are intended to be included in the scope of the present disclosure, and the naming of the compounds does not exclude any tautomer form. It will be understood that certain tautomers may have a higher level of activity than others.

As used herein, the term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

It is to be understood that the compounds of any Formula described herein include the compounds themselves, as well as their salts, and their solvates, if applicable. A salt, for example, can be formed between an anion and a positively charged group (e.g., amino) on a substituted benzene compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate).

As used herein, the term "pharmaceutically acceptable anion" refers to an anion suitable for forming a pharmaceutically acceptable salt. Likewise, a salt can also be formed between a cation and a negatively charged group (e.g., carboxylate) on a substituted benzene compound. Suitable cations include sodium ion, potassium ion, magnesium ion, calcium ion, and an ammonium cation such as tetramethylammonium ion. The substituted benzene compounds also include those salts containing quaternary nitrogen atoms.

It is to be understood that the compounds of the present disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

As used herein, the term "solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As used herein, the term "derivative" refers to compounds that have a common core structure, and are substituted with various groups as described herein.

As used herein, the term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides, tetrazoles, sulfonates and phosphonates. See, e.g., Patani and LaVoie, Chem. Rev. 96, 3147-3176, 1996.

It is to be understood that the present disclosure is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

As used herein, the expressions "one or more of A, B, or C," "one or more A, B, or C," "one or more of A, B, and C," "one or more A, B, and C," "selected from the group consisting of A, B, and C", "selected from A, B, and C", and the like are used interchangeably and all refer to a selection from a group consisting of A, B, and/or C, i.e., one or more As, one or more Bs, one or more Cs, or any combination thereof, unless indicated otherwise.

It is to be understood that the present disclosure provides methods for the synthesis of the compounds of any of the Formulae described herein. The present disclosure also provides detailed methods for the synthesis of various disclosed compounds of the present disclosure according to the following schemes as well as those shown in the Examples.

It is to be understood that, throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

It is to be understood that the synthetic processes of the disclosure can tolerate a wide variety of functional groups, therefore various substituted starting materials can be used. The processes generally provide the desired final compound at or near the end of the overall process, although it may be desirable in certain instances to further convert the compound to a pharmaceutically acceptable salt thereof.

It is to be understood that compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, 5$^{th}$ edition, John Wiley & Sons: New York, 2001; Greene, T. W., Wuts, P. G. M., *Protective Groups in Organic Synthesis*, 3$^{rd}$ edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognized reference textbooks of organic synthesis known to those in the art One of ordinary skill in the art will note that, during the reaction sequences and synthetic schemes described herein, the order of certain steps may be changed, such as the introduction and removal of protecting groups. One of ordinary skill in the art will recognize that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis*, 3$^{rd}$ edition, John Wiley & Sons: New York, 1999.

It is to be understood that, unless otherwise stated, any description of a method of treatment includes use of the compounds to provide such treatment or prophylaxis as is described herein, as well as use of the compounds to prepare a medicament to treat or prevent such condition. The treatment includes treatment of human or non-human animals including rodents and other disease models.

As used herein, the term "subject" is interchangeable with the term "subject in need thereof", both of which refer to a subject having a disease or having an increased risk of developing the disease. A "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human.

As used herein, the term "comparable subject" refers to a subject with comparable parameters, or in comparable conditions, as of the subject being compared (e.g., the subject being treated). For example, the "comparable subject" may have a disease as of the subject being compared, or have an increased risk of developing the disease as of the subject being compared. For another example, the "comparable subject" may exhibit one or more plasma pharmakinetic parameters (e.g., $C_{max}$ or AUC) to one or more pharmaceutical agents (e.g., a β-lactam compound, probenecid, or a combination thereof) as of the subject being compared. In some embodiments, the "comparable subject" may be the subject being compared at a different time, e.g., the subject being treated (e.g., by administrating a β-lactam compound and probenecid) may be subjected to conditions (e.g., administration of a β-lactam compound without probenecid) as a "comparable subject" prior to the treatment.

As used herein, the term "candidate compound" refers to a compound of the present disclosure, or a pharmaceutically acceptable salt, polymorph or solvate thereof, that has been or will be tested in one or more in vitro or in vivo biological assays, in order to determine if that compound is likely to elicit a desired biological or medical response in a cell, tissue, system, animal or human that is being sought by a researcher or clinician. A candidate compound is a compound of the present disclosure, or a pharmaceutically acceptable salt, polymorph or solvate thereof. The biological response or effect can occur in vitro or in an animal model, as well as other biological changes that are observable in vitro. In vitro or in vivo biological assays can include, but are not limited to, enzymatic activity assays, electrophoretic mobility shift assays, reporter gene assays, in vitro cell viability assays, and the assays described herein.

As used herein, the term "treating" or "treat" describes the management and care of a patient for the purpose of combating a disease, condition, or disorder and includes the administration of a compound of the present disclosure, or a pharmaceutically acceptable salt, polymorph or solvate thereof, to alleviate the symptoms or complications of a disease, condition or disorder, or to eliminate the disease, condition or disorder. The term "treat" can also include treatment of a cell in vitro or an animal model.

As used herein, the term "temporal proximity" refers to that administration of one therapeutic agent (e.g., a β-lactam compound disclosed herein) occurs within a time period before or after the administration of another therapeutic agent (e.g., probenecid), such that the therapeutic effect of the one therapeutic agent overlaps with the therapeutic effect of the other therapeutic agent. In some embodiments, the therapeutic effect of the one therapeutic agent completely overlaps with the therapeutic effect of the other therapeutic agent. In some embodiments, "temporal proximity" means that administration of one therapeutic agent occurs within a time period before or after the administration of another therapeutic agent, such that there is a synergistic effect between the one therapeutic agent and the other therapeutic agent. "Temporal proximity" may vary according to various factors, including but not limited to, the age, gender, weight, genetic background, medical condition, disease history, and treatment history of the subject to which the therapeutic agents are to be administered; the disease or condition to be treated or ameliorated; the therapeutic outcome to be achieved; the dosage, dosing frequency, and dosing duration of the therapeutic agents; the pharmacokinetics and pharmacodynamics of the therapeutic agents; and the route(s) through which the therapeutic agents are administered. In some embodiments, "temporal proximity" means within 15 minutes, within 30 minutes, within an hour, within two hours, within four hours, within six hours, within eight hours, within 12 hours, within 18 hours, within 24 hours, within 36 hours, within 2 days, within 3 days, within 4 days, within 5 days, within 6 days, within a week, within 2 weeks, within 3 weeks, within 4 weeks, with 6 weeks, or within 8 weeks. In some embodiments, multiple administration of one therapeutic agent can occur in temporal proximity to a single administration of another therapeutic agent. In some embodiments, temporal proximity may change during a treatment cycle or within a dosing regimen.

It is to be understood that a compound of the present disclosure, or a pharmaceutically acceptable salt, polymorph or solvate thereof, can or may also be used to prevent a relevant disease, condition or disorder, or used to identify suitable candidates for such purposes.

As used herein, the term "preventing," "prevent," or "protecting against" describes reducing or eliminating the onset of the symptoms or complications of such disease, condition or disorder.

It is to be understood that one skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, PA, $18^{th}$ edition (1990), Mandell, et al., *Principles and Practice of Infectious Diseases*, Saunders Publishing (8th edition, 2014). These texts can, of course, also be referred to in making or using an aspect of the disclosure.

As used herein, the term "combination therapy" or "co-therapy" includes the administration of a compound of the present disclosure, or a pharmaceutically acceptable salt, polymorph or solvate thereof, and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents.

It is to be understood that the present disclosure also provides pharmaceutical compositions comprising any compound described herein in combination with at least one pharmaceutically acceptable excipient or carrier.

As used herein, the term "pharmaceutical composition" is a formulation containing the compounds of the present disclosure in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the term "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

It is to be understood that a pharmaceutical composition of the disclosure is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

It is to be understood that a compound or pharmaceutical composition of the disclosure can be administered to a subject in many of the well-known methods currently used for chemotherapeutic treatment. For example, a compound of the disclosure may be injected into the blood stream or body cavities or taken orally or applied through the skin with patches. The dose chosen should be sufficient to constitute effective treatment but not so high as to cause unacceptable side effects. The state of the disease condition and the health of the patient should preferably be closely monitored during and for a reasonable period after treatment.

As used herein, the term "therapeutically effective amount", refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

It is to be understood that, for any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present disclosure may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives.

Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved.

In therapeutic applications, the dosages of the pharmaceutical compositions used in accordance with the disclosure vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the symptoms of the disease and also preferably causing complete regression of the disease. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. Improvement in survival and growth indicates regression. As used herein, the term "dosage effective manner" refers to amount of an active compound to produce the desired biological effect in a subject or cell.

It is to be understood that the pharmaceutical compositions can be included in a container, pack, or dispenser together with instructions for administration.

It is to be understood that, for the compounds of the present disclosure being capable of further forming salts, all of these forms are also contemplated within the scope of the claimed disclosure.

As used herein, the term "pharmaceutically acceptable salts" refer to derivatives of the compounds of the present disclosure wherein the parent compound is modified by making acid or base salts thereof. In some embodiments, the pharmaceutically acceptable salt of a compound (e.g., a β-lactam compound or probenecid described herein) is also a prodrug of the compound. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ration other than 1:1, e.g., 3:1, 2:1, 1:2, or 1:3.

It is to be understood that all references to pharmaceutically acceptable salts include solvent addition forms (solvates) or crystal forms (polymorphs) as defined herein, of the same salt.

As used herein, the term "prodrug" refers to any agent which, when administered to a mammal, is converted in whole or in part to a targeted compound (e.g., a β-lactam compound or probenecid described herein). In some embodiments, the prodrug of a compound (e.g., a β-lactam compound or probenecid described herein) is also a pharmaceutically acceptable salt of the compound.

It is to be understood that the compounds of the present disclosure can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., acetate, propionate or other ester.

The compounds, or pharmaceutically acceptable salts thereof, are administered orally, nasally, transdermally, pulmonary, inhalationally, buccally, sublingually, intraperitoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the disclosure can be found in *Remington: the Science and Practice of Pharmacy,* 19$^{th}$ edition, Mack Publishing Co., Easton, PA (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

In the synthetic schemes described herein, compounds may be drawn with one particular configuration for simplicity. Such particular configurations are not to be construed as limiting the disclosure to one or another isomer, tautomer, regioisomer or stereoisomer, nor does it exclude mixtures of isomers, tautomers, regioisomers or stereoisomers; however, it will be understood that a given isomer, tautomer, regioisomer or stereoisomer may have a higher level of activity than another isomer, tautomer, regioisomer or stereoisomer.

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Example 1: Assessment of Probenecid's Effects on Plasma Pharmacokinetic Parameters for β-Lactam Compounds The effects of probenecid on the pharmacokinetics of sulopneme and its prodrugs, Compound III-2b and Compound III-1b, were studied in a randomized, double blinded (Investigator and subject blinded, Sponsor-open), placebo-controlled, multiple dose study, with or without co administration of probenecid, in fed or fasted state. One hundred ninety two subjects were to be randomized to treatment groups to receive either active drug or placebo in fed or fasted state with or without co-administration of 500 mg probenecid.

Subjects were to be dosed twice a day (every 12 hours) for 6 days and on Day 7 they were to be dosed once. All treatment groups could be run in parallel or sequentially. Subjects were allocated based on the randomization list. Randomization numbers were assigned sequentially as subjects entered into groups on the basis of their order of entry into the study. Subjects who withdrew for reasons unrelated to safety may have been replaced. Blood samples were obtained at prespecified intervals in order to characterize pharmacokinetics. Results of the study are provided in Tables 1-3.

TABLE 1

Plasma pharmacokinetic parameters - fasted condition (pharmacokinetic population).

| Parameter (units) | Compound III-1b | Compound III-2b | Compound III-1b + 500 mg Probenecid | Compound III-2b + 500 mg Probenecid |
|---|---|---|---|---|
| Number of Subjects | 8 | 8 | 8 | 8 |
| Day 1 | | | | |
| $C_{max}$ (ng/mL) | 1998.4 (22.91) | 1699.1 (31.64) | 2149.4 (27.39) | 1720.1 (27.11) |
| $T_{max}$ (h) | 1.0000 (0.5000-1.017) | 1.0000 (0.4830-2.017) | 0.98300 (0.5000-1.017) | 0.99150 (0.5000-2.017) |
| $AUC_{tau}$ (hr*ng/mL) | 2843.7 (22.94) | 3623.8 (19.19) | 4186.1 (23.70) | 3857.2 (24.57) |
| $TAMIC_{1.0}$ (h) | 1.0881 (22.94) | 1.0758 (94.61) | 1.528 (22.32) | 1.1880 (68.73) |
| $TAMIC_{0.5}$ (h) | 1.8883 (12.18) | 2.6348 (14.85) | 2.6550 (18.08) | 2.9932 (23.46) |
| Day 7 | | | | |
| $C_{max}$ (ng/mL) | 1247.2 (15.62) | 1289.4 (39.17) | 2123 (21.91) | 1479.5 (30.81) |
| $T_{max}$ (h) | 1.0000 (0.4830-1.017) | 0.99150 (0.5000-1.033) | 0.99150 (0.5000-1.017) | 1.2500 (0.5000-2.967) |
| $AUC_{last}$ (hr*ng/mL) | 1866.7 (25.01) | 2607.4 (19.10) | 4363.8 (29.02) | 4236.5 (26.91) |
| $AUC_{inf}$ (hr*ng/mL) | 1890.3 (24.38) | 2627.8 (18.89) | 4412.5 (28.98) | 4282.7 (27.06) |
| $AUC_{tau}$ (hr*ng/mL) | 1889.9 (24.38) | 2626.3 (18.89) | 4402.5 (28.77) | 4276.4 (26.99) |
| $t_{1/2}$ (h)[1] | 0.78443 (25.88) | 0.93761 (15.34) | 1.2208 (18.14) | 1.0747 (16.36) |
| $TAMIC_{1.0}$ (h) | 0.54586 (65.52) | 0.73202 (62.70) | 1.6161 (28.85) | 1.3240 (84.30) |
| $TAMIC_{0.5}$ (h) | 1.4528 (17.74) | 2.1088 (16.74) | 2.8875 (21.76) | 3.4394 (23.07) |

[1] Displayed for Day 7 only.
$T_{max}$ reported as Median (minimum-maximum).
$AUC_{inf}$ = the area under the concentration time curve extrapolated to infinity;
$AUC_{last}$ = AUC from time 0 to the time of the last (Day 1) quantifiable concentration;
$AUC_{tau}$ = area under the concentration time curve from time 0 to 12 hours;
% CV = coefficient of variation;
$C_{max}$ = maximum observed concentration;
SD = standard deviation;
$t_{1/2}$ = terminal half-life;
$T_{max}$ = time to maximum observed concentration

TABLE 2

Plasma pharmacokinetic parameters - fed condition (pharmacokinetic population).

| Parameter (units) | Compound III-1b | Compound III-2b | Compound III-1b + 500 mg Probenecid | Compound III-2b + 500 mg Probenecid |
|---|---|---|---|---|
| Number of Subjects | 8 | 8 | 8 | 8 |
| Day 1 | | | | |
| $C_{max}$ (ng/mL) | 1434.5 (23.98) | 1730.9 (46.66) | 1567.9 (30.31) | 1615.5 (31.86) |
| $T_{max}$ (h) | 0.9830 (1.0000-1.500) | 1.000 (1.5000-2.983) | 0.9830 (1.0170-5.950) | 0.5000 (1.7415-4.000) |
| $AUC_{tau}$ (hr*ng/mL) | 3274.6 (23.02) | 4413.7 (27.00) | 4128.2 (18.58) | 6255.2 (23.16) |
| $TAMIC_{1.0}$ (h) | 1.180 (43.27) | 2.0882 (25.12) | 1.6543 (32.68) | 2.0925 (46.59) |
| $TAMIC_{0.5}$ (h) | 2.5810 (16.07) | 3.0103 (31.13) | 3.1035 (16.11) | 5.0404 (37.07) |
| Day 7 | | | | |
| $C_{max}$ (ng/mL) | 1204.9 (31.04) | 1179.4 (25.94) | 1791.3 (23.50) | 1586.5 (23.42) |
| $T_{max}$ (h) | 0.9830 (1.0165-2.000) | 1.483 (2.0000-4.000) | 1.000 (1.2420-2.000) | 1.000 (2.5000-4.017) |
| $AUC_{last}$ (hr*ng/mL) | 2776.6 (23.17) | 3537 (25.01) | 4452.7 (23.32) | 6591.3 (26.35) |
| $AUC_{inf}$ (hr*ng/mL) | 2804.9 (22.94) | 3712.7 (24.27) | 4521.8 (23.42) | 6679.8 (26.42) |
| $AUC_{tau}$ (hr*ng/mL) | 2803.6 (22.95) | 3706.4 (24.21) | 4512.9 (23.41) | 6631.2 (25.87) |

TABLE 2-continued

Plasma pharmacokinetic parameters - fed condition (pharmacokinetic population).

| Parameter (units) | Compound III-1b | Compound III-2b | Compound III-1b + 500 mg Probenecid | Compound III-2b + 500 mg Probenecid |
|---|---|---|---|---|
| | Number of Subjects | | | |
| | 8 | 8 | 8 | 8 |
| $t_{1/2}$ (h)[1] | 0.92384 (11.91) | 0.91139 (26.68) | 1.1311 (12.87) | 1.2174 (30.84) |
| $TAMIC_{1.0}$ (h) | 0.46944 (290.26) | 1.3191 (62.54) | 1.8174 (28.00) | 2.7087 (42.70) |
| $TAMIC_{0.5}$ (h) | 2.2883 (19.01) | 2.8507 (31.48) | 3.1532 (14.59) | 5.1164 (26.75) |

[1]Displayed for Day 7 only.
$T_{max}$ is reported as Median (minimum-maximum).
$AUC_{inf}$ = the area under the concentration time curve extrapolated to infinity;
$AUC_{last}$ = AUC from time 0 to the time of the last (Day 1) quantifiable concentration;
$AUC_{tau}$ = area under the concentration time curve from time 0 to 12 hours;
% CV = coefficient of variation;
$C_{max}$ = maximum observed concentration;
SD = standard deviation;
$t_{1/2}$ = terminal half-life;
$T_{max}$ = time to maximum observed concentration

TABLE 3

Statistical assessment of probenecid effect on plasma pharmacokinetic parameters (pharmacokinetic population).

| Visit | Parameter | Without Probenecid | | | With Probenecid | | | With Probenecid/ Without Probenecid | |
|---|---|---|---|---|---|---|---|---|---|
| | | N[1] | GM | 95% CI | N[1] | GM | 95% CI | GMR | 90% CI |
| Compound III-1b | | | | | | | | | |
| Day 1 | $C_{max}$ (ng/mL) | 16 | 1693.11 | (1452.31, 1973.83) | 16 | 1835.76 | (1574.68, 2140.14) | 1.08 | (0.91, 1.30) |
| | $AUC_{tau}$ (h · ng/mL) | 16 | 3051.54 | (2728.68, 3412.61) | 15 | 4158.98 | (3705.34, 4668.16) | 1.36 | (1.19, 1.56) |
| Day 7 | $C_{max}$ (ng/mL) | 16 | 1225.85 | (1088.01, 1381.14) | 16 | 1950.08 | (1730.81, 2197.12) | 1.59 | (1.38, 1.83) |
| | $AUC_{tau}$ (h · ng/mL) | 16 | 2301.85 | (1997.29, 2652.85) | 16 | 4457.34 | (3867.58, 5137.03) | 1.94 | (1.64, 2.29) |
| Compound III-2b | | | | | | | | | |
| Day 1 | $C_{max}$ (ng/mL) | 16 | 1714.92 | (1450.13, 2028.06) | 16 | 1667.01 | (1409.62, 1971.40) | 0.97 | (0.80, 1.18) |
| | $AUC_{tau}$ (hr * ng/mL) | 16 | 3999.26 | (3439.92, 4649.54) | 16 | 4911.98 | (4224.99, 5710.68) | 1.23 | (1.03, 1.47) |
| Day 7 | $C_{max}$ (ng/mL) | 16 | 1233.18 | (1063.71, 1429.64) | 16 | 1532.10 | (1321.56, 1776.18) | 1.24 | (1.04, 1.48) |
| | $AUC_{tau}$ (hr * ng/mL) | 15 | 3084.36 | (2621.79, 3628.54) | 16 | 5325.20 | (4549.98, 6232.50) | 1.73 | (1.43, 2.08) |

[1]Shows the number of subjects exposed to each treatment that was used in the linear model.
$AUC_{tau}$ = area under the concentration time curve from time 0 to 12 hours;
CI = confidence intervals;
$C_{max}$ = maximum observed concentration;
GM = geometric means;
GM = ratio of geometric means A Phase 1, randomized, investigator-blind, subject-blind, sponsor-open, placebo-controlled, single and multiple dose study of Compound II-2b was further conducted. There were 6 planned cohorts of subjects. Each cohort was planned to enroll 12 subjects, for a total of 72 planned subjects. Subjects in the multidose cohort were dosed for 10 days; new subjects were recruited for each cohort. Results from cohorts 2 and 3, provided in Table 4 are provided below. Subjects in these cohorts, on Days 1 through 9, were dosed BTD (12 hours apart) at approximately 0800 and 2000 hours. On Day 10, subjects were to be dosed only once at approximately 0800 hours. Blood samples were obtained at prespecified intervals in order to characterize pharmacokinetics.

TABLE 4

Plasma pharmacokinetic parameters following administration of Compound III-2b with and without probenecid.

| Parameter[a] | Compound III-2b 1200 mg/Probenecid 1000 mg BID | Compound III-2b 2000 mg BID |
|---|---|---|
| Study Day 1; Plasma | | |
| N, n | 9, 8 | 9, 9 |
| $AUC_{inf}$ (ng · hr/mL) | 20400 (24) | 18100 (26) |
| $AUC_{tau}$ (ng · hr/mL) | 20000 (21) | 17500 (24) |
| $C_{max}$ (ng/mL) | 6520 (25) | 6090 (19) |
| $T_{max}$ (hr) | 1.00 (1.00-3.00) | 1.00 (1.00-2.00) |

TABLE 4-continued

Plasma pharmacokinetic parameters following administration of Compound III-2b with and without probenecid.

| Parameter[a] | Compound III-2b 1200 mg/Probenecid 1000 mg BID | Compound III-2b 2000 mg BID |
|---|---|---|
| $T_{last}$ (hr) | 8.00 (6.00-12.00) | 8.00 (8.00-12.00) |
| $t_{1/2}$ (hr) | 2.09 (63) | 1.66 (50) |
| TAMIC1 | 7.01 (30) | 6.93 (34) |
| TAMIC2 | 5.48 (32) | 5.57 (28) |
| Study Day 10; Plasma | | |
| N, n | 9, 6 | 9, 8 |
| $AUC_{inf}$ (ng · hr/mL) | NC | NC |
| $AUC_{tau}$ (ng · hr/mL) | 18800 (18) | 12200 (21) |
| $C_{max}$ (ng/mL) | 6660 (23) | 5480 (18) |
| $T_{max}$ (hr) | 1.30 (1.00-2.00) | 1.00 (1.00) |
| $C_{trough}$ (ng/mL) | 13.44 (83) | 0.00 (283) |
| $T_{last}$ (hr) | 8.00 (8.00-12.00) | 8.00 (6.00-12.00) |
| $t_{1/2}$ (hr) | 1.44 (14) | 1.27 (26) |
| TAMIC1 | 6.35 (11) | 4.70 (24) |
| TAMIC2 | 4.74 (11) | 3.61 (24) |
| Rac | 0.892 (9) | 0.685 (18) |
| Study Day 6; Urine | | |
| $Ae_{24}$ (ug) | 139000 (30) (N = 9, n = 8) | 253000 (26) (N = 9, n = 9) |
| Ae % (%) | 16.2 (29) (N = 9, n = 8) | 17.3 (26) (N = 9, n = 9) |
| CL/R (mL/hr) | 7.77 (21) (N = 9, n = 6) | 22.0 (25) (N = 9, n = 8) |

[a]Geometric mean (% CV) for $AUC_{inf}$, $AUC_{tau}$, $C_{max}$, and CL/R; arithmetic mean (% CV) for $t_{1/2}$, AE %; median (range) for $T_{max}$, $T_{last}$, TAMIC1, and TAMIC2.
$AE_{24}$ = amount of sulopenem excreted unchanged in urine over 24 hours post dose administration,
AE % = percent of sulopenem dose excreted in urine,
$AUC_{inf}$ = area under the concentration-time curve from time 0 to infinite time,
$AUC_{tau}$ = area under the concentration-time curve from time 0 to $time_\tau$ (the dosing interval),
BID = twice daily,
CL/R = renal clearance,
$C_{max}$ = maximum (peak) observed drug concentration after single dose administration,
$C_{trough}$ = minimum (trough) observed drug concentration,
$MIC_{0.5}$ = time above the duration of plasma concentrations exceeding 0.5 µg/mL,
$MIC_{1.0}$ = time above the duration of plasma concentrations exceeding 1.0 µg/mL,
N = number of subjects;
n = number of subjects contributing to the mean,
NC = summary statistics not calculated,
Rac = accumulation ratio,
$t_{1/2}$ = elimination half-life,
TAMIC1 = time above minimum inhibitory concentration, when minimum concentration is 0.5 µg/mL,
TAMIC2 = time above minimum inhibitory concentration, when minimum concentration is 1.0 µg/mL,
$T_{max}$ = time to reach peak or maximum concentration following drug administration.

Example 2: Comparison of Probenecid's Effects on Plasma Pharmacokinetic Parameters for β-Lactam Compounds by Oral Administration and Continuous Infusion The pharmacokinetics of Compound III-2b wer studies in a randomized, subject-blinded, investigator- and sponsor-open, placebo-controlled, multiple-dose study, run in parallel cohorts. There were 7 cohorts of approximately 10 subjects each (4:1 active:placebo). Subjects were dosed BID (every 12 hours) for 6 days and on Day 7 they were dosed only once. Blood samples were obtained at prespecified intervals in order to characterize pharmacokinetics. Results are provided in Table 5.

TABLE 5

Geometric mean (CV %) of plasma pharmacokinetic parameters - oral administration.

| Parameter (units) | Cohorts (Treated with Compound III-2b) | | | | | |
|---|---|---|---|---|---|---|
| | 1 N = 8 | 2 N = 8 | 3 N = 8 | 4 N = 8 | 6 N = 8 | 7 N = 8 |
| Day 1 | | | | | | |
| Number of Subjects, n | 8 | 6 | 5 | 8 | 8 | 7 |
| $C_{max}$ (ng/mL) | 4420 (24) | 2760 (13) | 3700 (42) | 1470 (34) | 2950 (22) | 3320 (36) |
| $AUC_{inf}$ (ng · h/mL) | 9430 (13) | 6680 (20) | 12900 (23) | 3400 (20) | 11000 (25) | 8290 (6) |
| $AUC_{last}$ (ng · h/mL) | 9330 (13) | 6770 (22) | 12100 (21) | 3260 (22) | 10800 (26) | 7670 (13) |
| $T_{max}^{a}$ (h) | 1.50 [1.05-4.00] | 1.50 [0.50-6.03] | 2.50 [1.50-4.00] | 1.03 [0.50-2.00] | 2.50 [1.00-4.00] | 1.75 [1.00-6.00] |
| $t_{1/2}^{b}$ (h) | 0.823 (13) | 1.37 (33) | 1.20 (14) | 0.862 (19) | 1.23 (13) | 1.26 (40) |
| $TAMIC_{0.5}^{a}$ (h) | 4.35 [3.19-5.76] | 3.69 [3.09-7.04] | 6.34 [4.54-9.39] | 2.66 [2.15-4.35] | 6.52 [5.31-7.34] | 4.90 [2.91-5.77] |
| $TAMIC_{1.0}^{a}$ (h) | 3.21 [2.31-4.98] | 2.91 [1.90-4.69] | 4.81 [2.92-6.91] | 1.38 [0.00-1.67] | 4.80 [2.88-5.40] | 3.32 [2.29-3.63] |
| Day 7 | | | | | | |
| Number of Subjects, n | 8 | 7 | 6 | 7 | 8 | 6 |
| $C_{max}$ (ng/mL) | 3770 (23) | 2410 (33) | 2670 (28) | 1310 (22) | 3300 (16) | 2090 (28) |
| $AUC_{inf}$ (ng · h/mL) | 7800 (17) | 6020 (16) | 9950 (15) | 2990 (23) | 11900 (24) | 6750 (11) |
| $AUC_{last}$ (ng · h/mL) | 7670 (17) | 6070 (19) | 9710 (15) | 2730 (27) | 11500 (24) | 6230 (16) |
| $T_{max}^{a}$ (h) | 2.00 [1.50-3.00] | 1.75 [1.00-6.00] | 2.51 [1.00-4.00] | 1.50 [0.50-3.02] | 2.00 [1.00-4.00] | 4.00 [2.00-6.00] |
| $t_{1/2}^{b}$ (h) | 0.761 (11) | 1.08 (24) | 0.901 (14) | 0.797 (16) | 1.50 (17) | 0.790 (2) |
| $R_{ac}^{b}$ | 0.832 (13) | 0.910 (11) | 0.809 (14) | 0.873 (29) | 1.10 (24) | 0.827 (21) |
| $TAMIC_{0.5}^{a}$ (h) | 3.32 [2.85-5.02] | 4.18 [2.76-6.96] | 5.96 [4.54-6.75] | 2.38 [1.30-3.72] | 6.26 [4.70-7.36] | 4.62 [4.43-4.89] |
| $TAMIC_{1.0}^{a}$ (h) | 2.64 [2.10-4.22] | 2.72 [1.95-3.17] | 4.44 [3.23-5.47] | 0.803 [0.00-2.13] | 4.67 [3.00-5.85] | 3.22 [1.69-3.94] |

TABLE 5-continued

Geometric mean (CV %) of plasma pharmacokinetic parameters - oral administration.

| | Cohorts (Treated with Compound III-2b) | | | | | |
|---|---|---|---|---|---|---|
| Parameter (units) | 1<br>N = 8 | 2<br>N = 8 | 3<br>N = 8 | 4<br>N = 8 | 6<br>N = 8 | 7<br>N = 8 |
| Ae24$^{b,c}$ (mg) | 138.7 (27) | 74.4 (23) | | | | |
| Ae24%$^{b,c,d}$ (%) | 19.0 (27) | 10.2 (23) | | | | |
| CLr$^{b,c}$ (L/h) | 17.4 (19) | 12.2 (30) | | | | |

$^a$Median (range).
$^b$Arithmetic mean (CV %).
$^c$Collected for Cohorts 1 and 2 only.
$^d$Ratio was adjusted for the MW difference between sulopenem (MW = 349.45) and Compound III-2b (MW = 477.62).
Cohort 1 was Compound III-2b 1 g BID in the fed state.
Cohort 2 was Compound III-2b 1 g BID in the fasted state.
Cohort 3 was Compound III-2b 1.5 g BID in the fed state.
Cohort 4 was Compound III-2b 0.5 g BID in the fasted state.
Cohort 6 was Compound III-2b 1 g plus probenecid 1 g BID in the fasted state.
Cohort 7 was Compound III-2b 1 g TID in the fed state.
N = the total number of subjects in the treatment group in the indicated population.
n = the number of subjects with estimable AUC$_{inf}$ and t½.
CV = coefficient of variation;
C$_{max}$ = maximum observed plasma concentration within the dosing interval;
AUC$_{inf}$ = area under the plasma concentration-time curve from time 0 extrapolated to infinite time;
AUC$_{last}$ = area under the plasma concentration-time curve from time 0 to time of the last quantifiable concentration;
T$_{max}$ = time to C$_{max}$;
t½ = elimination half-life;
TAMIC$_{0.5}$ = duration of time plasma drug concentrations exceeded 0.5 μg/mL;
TAMIC$_{1.0}$ = duration of time plasma drug concentrations exceeded 1.0 μg/mL;
R$_{ac}$ = accumulation ratio;
Ae24 = amount of unchanged drug excreted in urine over 24 hours postdose;
Ae24% = cumulative amount of unchanged drug recovered in the urine up to time 24-hour postdose, expressed as a percent of administered dose;
CL$_r$ = renal clearance;
BID = twice daily;
TID = 3 times daily;
MW = molecular weight.

The pharmacokinetics of sulopenem delivered intravenously were studied in a randomized, investigator-blind, subject-blind, sponsor-open, placebo-controlled, multiple-dose study of sulopenem. There were 5 cohorts dosed. Each subject was dosed for up to 14 days. Each cohort consisted of 10 subjects. Blood samples were obtained at prespecified intervals in order to characterize pharmacokinetics. Results are provided in Table 6.

TABLE 6

Geometric mean (CV %) of plasma pharmacokinetic parameters - continuous infusion.

| Parameter (units)$^a$ | 800 mg<br>(3 h BID)<br>N = 8 | 1200 mg<br>(1 h BID)<br>N = 8 | 1600 mg<br>(1.5 h BID)<br>N = 8 | 1200 mg<br>(2.5 h BID)<br>N = 8 | 2000 mg<br>(1.5 h BID)<br>N = 8 |
|---|---|---|---|---|---|
| | | | Day 1 | | |
| C$_{max}$ (ng/mL) | 7270 (21) | 32500 (41) | 40100 (14) | 16600 (11) | 51500 (16) |
| AUC$_{inf}$ (ng · hr/mL) | 22400 (20) | 42300 (29) | 67300 (13) | 41900 (11) | 90300 (17) |
| AUC$_{last}$ (ng · hr/mL) | 22300 (20) | 42200 (29) | 67100 (13) | 41800 (11) | 90100 (17) |
| T$_{max}$$^b$ (hr) | 2.00 [2.00-3.00] | 1.00 [1.00-1.00] | 1.50 [1.00-1.50] | 2.25 [2.00-2.50] | 1.50 [1.00-1.50] |
| t$_{1/2}$$^c$ (hr) | 0.825 (19) | 1.04 (9) | 1.04 (12) | 1.12 (8) | 1.12 (26) |
| TAMIC0.5 μg/mL$^b$ (h) | 4.99 [4.79-5.53] | 4.93 [4.28-5.94] | 5.61 [5.22-6.41] | 5.59 [4.83-6.63] | 6.47 [5.59-7.08] |
| TAMIC1.0 μg/mL$^b$ (h) | 4.47 [4.12-4.68] | 3.86 [3.54-4.64] | 4.67 [3.99-4.99] | 4.74 [4.15-5.57] | 5.39 [4.62-6.20] |
| | | | Day 14 | | |
| C$_{max}$ (ng/mL) | 8970 (17) | 30700 (16) | 31800 (12) | 13500 (11) | NE |
| AUC$_{inf}$ (ng · hr/mL) | 26500 (15) | 41400 (17) | 54900 (11) | 34600 (10) | |

TABLE 6-continued

Geometric mean (CV %) of plasma pharmacokinetic parameters - continuous infusion.

| Parameter (units)[a] | 800 mg (3 h BID) N = 8 | 1200 mg (1 h BID) N = 8 | 1600 mg (1.5 h BID) N = 8 | 1200 mg (2.5 h BID) N = 8 | 2000 mg (1.5 h BID) N = 8 |
|---|---|---|---|---|---|
| $AUC_{last}$ (ng · hr/mL) | 26400 (15) | 41300 (17) | 54700 (12) | 34500 (10) | NE |
| $T_{max}$[b] (hr) | 2.00 [2.00-3.00] | 1.00 [1.00-1.00] | 1.25 [1.00-1.50] | 2.00 [2.00-2.50] | NE |
| $t_{1/2}$[c] (hr) | 0.889 (15) | 1.05 (20) | 1.20 (10) | 1.01 (26) | NE |
| $R_{ac}$[c] | 1.15 (29) | 0.928 (17) | 0.791 (9) | 0.841 (9) | NE |
| TAMIC0.5 µg/mL[a] (h) | 5.05 [4.88-5.72] | 4.67 [3.78-6.47] | 5.77 [4.19-6.09] | 4.79 [4.59-5.38] | NE |
| TAMIC1.0 µg/mL[a] (h) | 4.42 [4.31-4.66] | 3.63 [3.16-5.22] | 4.45 [3.73-4.62] | 3.96 [3.84-4.62] | NE |
| $Ae_{24}$[c] (mg) | 406 (17) | 614 (19) | 1080 (14) | 643 (10) | NE |
| $Ae_{24}$[c] (%) | 50.8 (17) | 51.1 (19) | 67.4 (14) | 53.6 (10) | NE |
| $CL_r$[c] (L/hr) | 15.4 (18) | 14.7 (13) | 19.6 (14) | 18.8 (17) | NE |

[a]Pharmacokinetic parameters are defined in Tables 1-5.
[b]median [range]
[c]arithmetic mean (CV %)]
BID = twice daily,
h = hours,
CV = coefficient of variation,
NE = not estimated, study stopped before Day 14 assessment,
TAMIC0.5 = duration of plasma sulopenem concentrations exceeding 0.5 µg/mL,
TAMIC1.0 = duration of plasma sulopenem concentrations exceeding 1.0 µg/mL.

Example 3: Summary of Various Studies in Examples 1 and 2

The results of various studies described in Examples 1 and 2 were summarized in Tables 7A-7C below, which were further summarized in FIG. 1. It was observed that, when Compound III-1b or Compound III-2b was administered alone through the oral route, the AUC of sulopenem on Day 7 was lower than that on Day 1. Further, it was observed that, when Compound III-1b or Compound III-2b was co-administered with probenecid, the AUC of sulopenem was increased on Day 7 beyond that seen on Day 1.

TABLE 7A

Plasma pharmacokinetic parameters following administration of Compound III-1b or Compound III-2b with and without probenecid (based on Tables 1 and 3 in Example 1).

| Parameter (units) | Compound III-1b | Compound III-1b + 500 mg Probenecid | Compound III-2b | Compound III-2b + 500 mg Probenecid |
|---|---|---|---|---|
| Day 1 |
| $AUC_{tau}$ (hr*ng/mL) | 2843.7 | 4186.1 | 3623.8 | 3857.2 |
| Day 7 |
| $AUC_{tau}$ (hr*ng/mL) | 1889.9 | 4402.5 | 2626.3 | 4276.4 |

TABLE 7A-continued

Plasma pharmacokinetic parameters following administration of Compound III-1b or Compound III-2b with and without probenecid (based on Tables 1 and 3 in Example 1).

| Parameter (units) | Compound III-1b | Compound III-1b + 500 mg Probenecid | Compound III-2b | Compound III-2b + 500 mg Probenecid |
|---|---|---|---|---|
| Day 1-Day 7 |
| $AUC_{tau}$ difference (hr*ng/mL) (%) | −953.8 (−33.5%) | 216.4 (5.2%) | −1000.5 (27.6%) | 419.2 (10.9%) |

$AUC_{tau}$ = area under the concentration time curve from time 0 to 12 hours.

TABLE 7B

Plasma pharmacokinetic parameters following administration of Compound III-2b with and without probenecid (based on Table 4 of Example 1).

| Parameter (units) | Compound III-2b (2000 mg) | Compound III-2b (1200 mg) + Probenecid |
|---|---|---|
| Day 1 |
| $AUC_{tau}$ (hr*ng/mL) | 17500 | 20000 |
| Day 10 |
| $AUC_{tau}$ (hr*ng/mL) | 12200 | 18800 |
| Day 1-Day 10 |
| $AUC_{tau}$ difference (hr*ng/mL) (%) | −5300 (−30.3%) | −1200 (−6.0%) |

$AUC_{tau}$ = area under the concentration time curve from time 0 to 12 hours.

TABLE 7C

Plasma pharmacokinetic parameters following administration of various doses of Compound III-2b with and without probenecid (based on Table 5 in Example 2).

| Parameter (units) | Compound III-2b (1000 mg) | Compound III-2b (1000 mg) + Probenecid | Compound III-2b (1500 mg) | Compound III-2b (1000 mg) FED | Compound III-2b (500 mg) FED | Compound III-2b (1000 mg) TID FED |
|---|---|---|---|---|---|---|
| | | | Day 1 | | | |
| $AUC_{inf}$ (hr * ng/mL) | 6680 | 11000 | 12900 | 9430 | 3400 | 8290 |
| | | | Day 7 | | | |
| $AUC_{inf}$ (hr * ng/mL) | 6020 | 11900 | 9950 | 7800 | 2990 | 6750 |
| | | | Day 1-Day 7 | | | |
| $AUC_{inf}$ difference (hr * ng/mL) (%) | −660 (−9.9%) | 900 (8.2%) | −2950 (−22.9%) | −1630 (−17.3%) | −410 (−12.1%) | −1540 (−18.6%) |

$AUC_{inf}$ = the area under the concentration time curve extrapolated to infinity.

Example 4: Effects of Administrating β-Lactam Compounds and Probenecid by the Same Administration Route Normal and healthy subjects were given the β-lactam compound (Compound III-2b; sulopenem etzadroxil) and probenecid in two separate studies. In Study No. 1, subjects were administered 500 mg of sulopenem etzadroxil as a powder for oral suspension and simultaneously dosed with 500 mg of probenecid provided as a monolayer tablet. In Study No. 2, subjects were administered 500 mg of sulopenem etzadroxil with 500 mg of probenecid in an oral co-formulation. The results of the two studies are shown in FIGS. 2-5 and Table 8 below.

TABLE 8

Comparison of AUC in subjects given sulopenem etzadroxil and probenecid

| | $AUC_{last}$ ng · hr/ml | |
|---|---|---|
| | Fasted | Fed |
| Study No. 1 | 4325.9 | 6592.8 |
| Study No. 2 | 5099.5 | 7336.4 |
| Difference (% Increase) | 773.6 (17.9%) | 743.6 (11.3%) |

It is observed that administration of sulopenem etzadroxil and probenecid in the co-formulation results in an increase in the amount of sulopenem in the blood relative to dosing each agent in a separate formulation.

Administration in the fasted state of a combination of sulopenem etzadroxil and probenecid in the co-formulation results in a 17.9% increase in the amount of sulopenem in the blood, as measured by the area under the curve, relative to the same amount of sulopenem etzadroxil delivered as powder in a bottle administered with probenecid in a monolayer tablet.

Similarly, the administration in the fed state of a combination of sulopenem etzadroxil and probenecid in the co-formulation results in a 11.3% increase in the amount of sulopenem in the blood, as measured by the area under the curve, relative to the same amount of sulopenem etzadroxil delivered as powder in a bottle administered with probenecid in a monolayer tablet.

EQUIVALENTS

It is to be understood that the invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method of treating or preventing uncomplicated urinary tract infection, comprising:
    administering to a subject in need thereof from 400 mg to 600 mg of a β-lactam compound or a pharmaceutically acceptable salt thereof, and from 400 mg to 600 mg of probenecid or a pharmaceutically acceptable salt thereof, simultaneously twice daily for from 5 days to 10 days,
    wherein the β-lactam compound is:

(Compound III-2)

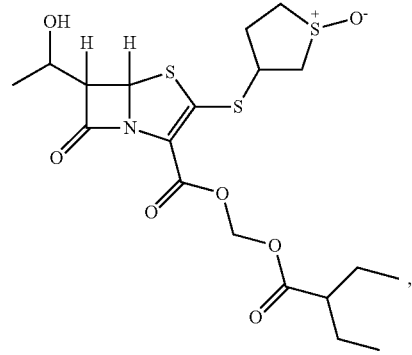

or a pharmaceutically acceptable salt thereof.

2. The method of claim 1, wherein the β-lactam compound or the pharmaceutically acceptable salt thereof, and probenecid or the pharmaceutically acceptable salt thereof, are administered by oral administration.

3. The method of claim 1, wherein an oral co-formulation comprising the β-lactam compound or the pharmaceutically acceptable salt thereof and probenecid or the pharmaceutically acceptable salt thereof is administered.

4. The method of claim 3, wherein a tablet comprising the β-lactam compound or the pharmaceutically acceptable salt thereof and probenecid or the pharmaceutically acceptable salt thereof is administered.

5. The method of claim 1, wherein a food is administered to the subject during the administration of the β-lactam compound or the pharmaceutically acceptable salt thereof and probenecid or the pharmaceutically acceptable salt thereof.

6. The method of claim 1, wherein the subject in need thereof is a human.

7. The method of claim 1, wherein the β-lactam compound is selected from the group consisting of:

(Compound III-2a)

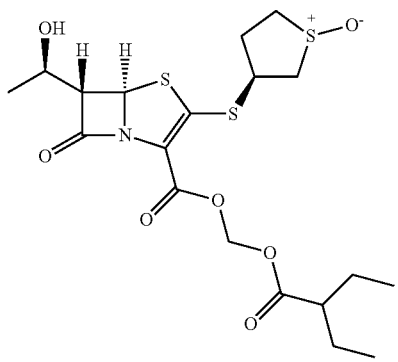

or (Compound III-2b)

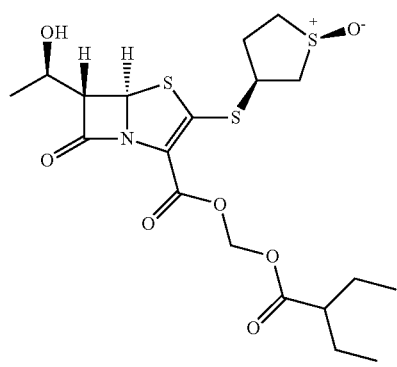

, (Compound III-2b)

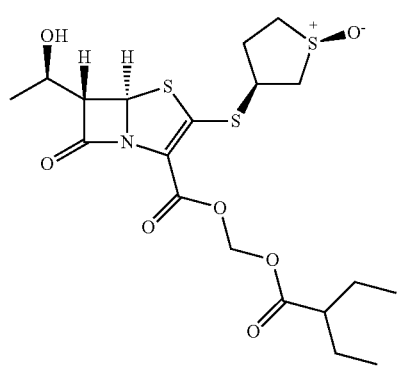

or pharmaceutically acceptable salts thereof.

8. The method of claim 1, wherein the β-lactam compound is:

(Compound III-2a)

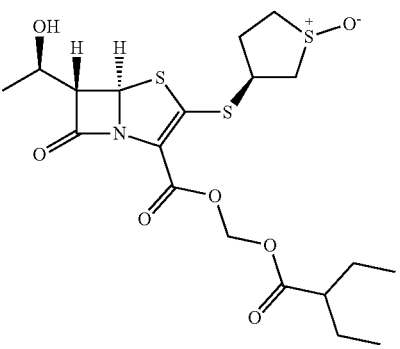

or a pharmaceutically acceptable salt thereof.

9. The method of claim 1, wherein the β-lactam compound is:

(Compound III-2b)

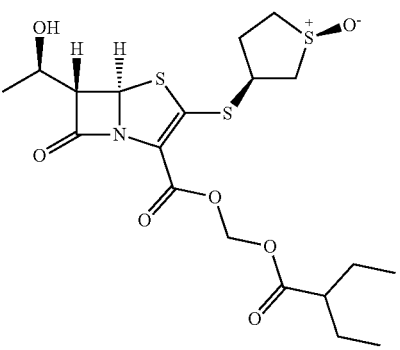

or a pharmaceutically acceptable salt thereof.

10. The method of claim 1, wherein the β-lactam compound or the pharmaceutically acceptable salt thereof, and probenecid or the pharmaceutically acceptable salt thereof, are administered for 5 days.

* * * * *

UNITED STATES PATENT AND TRADEMARK OFFICE
CERTIFICATE OF CORRECTION

PATENT NO.       : 12,109,197 B2
APPLICATION NO.  : 18/065400
DATED            : October 8, 2024
INVENTOR(S)      : Michael Dunne It is certified that error appears in the above-identified patent and that said Letters Patent is hereby corrected as shown below:

In the Claims

At Column 90, Claim number 4, Line number 65:
"ß-lactam compound or the pharmaceutically acceptable salt"
Should read:
--β-lactam compound or the pharmaceutically acceptable salt--

At Column 91, Claim number 7, Line numbers 8-60:
"7. The method of claim 1, wherein the β-lactam compound is selected from the group consisting of:

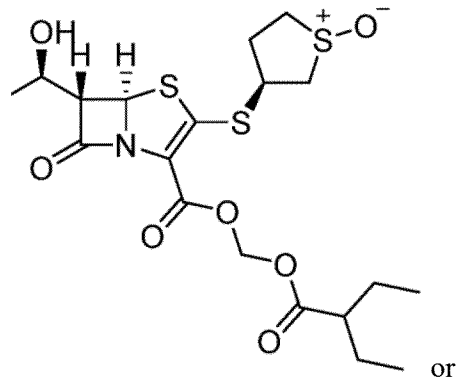

(Compound III-2a)

or

Signed and Sealed this
Twelfth Day of November, 2024

Katherine Kelly Vidal
*Director of the United States Patent and Trademark Office*

(Compound III-2b)
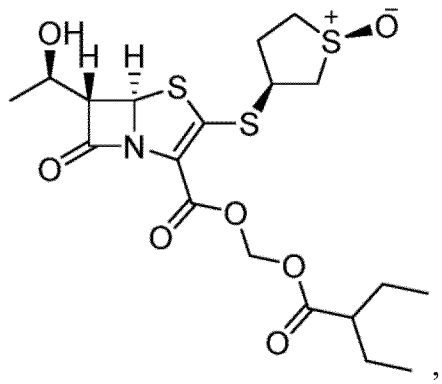
(Compound III-2b)
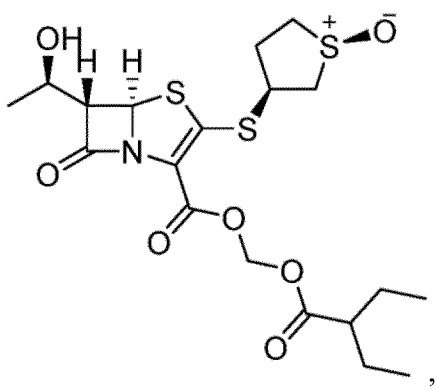
or pharmaceutically acceptable salts thereof."
Should read:
--7. The method of claim 1, wherein the β-lactam compound is selected from the group consisting of:
(Compound III-2a)
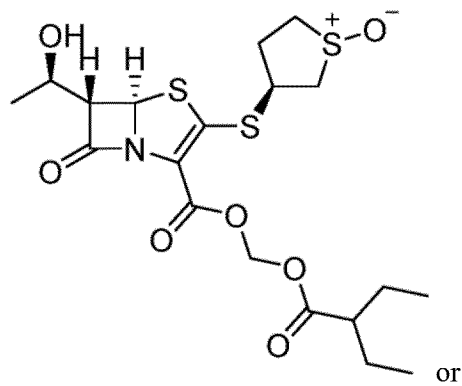
or

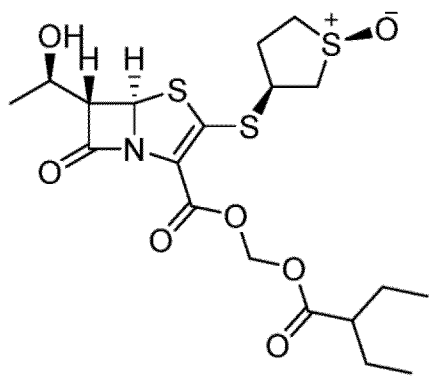 (Compound III-2b)
or pharmaceutically acceptable salts thereof. --